United States Patent [19]
Boursnell et al.

[11] Patent Number: 5,719,054
[45] Date of Patent: Feb. 17, 1998

[54] RECOMBINANT VIRUS VECTORS ENCODING HUMAN PAPILLOMAVIRUS PROTEINS

[75] Inventors: Michael E. Boursnell; Stephen C. Inglis; Alan J. Munro, all of Cambridge, Great Britain

[73] Assignee: Cantab Pharmaceuticals Research Limited, Cambridge, United Kingdom

[21] Appl. No.: 117,083

[22] PCT Filed: Mar. 10, 1992

[86] PCT No.: PCT/GB92/00424

§ 371 Date: Nov. 8, 1993

§ 102(e) Date: Nov. 8, 1993

[87] PCT Pub. No.: WO92/16636

PCT Pub. Date: Oct. 1, 1992

[30] Foreign Application Priority Data

Mar. 14, 1991 [GB] United Kingdom ............... 9105383

[51] Int. Cl.$^6$ ............................. C12N 15/86; C07H 21/04
[52] U.S. Cl. ................................... 435/320.1; 536/23.72
[58] Field of Search ............................. 435/69.1, 172.1, 435/172.3, 69.7, 320.1; 536/23.1, 24.3, 23.72

[56] References Cited

FOREIGN PATENT DOCUMENTS

WO9010459  9/1990  WIPO.
WO9012880  11/1990  WIPO.
WO9012882  11/1990  WIPO.

OTHER PUBLICATIONS

Meneguzzi et al. "Vaccinia Recombinants Expressing Early Bovine Papilloma Virus (BPVI) Proteins: Retardation of BPVI Tumour Development", Vaccine, vol. 8, Jun. 1990, pp. 199–204.

Meneguzzi et al. "Immunization Against Human Papillomovirus Type 16 Tumor Cells with Recombinant Vaccinia Viruses Expressing E6 and E7", Virology, vol. 181, Mar. 1991, pp. 62–69.

Chen et al., Proc. Natl. Acad. Sci. USA, 88 110–114 (1991) "Human papillomavirus type 16 nucleoprotein E7 is a tumour".

Lathe et al., Nature, 326 878–880 (1987) "Tumour prevention and rejection with recombinant vaccinia".

Mackett et al., Journal of Virology, 49(3) 857–864 (1984) "General method for production and selection of infectious vaccinia virus recombinants expression foreign genes".

Rixon, et al., Journal of General Virology, 71 2931–2939 (1990) "Insertion of DNA sequences at a unique restriction enzyme site engineered for vector purposes into the genome of herpex simplex virus type 1".

Sadovnikova et al., International Immunology, 6(2) 289–296 (1994) "Limitations of predictive motifs revealed by cytotoxic T lymphocyte epitope mapping of the human papilloma virus E7 protein".

Eloit et al., Journal of General Virology, 71 2425–2431 (1990) "Construction of a defective adenovirus vector expressing the pseudorables virus glycoprotein gp50 and its use as a live vaccine".

Ballay et al., The EMBO Journal, 4 (13B) 3861–3865 (1985) "In vitro and in vivo synthesis of the hepatitis B virus surface antigen and of the receptor for polymerized human serum albumin from recombinant human adenoviruses".

Chesters et al., Abstract—J. Gen. Virol., 71(2) 449–453 (1990) "Analysis of human papillomvirus type 16 open reading frame E7 immortalizing function in rat embryo fibroblast cells".

Naito et al. Biochem. and Biophys. Res. Comm. 174, 1 pp. 305–312 (1991) "Homologous recombination in bovine papillomavirus shuttlevector: Effect of relative orientation of substrate sequences".

Kitamura, et al. Mol. Gen. Genet 222 pp. 185–191 (1990) "Homologous recombination in a mammalian plasmid".

Storey, et al. The EMBO Journal 7, 6 pp. 1815–1820 (1988) "Comparison of the in vitro transforming activities of human papillomavirus types".

Jones, et al. Jour. Bio. Chem. 265, 22 pp. 12782–12785 (1990) "Identification of HPV–16 E7 peptides that are potent antagonists of E7 binding to the retinoblastoma suppressor protein".

Primary Examiner—David Guzo
Attorney, Agent, or Firm—Walter H. Dreger; Jan P. Brunelle

[57] ABSTRACT

The invention provides a recombinant virus vector for use as an immunotherapeutic or vaccine. The recombinant virus vector comprises at least one pair of nucleotide sequences heterologous to the virus and which have sufficient sequence homology that recombination between them might be expected. The pair of nucleotide sequences are arranged in the virus vector such that they are inverted with respect to each other. The virus vector is able to infect a mammalian host cell and express as polypeptide the heterologous nucleotide sequences in the host cell. For infection thought to be caused by HPV infection, the pair of nucleotide sequences encode part or all of human papillomavirus (HPV) wild-type proteins or mutant proteins immunologically cross-reactive therewith. For an immunotherapeutic or vaccine against cervical cancer, the recombinant virus vector encodes part or all of the HPV wild-type proteins HPV16E7 and HPV18E7 or mutant proteins immunologically cross-reactive therewith.

37 Claims, 34 Drawing Sheets

FIG._1a-1

```
ATCCCATGGACCAAAAGAGAACTGCAATGTTTCAGGACCCACAGGAGCGACCCAGAAAGT   60
 I  P  W  T  K  R  E  L  Q  C  F  R  T  H  R  S  D  P  E  S
   S  H  G  P  K  E  N  C  N  V  S  G  P  T  G  A  T  Q  K  V
     P  M  D  Q  K  R  T  A  M  F  Q  D  P  Q  E  R  P  R  K
        ^ Start of E6 coding region TACCACAGTTATGCACAGAGCTGCAAACAACTATACATGATATAATATTAGAATGTGTGT  120
 Y  H  S  Y  A  Q  S  C  K  Q  L  Y  M  I  *  Y  *  N  V  C
   T  T  V  M  H  R  A  A  N  N  Y  T  *  Y  N  I  R  M  C  V
     P  Q  L  C  T  E  L  Q  T  T  I  H  D  I  I  L  E  C  V  Y ACTGCAAGCAACAGTTACTGCGACGTGAGGTATATGACTTTGCTTTTCGGGATTTATGCA  180
 T  A  S  N  S  Y  C  D  V  R  Y  M  T  L  L  F  G  I  Y  A
   L  Q  A  T  V  T  A  T  *  G  I  *  L  C  F  S  G  F  M  H
     C  K  Q  Q  L  L  R  R  E  V  Y  D  F  A  F  R  D  L  C  I TAGTATATAGAGATGGGAATCCATATGCTGTATGTGATAAATGTTTAAAGTTTTATTCTA  240
 *  Y  I  E  M  G  I  H  M  L  Y  V  I  N  V  *  S  F  I  L
   S  I  *  R  W  E  S  I  C  C  M  *  *  M  F  K  V  L  F  *
     V  Y  R  D  G  N  P  Y  A  V  C  D  K  C  L  K  F  Y  S  K AAATTAGTGAGTATAGACATTATTGTTATAGTTTGTATGGAACAACATTAGAACAGCAAT  300
 K  L  V  S  I  D  I  I  V  I  V  C  M  E  Q  H  *  N  S  N
   N  *  *  V  *  T  L  L  L  *  F  V  W  N  N  I  R  T  A  I
     I  S  E  Y  R  H  Y  C  Y  S  L  Y  G  T  T  L  E  Q  Q  Y ACAACAAACCGTTGTGTGATTTGTTAATTAGGTGTATTAACTGTCAAAAGCCACTGTGTC  360
 T  T  N  R  C  V  I  C  *  L  G  V  L  T  V  K  S  H  C  V
   Q  Q  T  V  V  *  F  V  N  *  V  Y  *  L  S  K  A  T  V  S
     N  K  P  L  C  D  L  L  I  R  C  I  N  C  Q  K  P  L  C  P CTGAAGAAAAGCAAAGACATCTGGACAAAAAGCAAAGATTCCATAATATAAGGGGTCGGT  420
 L  K  K  S  K  D  I  W  T  K  S  K  D  S  I  I  *  G  V  G
   *  R  K  A  K  T  S  G  Q  K  A  K  I  P  *  Y  K  G  S  V
     E  E  K  Q  R  H  L  D  K  K  Q  R  F  H  N  I  R  G  R  W GGACCGGTCGATGTATGTCTTGTTGCAGATCATCAAGAACACGTAGAGAAACCCAGCTGT  480
 G  P  V  D  V  C  L  V  A  D  H  Q  E  H  V  E  K  P  S  C
   D  R  S  M  Y  V  L  L  Q  I  I  K  N  T  *  R  N  P  A  V
     T  G  R  C  M  S  C  C  R  S  S  R  T  R  R  E  T  Q  L  *
```

```
AATCATGCATGGAGATACACCTACATTGCATGAATATATGTTAGATTTGCAACCAGAGAC   540
 N  H  A  W  R  Y  T  Y  I  A  *  I  Y  V  R  F  A  T  R  D
  I  M  H  G  D  T  P  T  L  H  E  Y  M  L  D  L  Q  P  E  T
   S  C  M  E  I  H  L  H  C  M  N  I  C  *  I  C  N  Q  R  Q
      ^ Start of E7 coding region AACTGATCTCTACTGTTATGAGCAATTAAATGACAGCTCAGAGGAGGAGGATGAAATAGA   600
 N  *  S  L  L  L  *  A  I  K  *  Q  L  R  G  G  G  *  N  R
   T  D  L  Y  C  Y  E  Q  L  N  D  S  S  E  E  E  D  E  I
    L  I  S  T  V  M  S  N  *  M  T  A  Q  R  R  R  M  K  *  M TGGTCCAGCTGGACAAGCAGAACCGGACAGAGCCCATTACAATATTGTAACCTTTTGTTG   660
 W  S  S  W  T  S  R  T  G  Q  S  P  L  Q  Y  C  N  L  L  L
   G  P  A  G  Q  A  E  P  D  R  A  H  Y  N  I  V  T  F  C  C
    V  Q  L  D  K  Q  N  R  T  E  P  I  T  I  L  *  P  F  V  A CAAGTGTGACTCTACGCTTCGGTTGTGCGTACAAAGCACACACGTAGACATTCGTACTTT   720
 Q  V  *  L  Y  A  S  V  V  R  T  K  H  T  R  R  H  S  Y  F
   K  C  D  S  T  L  R  L  C  V  Q  S  T  H  V  D  I  R  T  L
    S  V  T  L  R  F  G  C  A  Y  K  A  H  T  *  T  F  V  L  W GGAAGACCTGTTAATGGGCACACTAGGAATTGTGTGCCCCATCTGTTCTCAGAAACCATA   780
 G  R  P  V  N  G  H  T  R  N  C  V  P  H  L  F  S  E  T  I
   E  D  L  L  M  G  T  L  G  I  V  C  P  I  C  S  Q  K  P  *
    K  T  C  *  W  A  H  *  E  L  C  A  P  S  V  L  R  N  H  N ACCCGGGTGA                                                     840
 T  R  V
  P  G  *
   P  G
```

```
ATCCCATGGCGCGCTTTGAGGATCCAACACGGCGACCCTACAAGCTACCTGATCTGTGCA   60
 I  P  W  R  A  L  R  I  Q  H  G  D  P  T  S  Y  L  I  C  A
  S  H  G  A  L  *  G  S  N  T  A  T  L  Q  A  T  *  S  V  H
   P  M  A  R  F  E  D  P  T  R  R  P  Y  K  L  P  D  L  C  T
     ^ Start of E6 coding region CGGAACTGAACACTTCACTGCAAGACATAGAAATAACCTGTGTATATTGCAAGACAGTAT  120
 R  N  *  T  L  H  C  K  T  *  K  *  P  V  Y  I  A  R  Q  Y
  G  T  E  H  F  T  A  R  H  R  N  N  L  C  I  L  Q  D  S  I
   E  L  N  T  S  L  Q  D  I  E  I  T  C  V  Y  C  K  T  V  L TGGAACTTACAGAGGTATTTGAATTTGCATTTAAAGATTTATTTGTGGTGTATAGAGACA  180
 W  N  L  Q  R  Y  L  N  L  H  L  K  I  Y  L  W  C  I  E  T
  G  T  Y  R  G  I  *  I  C  I  *  R  F  I  C  G  V  *  R  Q
   E  L  T  E  V  F  E  F  A  F  K  D  L  F  V  V  Y  R  D  S GTATACCCCATGCTGCATGCCATAAATGTATAGATTTTTATTCTAGAATTAGAGAATTAA  240
 V  Y  P  M  L  H  A  I  N  V  *  I  F  I  L  E  L  E  N  *
  Y  T  P  C  C  M  P  *  M  Y  R  F  L  F  *  N  *  R  I  K
   I  P  H  A  A  C  H  K  C  I  D  F  Y  S  R  I  R  E  L  R GACATTATTCAGACTCTGTGTATGGAGACACATTGGAAAAACTAACTAACACTGGGTTAT  300
 D  I  I  Q  T  L  C  M  E  T  H  W  K  N  *  L  T  L  G  Y
  T  L  F  R  L  C  V  W  R  H  I  G  K  T  N  *  H  W  V  I
   H  Y  S  D  S  V  Y  G  D  T  L  E  K  L  T  N  T  G  L  Y ACAATTTATTAATAAGGTGCCTGCGGTGCCAGAAACCGTTGAATCCAGCAGAAAAACTTA  360
 T  I  Y  *  *  G  A  C  G  A  R  N  R  *  I  Q  Q  K  N  L
  Q  F  I  N  K  V  P  A  V  P  E  T  V  E  S  S  R  K  T  *
   N  L  L  I  R  C  L  R  C  Q  K  P  L  N  P  A  E  K  L  R GACACCTTAATGAAAACGACGATTTCACAACATAGCTGGGCACTATAGAGGCCAGTGCC   420
 D  T  L  M  K  N  D  D  F  T  T  *  L  G  T  I  E  A  S  A
  T  P  *  *  K  T  T  I  S  Q  H  S  W  A  L  *  R  P  V  P
   H  L  N  E  K  R  R  F  H  N  I  A  G  H  Y  R  G  Q  C  H ATTCGTGCTGCAACCGAGCACGACAGGAACGACTCCAACGACGCAGAGAAACACAAGTAT  480
 I  R  A  A  T  E  H  D  R  N  D  S  N  D  A  E  K  H  K  Y
  F  V  L  Q  P  S  T  T  G  T  T  P  T  T  Q  R  N  T  S  I
   S  C  C  N  R  A  R  Q  E  R  L  Q  R  R  R  E  T  Q  V  *
```

```
AATATTAAGTATGCATGGACCTAAGGCAACATTGCAAGACATTGTATTGCATTTAGAGCC   540
  N I K Y A W T * G N I A R H C I A F R A
   I L S M H G P K A T L Q D I V L H L E P
    Y * V C M D L R Q H C K T L Y C I * S P
         ^ Start of E7 coding region CCAAAATGAAATTCCGGTTGACCTTCTATGTCACGAGCAATTAAGCGACTCAGAGGAAGA   600
  P K * N S G * P S M S R A I K R L R G R
   Q N E I P V D L L C H E Q L S D S E E E
    K M K F R L T F Y V T S N * A T Q R K K AAACGATGAAATAGATGGAGTTAATCATCAACATTTACCAGCCCGACGAGCCGAACCACA   660
  K R * N R W S * S S T F T S P T S R T T
   N D E I D G V N H Q H L P A R R A E P Q
    T M K * M E L I I N I Y Q P D E P N H N ACGTCACACAATGTTGTGTATGTGTTGTAAGTGTGAAGCCAGAATTGAGCTAGTAGTAGA   720
  T S H N V V Y V L * V * S Q N * A S S R
   R H T M L C M C C K C E A R I E L V V E
    V T Q C C V C V V S V K P E L S * * K AAGCTCAGCAGACGACCTTCGAGCATTCCAGCAGCTGTTTCTGAACACCCTGTCCTTTGT   780
  K L S R R P S S I P A A V S E H P V L C
   S S A D D L R A F Q Q L F L N T L S F V
    A Q Q T T F E H S S S C F * T P C P L C GTGTCCGTGGTGTGCATCCCAGCAGTAACCCGGGTGA                          840
  V S V V C I P A V T R V
   C P W C A S Q Q * P G *
    V R G V H P S S N P G
```

FIG._1b-2

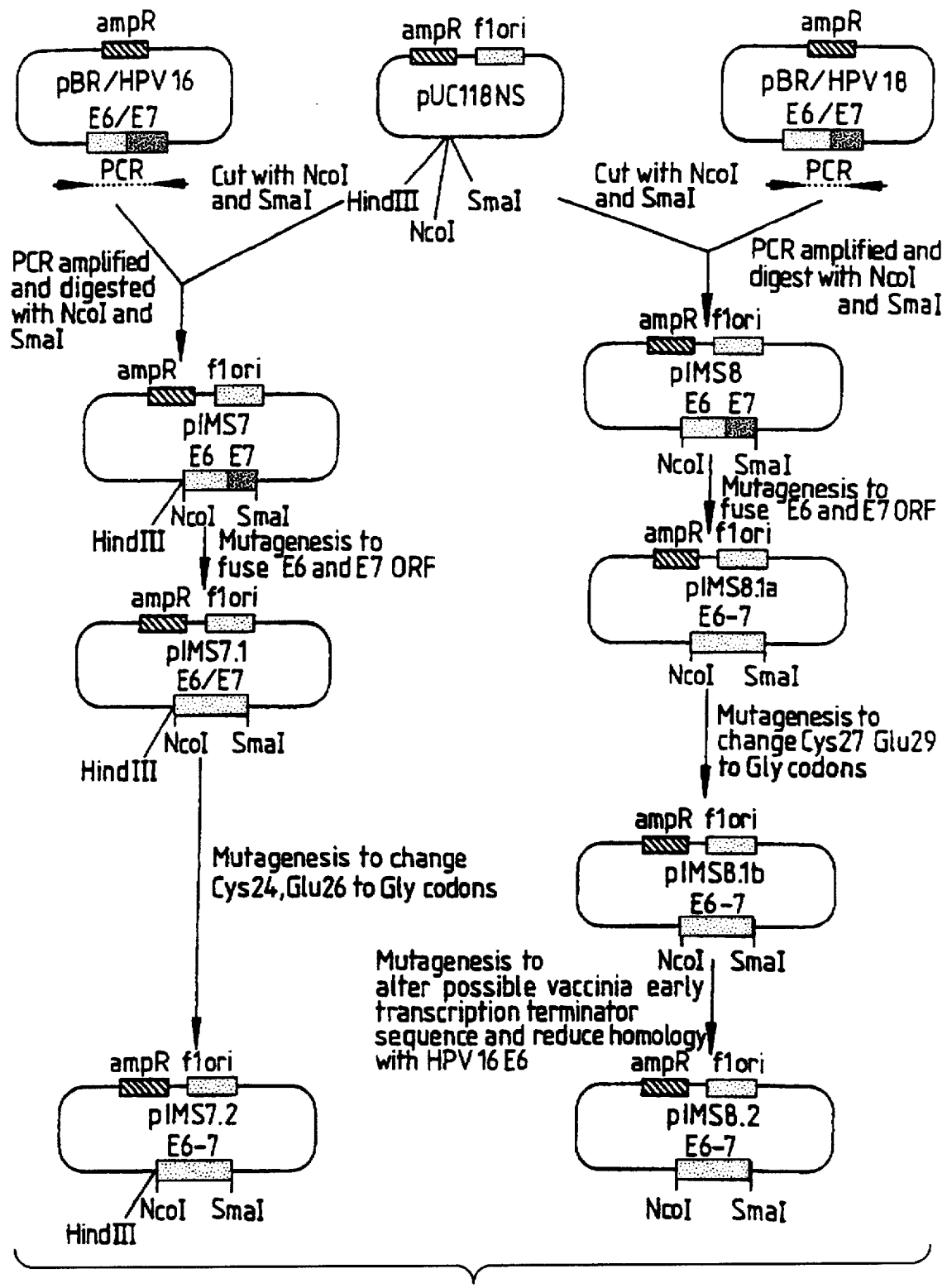
FIG._2

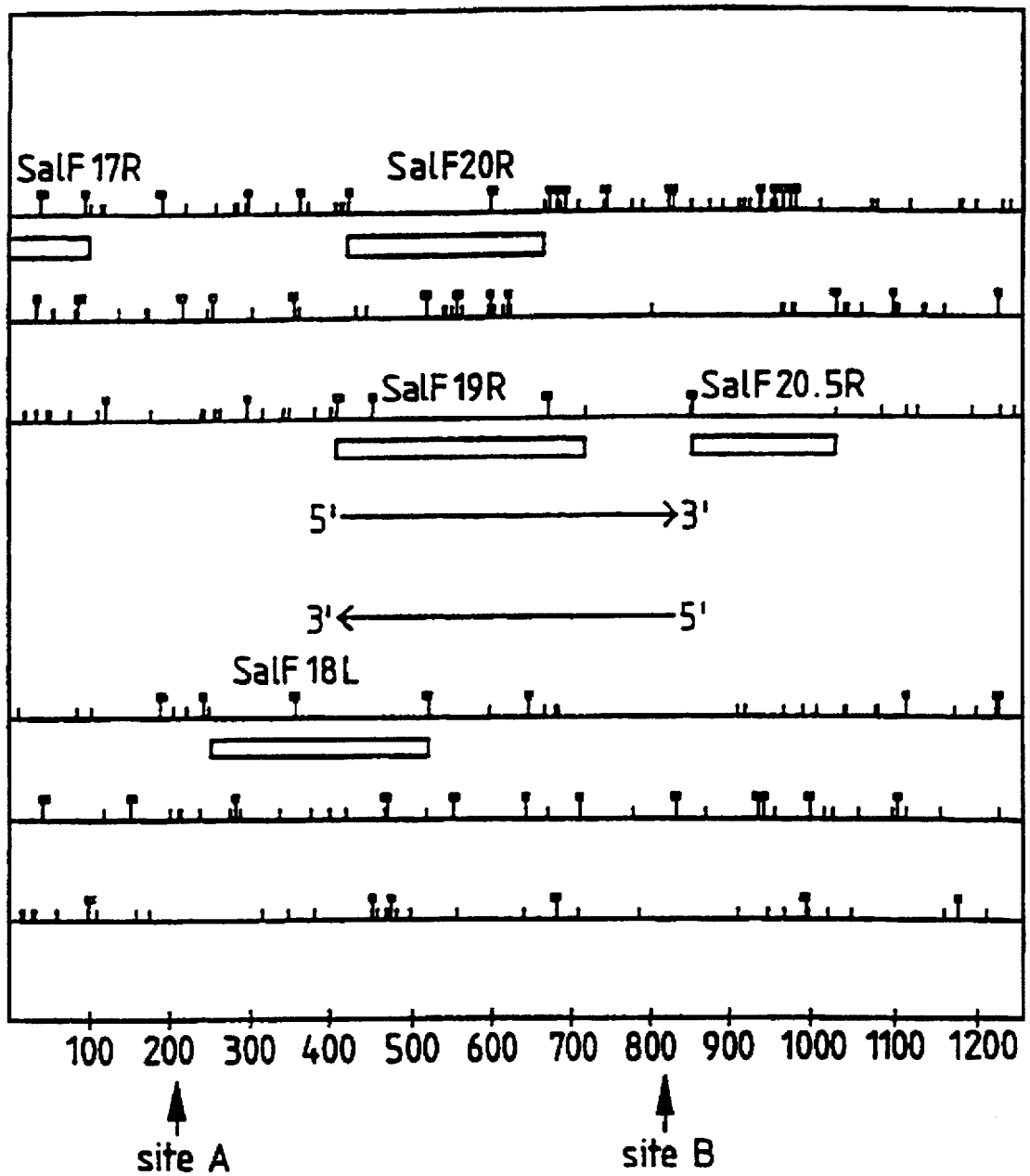
FIG._3

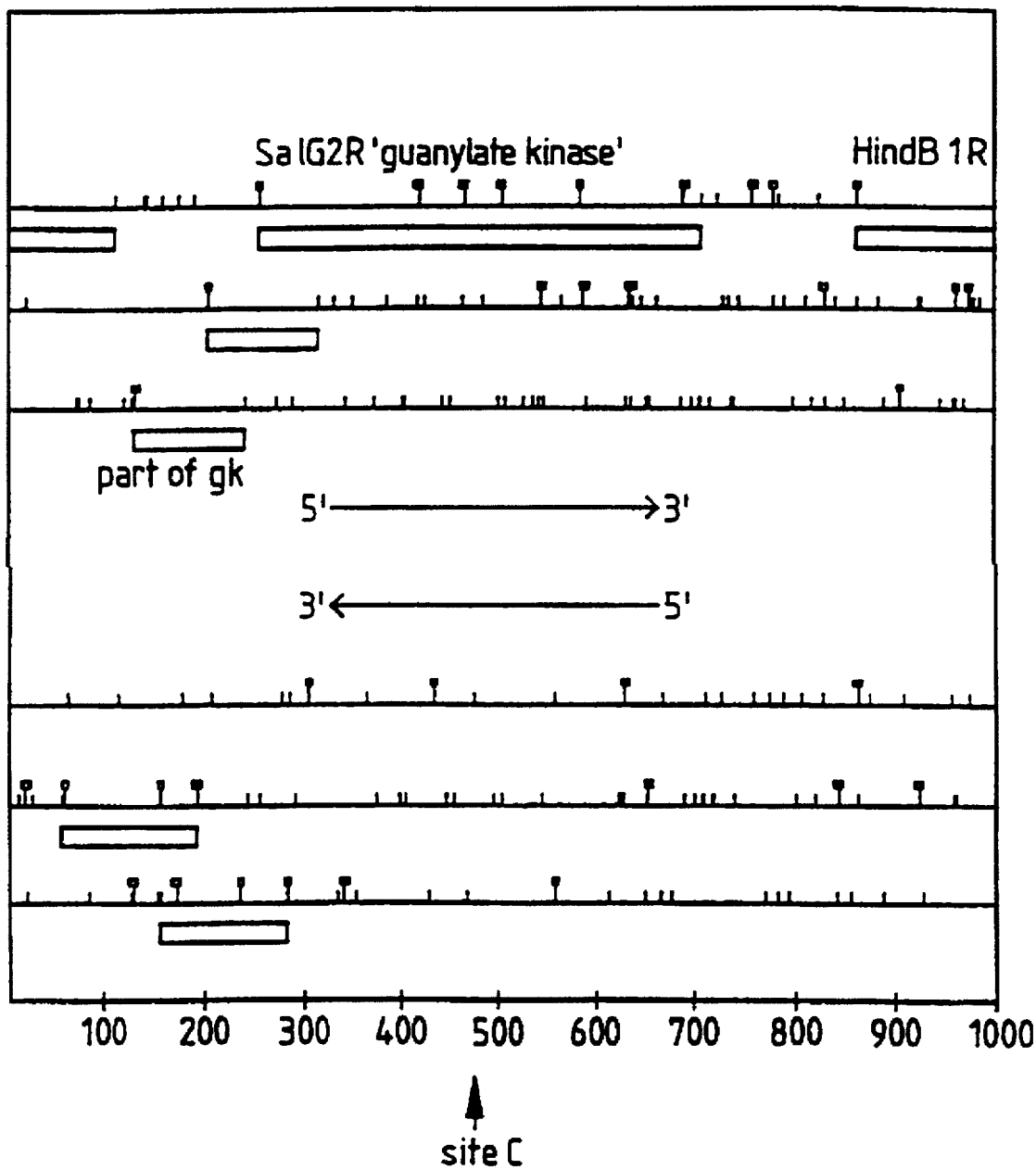
FIG._4

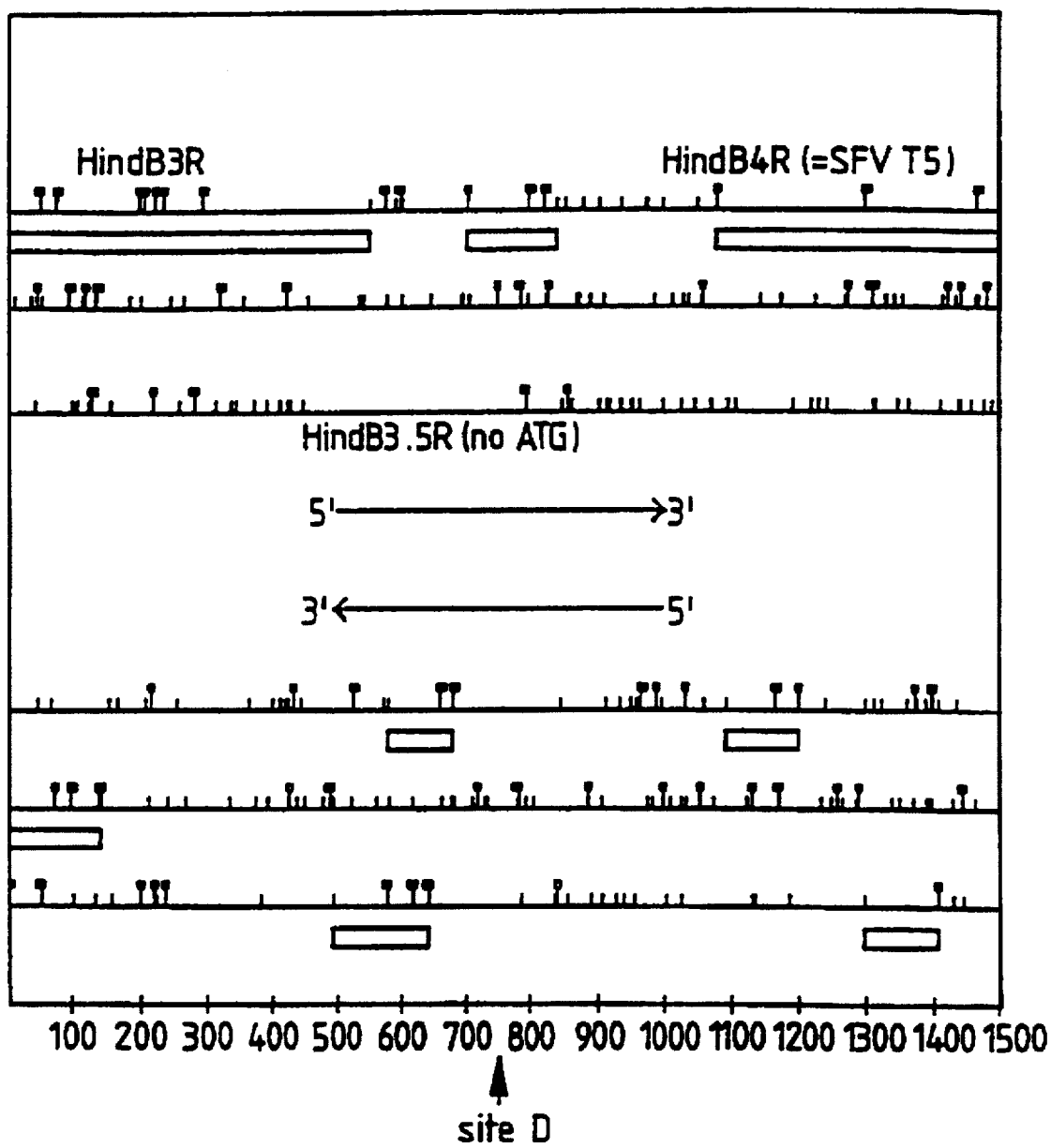
FIG._5

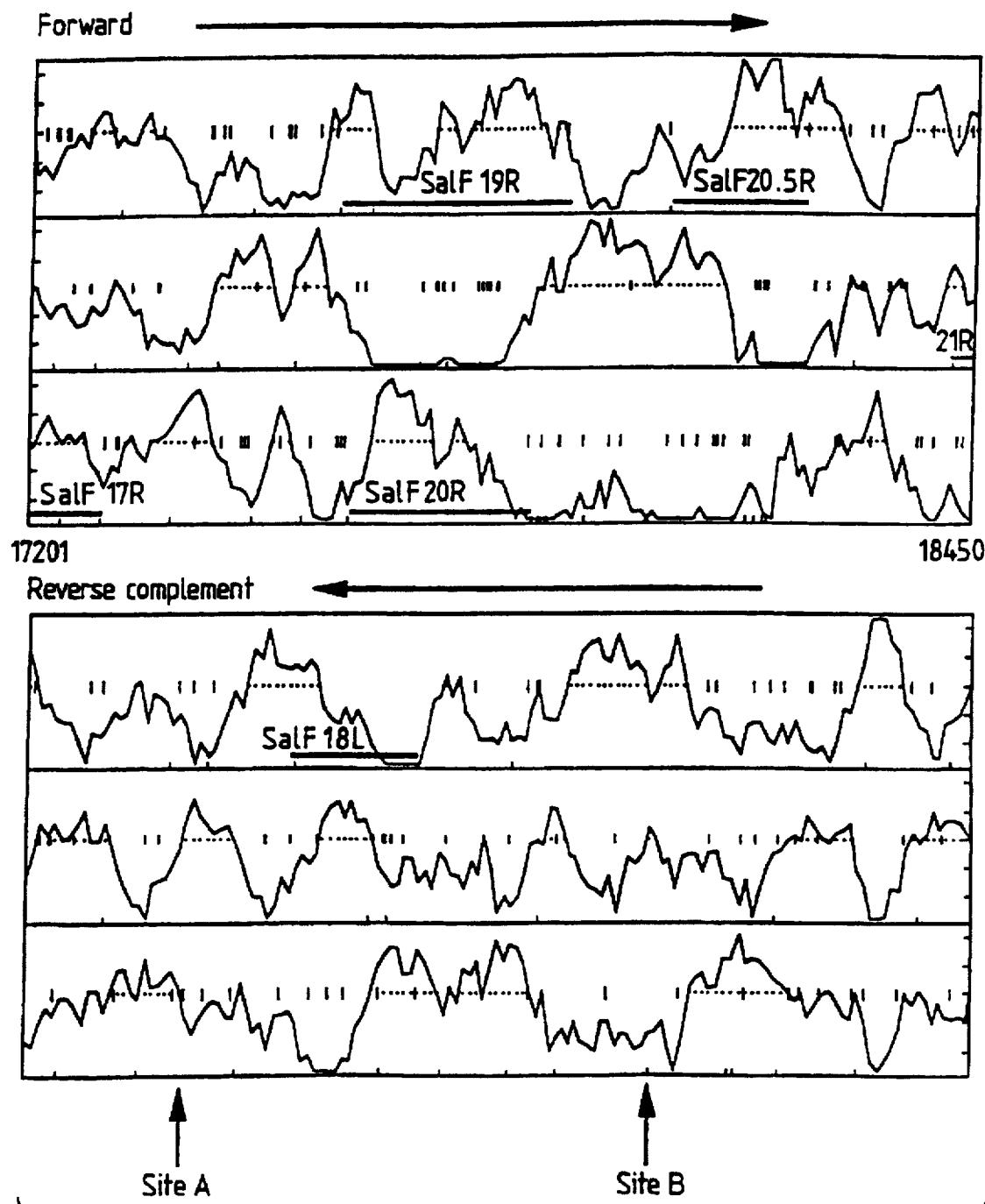
FIG._6

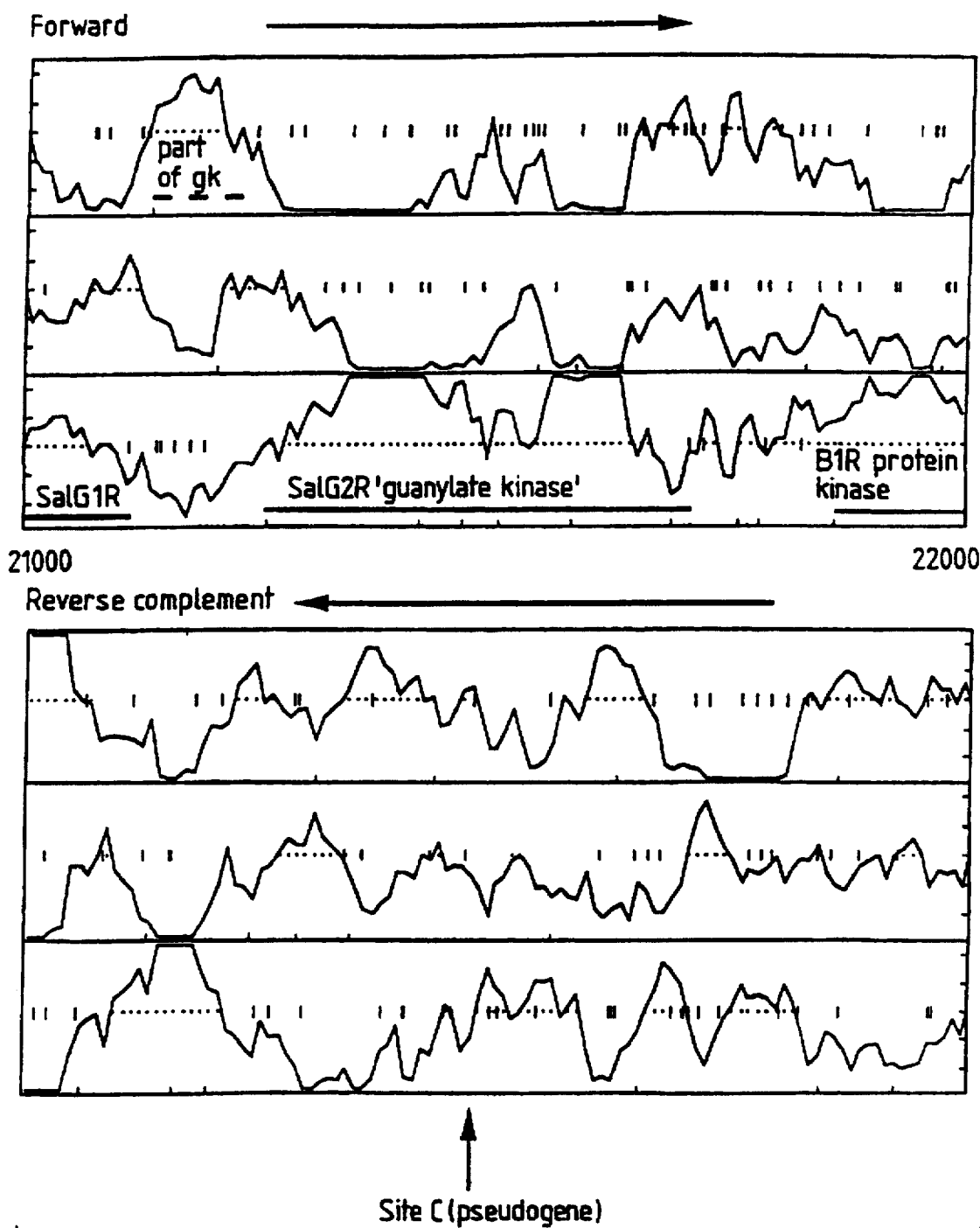
FIG._7

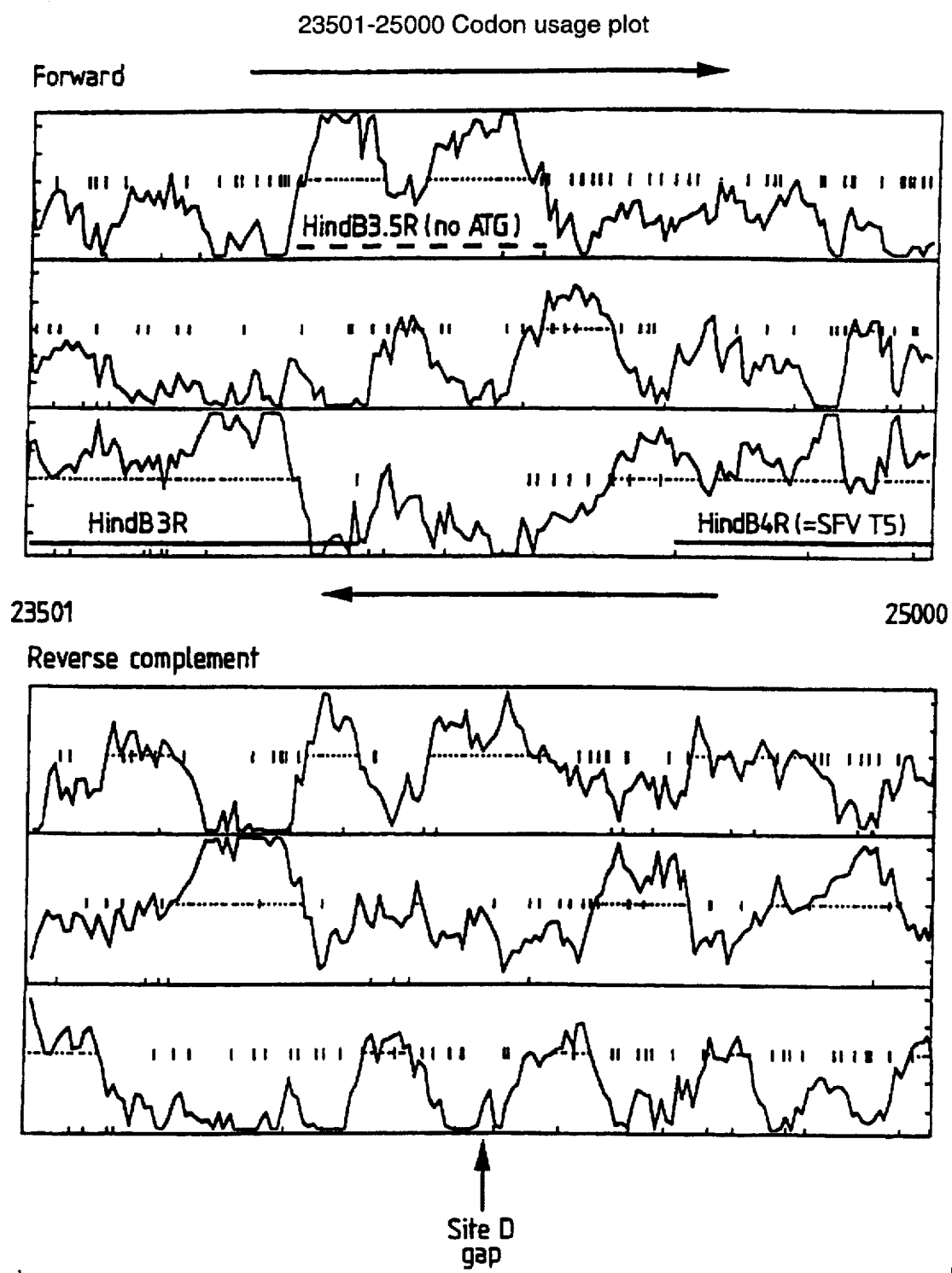
FIG._8

```
SaIF17R
GATTGTGTGCATGCCGTGGTAGATGTGTTTGGAGAATGAGAACTGTTTTCTAGATGGAAAT     501
  L  C  A  C  V  V  D  V  V  R  N  E  K  L  F  S  R  W  K  Y

ATTGTTTACGAGCTATTAAACTGTTATTAATGATCACATGCTTGATAAGATAAAATCTA     561
  I  V  Y  R  A  I  K  L  F  I  N  D  H  M  L  D  K  I  K  S  I

TACTGCAGAATAGACTAGTAGTGTGGAAATGTCATAGAAAAGTTAATGAGAGC     621
  L  Q  N  R  L  V  V  V  E  M  S  *

AAAAATATATAAGGTTGTATTCCATATTGTTATTTTTTCTGTAATAGTTAGAAAAATAC     681

Site A
ATTCGATGGTCTATCTACCAGATTATTATGTGTTATAAGGTAC TTTTTCTCATATAAAC     741

TAGAGTATGAGTAAGATAGTGTGTTTCAAAACATATAAATCTAAAATTGATGATGAGAT     801

ATACAGCTATTAATTTCGAAAATATATTTAATCTGATAACTTTAAACATGGATTTTTGA     861

SaIF19R
TGGTGGGTTTAACGTTTTAAAAAAGATTTTGTTATTGTAGTATATGATATATAAAGA     921
                                      M  I  L  K  D

TGGATATAAAGATTTGCTGACTGCCATGTACTATTTTTACATTACTACATTGGCTACGG     981
  G  Y  K  E  F  A  D  C  H  V  Y  F  L  H  Y  Y  I  G  Y  G
```

FIG._9

```
SalF20R                                                                                    1140
TGCCAAGGTTAGATGTAATGGTAACGATAACACAAAATGTGAACGCTGCCACCTCATAC
 A  K  V  R  C  N  G  N  D  N  T  K  C  E  R  C  P  P  H  T

ATATACCACAATCCCAATTATTCTAATGGATGTCATCAATGTAGAAAATGCCCAACCGGA    1200
 Y  T  T  I  P  I  L  N  D  V  I  N  V  E  N  A  Q  P  D

TCATTTGATAAGGTAAAGTGTACCGGAACACAGAACAGTAAATGTTCGTGTCTTCCTGGT    1260
 H  L  I  R  *
                        Site B
TGGTATTGTGCTACTGATTCTTCACAGACTGAAGATTGTTGAATTGTGTACCAAAAGG      1320
                                  SalF20.5R
                                  M  N  K  E  I  L  F  V  N  R AGATGTCCATGCGGATACTTTGGTGGAATAGATGAACAAGGAATCCTATTTGTAAATCG    1380
 M  N  K  E  I  L  F  V  N  R TGTTGTGTTGGTGAATATTGCGACTACCTACGTAATTATAGACTTGATCCATTTCCTCCA    1440
 V  V  L  V  N  I  A  T  T  Y  V  I  D  L  I  H  F  L  H TGCAAACTATCTAAATGTAATTATTATTATGATTTGATGATAATGTTACCATACATTATAT    1500
 A  N  Y  L  N  V  I  I  M  I  *

CGGTACTTGGTTAGTGTATTATTCAGTATGAAGACCTATTATAATTACTTATCTTTTGA    1560
 R  T  W  L  V  Y  Y  S  V  *

CGATCTTGTTATAATTATAATATAAAATACTTATGGCATAGTAACTCATAATTGCTGAC    1620
```

FIG.—10

```
          Gap Weight.       3.000         Average Match.      0.540
       Length Weight.       0.100         Average Mismatch.  -0.396

Quality.     113.0                 Length.       199
                Ratio.     0.608                   Gaps.         4
    Percent Similarity.   56.354         Percent Identity:   29.282
```

The top sequence is SoIG2R and the bottom sequence is the yeast GK

```
                                                         Start of G2R
                                                              v
  1  MSGIUKSIILSGPSGLGKTAIRKALMGIY...LDLUCPIPLDFLULMERE   47
     ..:..::::  ::... :.:... :   ......  .        :  .
  1  ....SRPIUISGPSGTGKSTLLKKLFREYPDSFGFSUSSTTRTPRRGEUM   46

48  GUDYHYUMRERIUKGIRRGMFLEMTEFLGMIYGTSKTAUMTRRIMMRICU   97
     : ::...:.  .....  : ...:.:  ..: ::.::.. ..:. .. ....:.
 47  GKDYMFUSUDEFKSMIKMMEFIEURQFSGMYYGSTURSUKQUSKSGKTCI   96

98  MDLMIDGURSLKM.TYLMPYSUYIRPTSLKMUETKLRCRMTERMDEIHRR  146
     .:......::.:.:. . : .  ..: :.:... .....  .:..:.......:
 97  LDIDMQGUKSUKRIPELMRRFLFIRPPSUEDLKKRLEGRGTETEESIMKR  146

147  UILRKTDMDERMERGLFDTIIIEDDUMLRYSKLIQ.ILQDRIRMYFMTM  194
      .  ......  :  :..:   :...:..::..  ::..:  . :....
147  LSRRQRELRYR.ETGRMDKUIUMDDLDKRYKELKDFIFREK.........  186
```

FIG._11

```
HindB3R
CTAAGAACACGTATACGGCAGCAGCTTCCTTTATACTCTCATCTTTTACCAACACAAAGG        507
  L  R  T  R  I  R  Q  Q  L  P  L  Y  S  H  L  L  P  T  Q  R GTGGATATTTGTTCATTGGAGTTGATAATAATACACACAAAGTAATTGGATTCACGGTGG        567
  V  D  I  C  S  L  E  L  I  I  I  H  T  K  *

GTCATGACTACCTCAGACTGGTAGAGAATGATATAGAAAAGCATATCAAAAGACTTCGTG        627

TTGTGCATTTCTGTGAGAAGAAAGAGGACATCAAGTACACGTGTCGATTCATCAAGGTAT        687

Site D
ATAAACCTGGGGATGAGGCTACCTCGACATACGTGTGCGCTATCAAAGTGGAAAGATGCT        747

GTTGTGCTGTGTTTGCAGATTGGCCAGAATCATGGTATATGGATACTAATGGTATCAAGA        807

AGTATTCTCCAGATGAATGGGTGTCACATATAAAATTTTAATTAATGTAATAGAGAACAA        867

ATAATAAGGTTGTAATATCATATAGACAATAACTAACAATTAATTAGTAACTGTTATCTC        927

TTTTTTAACTAACCAACTAACTATATACCTATTAATACATCGTAATTATAGTTCTTAACA        987

TCTATTAATCATTAATTCGCTTCTTTAATTTTTTATAAACTAACATTGTTAATTGAAAAG       1047
                                 HindB4R
GGATAACATGTTACAGAATATAAATTATATATGGATTTTTTTAAAAAGGAAATACTTGAC       1107
                                    M  D  F  F  K  K  E  I  L  D TGGAGTATATATTTATCTCTTCATTATATAGCACGCGTGTTTTCCAATTTTTCCACATCC       1167
  W  S  I  Y  L  S  L  H  Y  I  A  R  V  F  S  N  F  S  T  S
```

FIG._12

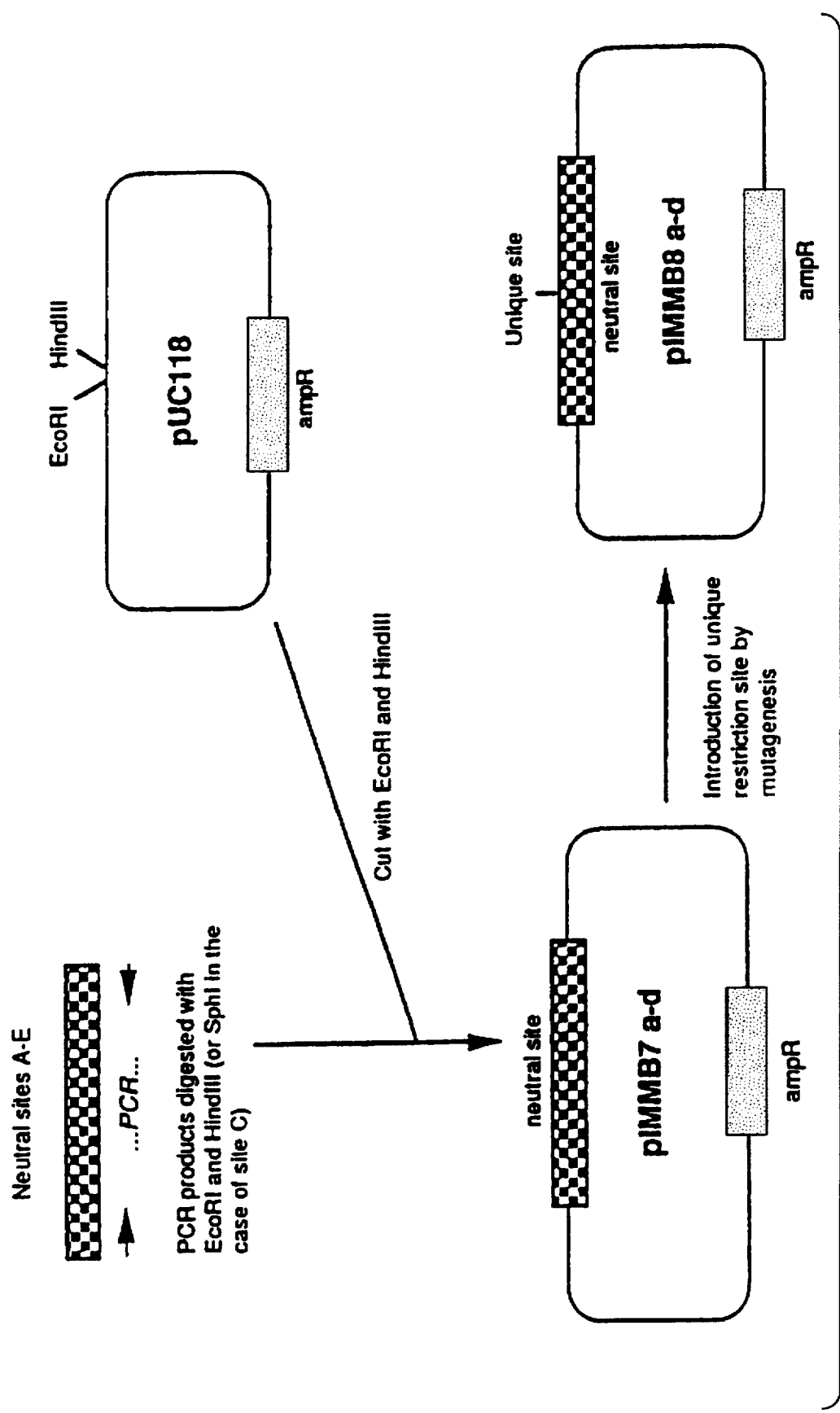
FIG._13

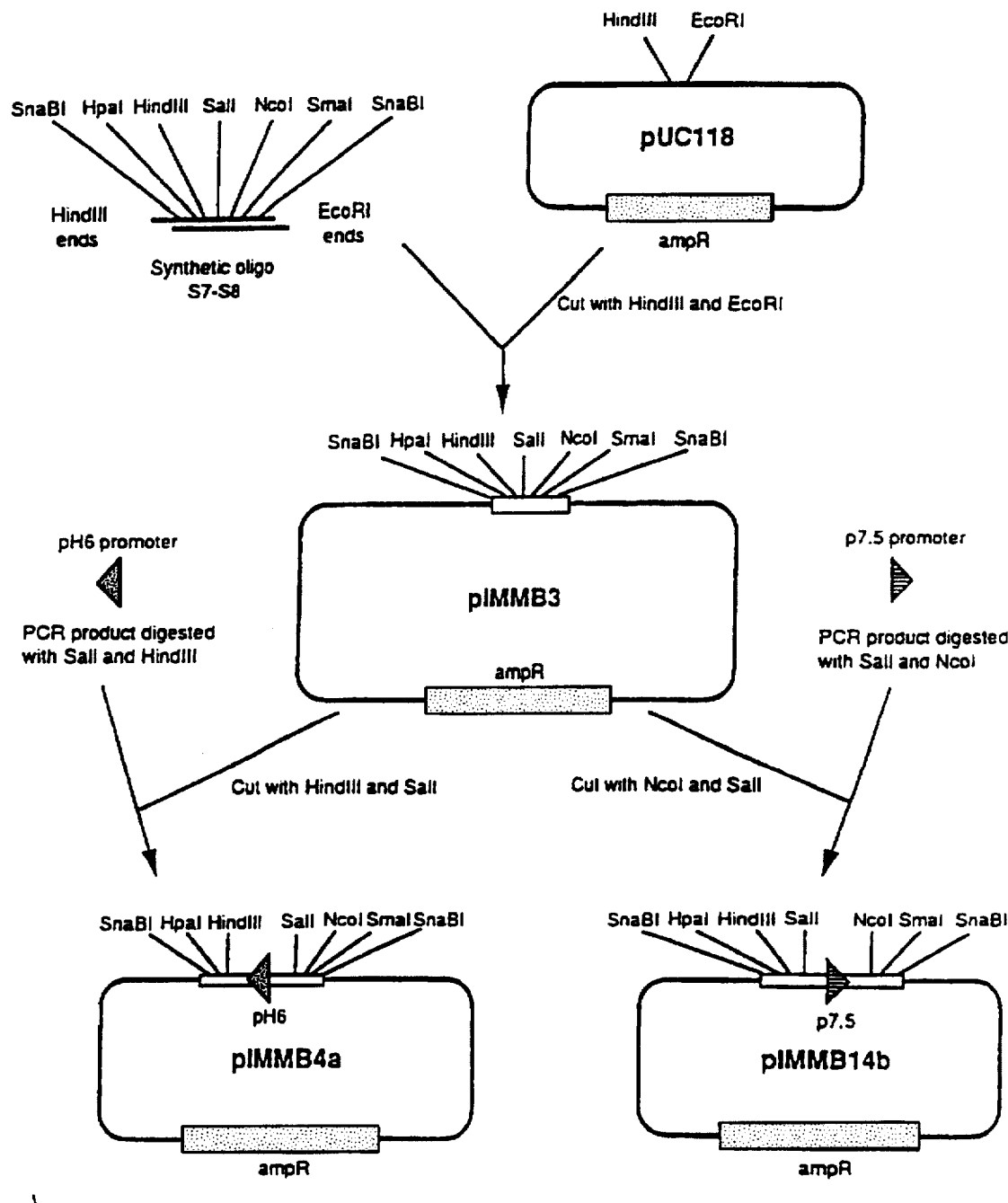
FIG._14

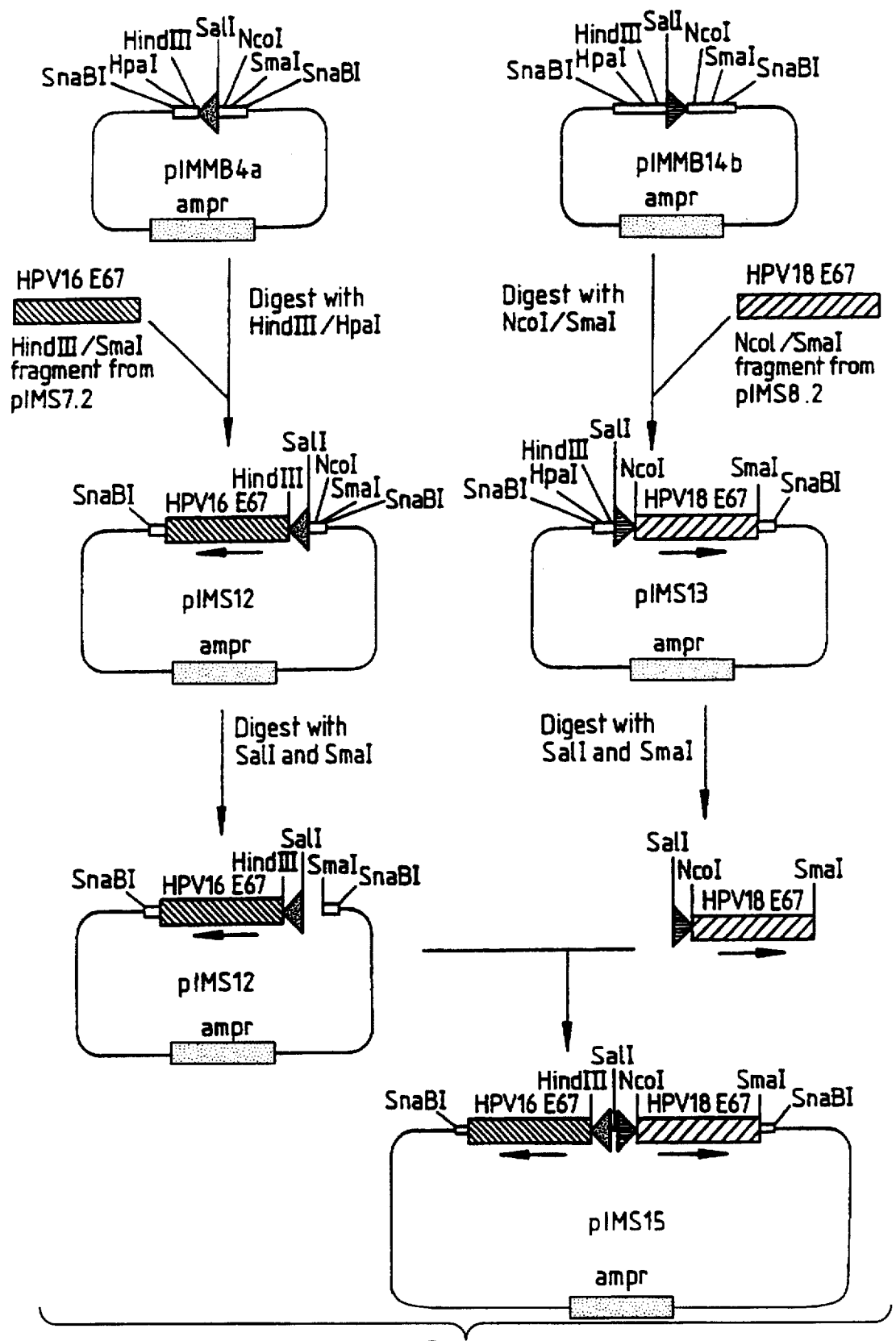
FIG._15

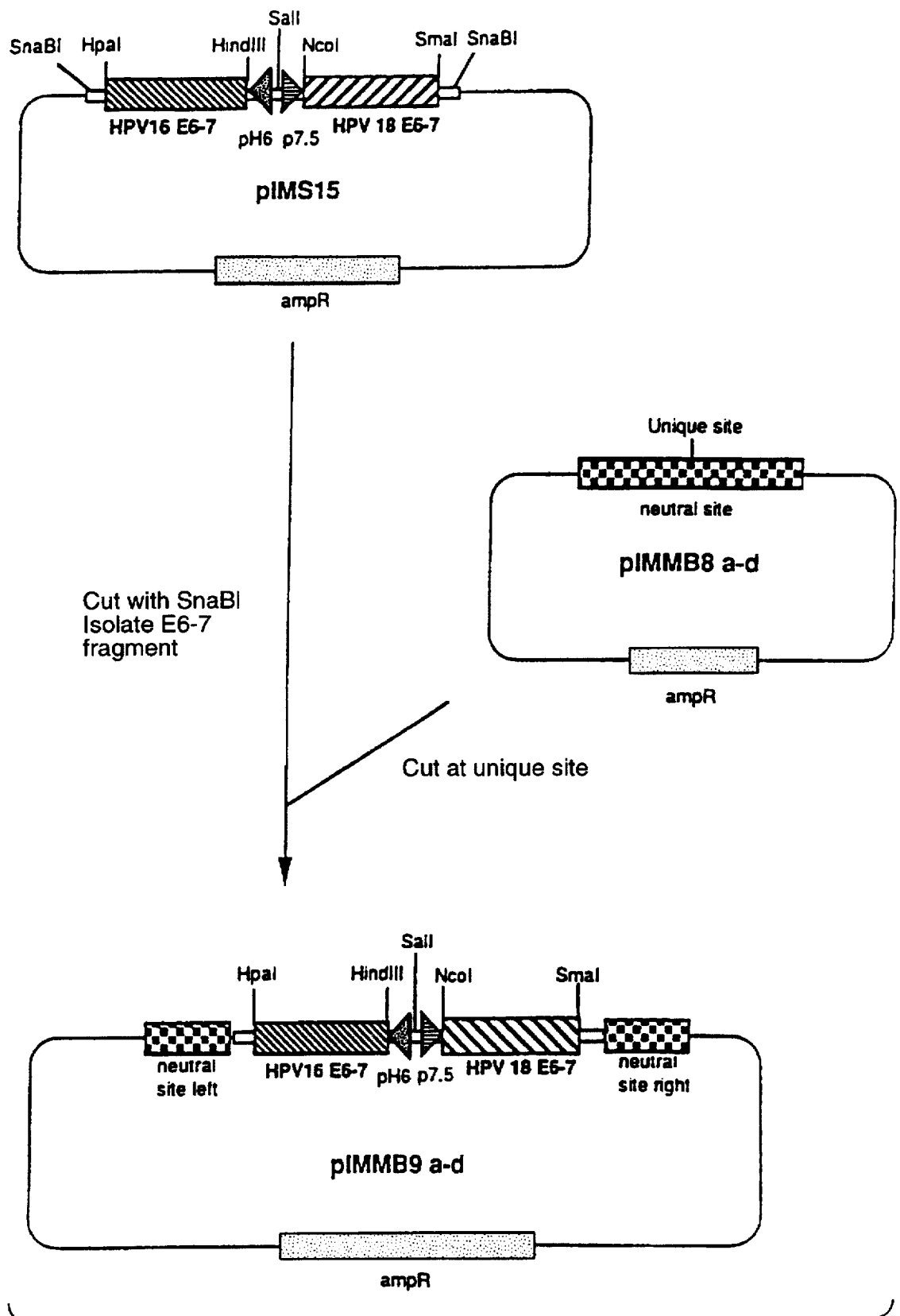
FIG._16

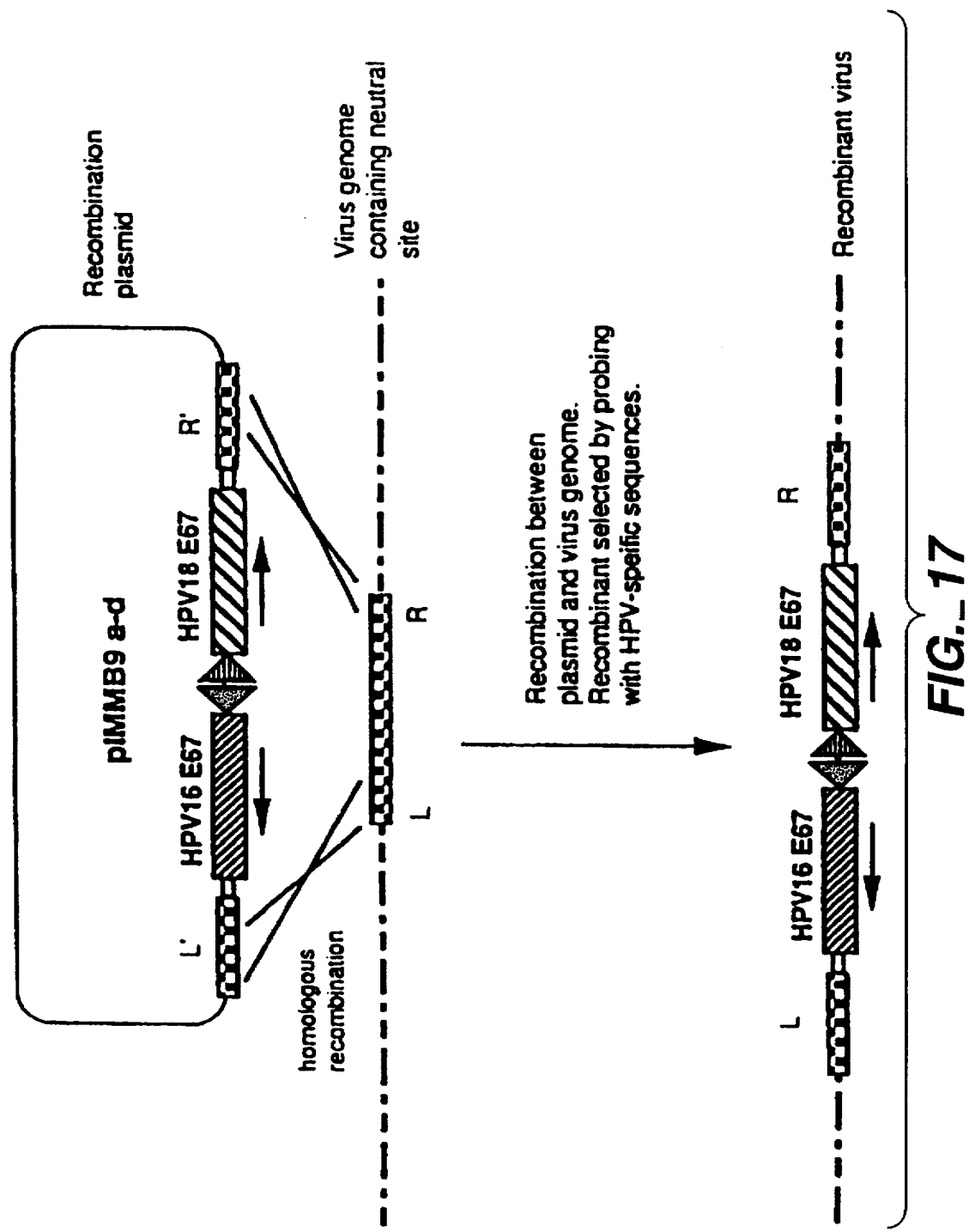
FIG._17

| | |
|---|---|
| MB03 | TCAGGATCCCACATGAGCGAAAAATACATCG |
| MB07 | TCAAAGCTTATTACGATACAAACTTAACGGA |
| MB09 | TCAGTTAACATAAAAAGAACAACGCCCGGCAG |
| MB14 | TCAAGGGCCTCTATATAGTAATACCAATACTC |
| MB15 | TCAGTCGACTTACAAACAACTAGGAAATTGG |
| MB16 | TCAGAATTCTATGTACAGAGGTCTATTAGGC |
| MB17 | TCAAAGCTTGTATGAGGTGGGCAGCGTTCAC |
| MB18 | TCAGAATTCTTAATTATATTGTCGGCCGTGG |
| MB19 | TCAGCATGCATGATCCGTTAGCTTTGGGCTC |
| MB22 | TCAGAATTCGAAGCTCTAGAGTATCTTAGCG |
| MB23 | TCAAAGCTTTCCTGTATTATATGGGATGTGG |
| MB24 | TCAGAATTCATTGATGGATGAGATATACAGC |
| MB25 | TCAAAGCTTTCACAAAATCG |
| MB26 | TCAGAATTCCACGTATACGGCAGCAGCTTCC |
| MB27 | TCAAAGCTTTGTTCTACGTCCATTTTCAAGC |
| MB32 | TCAGTCGACATACCAATACTCAAGACTACGA |
| MB33 | TCACCATGGATTGCTATTGATTGAGTACTGTTC |
| MB35 | AGTACCTTATAATACGTAATAATCTGGTAG |
| MB36 | AATCTTCAGTCTGTTAACAATCAGTAGCAC |
| MB37 | TACAACGAAGCTAGGCCTCAACCATTTTAA |
| MB38 | TTTGATAGCGCATACGTATGTCGAGGTAGC |
| MB39 | AATAGGTATATAGTTAACTGGTTAGTTAAA |
| S01 | ATCCCATGGCGCGCTTTGAGGATCCAAC |
| S02 | TCACCCGGGTTACTGCTGGGATGCACACCAC |
| S05 | ATCCCATGGACCAAAAGAGAACTGCAATGTTTC |
| S06 | TCACCCGGGTTATGGTTTCTGAGAACAGATG |
| S07 | AGCTCTACGTAGTTAACAAGCTTGTCGACCCATGGCCCGGGTACGTA |
| S08 | AATTTACGTACCCGGGCCATGGGTCGACAAGCTTGTTAACTACGTAG |
| S20 | GAAACCCAGCTGGGAATCATGCATGG |
| S21 | GAAACACAAGTAGGAATATTAAGTATG |
| S22 | GATCTCTACGGTTATGGGCAATTAAATGAC |
| S23 | GACCTTCTAGGTCACGGGCAATTAAGCGAC |
| S24 | ATGTATAGATTTCTACAGTAGAATCAGAGAATTAAG |

```
TATTGTTTACGAGCTATTAAACTGTTTATTAATGATCACATGCTTGATAAGATAAAATCT   60
  Y  C  L  R  A  I  K  L  F  I  N  D  H  M  L  D  K  I  K  S
   I  V  Y  E  L  L  N  C  L  L  M  I  T  C  L  I  R  *  N  L
    L  F  T  S  Y  *  T  V  Y  *  *  S  H  A  *  *  D  K  I  Y

ATACTGCAGAATAGACTAGTATATGTGGAAATGTCATAGAAAGTTAAAAGTTAATGAGAG   120
  I  L  Q  N  R  L  V  Y  V  E  M  S  *  K  V  K  S  *  *  E
   Y  C  R  I  D  *  Y  M  W  K  C  H  R  K  L  K  V  N  E  S
    T  A  E  *  T  S  I  C  G  N  V  I  E  S  *  K  L  M  R  A

CAAAAATATATAAGGTTGTATTCCATATTTGTTATTTTTTCTGTAATAGTTAGAAAAATA   180
  Q  K  Y  I  R  L  Y  S  I  F  V  I  F  S  V  I  V  R  K  I
   K  N  I  *  G  C  I  P  Y  L  L  F  F  L  *  *  L  E  K  Y
    K  I  Y  K  V  V  F  H  I  C  Y  F  F  C  N  S  *  K  N  T

CATTCGATGGTCTATCTACCAGATTATTATGTGTTATAAGGTACTTTTTCTCATAATAAA   240
  H  S  M  V  Y  L  P  D  Y  Y  V  L  *  G  T  F  S  H  N  K
   I  R  W  S  I  Y  Q  I  I  M  C  Y  K  V  L  F  L  I  I  N
    F  D  G  L  S  T  R  L  L  C  V  I  R  Y  F  F  S  *  *  T

CTAGAGTATGAGTAAGATAGTGTTTTTCAAAACATATAAATCTAAAATTGATGGATGAGA   300
  L  E  Y  E  *  D  S  V  F  Q  N  I  *  I  *  N  *  W  M  R
   *  S  M  S  K  I  V  F  F  K  T  Y  K  S  K  I  D  G  *  D
    R  V  *  V  R  *  C  F  S  K  H  I  N  L  K  L  M  D  E  I

TATACAGCTATTAATTTCGAAAATATATTTTAATCTGATAACTTTAAACATGGATTTTTG   360
  Y  T  A  I  N  F  E  N  I  F  *  S  D  N  F  K  H  G  F  L
   I  Q  L  L  I  S  K  I  Y  F  N  L  I  T  L  N  M  D  F  *
    Y  S  Y  *  F  R  K  Y  I  L  I  *  *  L  *  T  W  I  F  D

ATGGTGGTTTAACGTTTTAAAAAAAGATTTTGTTATTGTAGTATATGATAATATTAAAAG   420
  M  V  V  *  R  F  K  K  R  F  C  Y  C  S  I  *  *  Y  *  K
   W  W  F  N  V  L  K  K  D  F  V  I  V  V  Y  D  N  I  K  R
    G  G  L  T  F  *  K  K  I  L  L  L  *  Y  M  I  I  L  K  D

ATGGATATAAAGAATTTGCTGACTGCATGTACTATTTTTTACATTACTACATTGGCTACG   480
  M  D  I  K  N  L  L  T  A  C  T  I  F  Y  I  T  T  L  A  T
   W  I  *  R  I  C  *  L  H  V  L  F  F  T  L  L  H  W  L  R
    G  Y  K  E  F  A  D  C  M  Y  Y  F  L  H  Y  Y  I  G  Y  G

GCAGATATACCTACTCCGCCACCAACGGGTCATGTGACAAGGGAGAATATCTTGATAAGA   540
  A  D  I  P  T  P  P  P  T  G  H  V  T  R  E  N  I  L  I  R
   Q  I  Y  L  L  R  H  Q  R  V  M  *  Q  G  R  I  S  *  *  E
    R  Y  T  Y  S  A  T  N  G  S  C  D  K  G  E  Y  L  D  K  R

GGCATAATCAATGTTGTAATCGGTGTCCACCTGGAGAATTTGCCAAGGTTAGATGTAATG   600
  G  I  I  N  V  V  I  G  V  H  L  E  N  L  P  R  L  D  V  M
   A  *  S  M  L  *  S  V  S  T  W  R  I  C  Q  G  *  M  *  W
    H  N  Q  C  C  N  R  C  P  P  G  E  F  A  K  V  R  C  N  G

GTAACGATAACACAAAATGTGAACGCTGCCCACCTCATACATATACCACAATCCCAATTA   660
  V  T  I  T  Q  N  V  N  A  A  H  L  I  H  I  P  Q  S  Q  L
   *  R  *  H  K  M  *  T  L  P  T  S  Y  I  Y  H  N  P  N  Y
    N  D  N  T  K  C  E  R  C  P  P  H  T  Y  T  T  I  P  I  I
```

```
TTCTAATGGATGTCATCAATGTAGAAAATGCCCAACCGGATCATTTGATAAGGTAAAGTG    720
 F * W M S S M * K M P N R I I * * G K V
  S N G C H Q C R K C P T G S F D K V K C
   L M D V I N V E N A Q P D H L I R * S V

TACCGGAACACAGAACAGTAAATGTTCGTGTCTTCCTGGTTGGTATTGTGCTACTGATTC    780
 Y R N T E Q * M F V S S W L V L C Y * F
  T G T Q N S K C S C L P G W Y C A T D S
   P E H R T V N V R V F L V G I V L L I L

TTCACAGACTGAAGATTGTTGAAATTGTGTACCAAAAAGGAGATGTCCATGCGGATACTT    840
 F T D * R L L K L C T K K E M S M R I L
  S Q T E D C * N C V P K R R C P C G Y F
   H R L K I V E I V Y Q K G D V H A D T L

TGGTGGAATAGATGAACAAGGAAATCCTATTTGTAAATCGTGTTGTGTTGGTGAATATTG    900
 W W N R * T R K S Y L * I V L C W * I L
  G G I D E Q G N P I C K S C C V G E Y C
   V E * M N K E I L F V N R V V L V N I A

CGACTACCTACGTAATTATAGACTTGATCCATTTCCTCCATGCAAACTATCTAAATGTAA    960
 R L P T * L * T * S I S S M Q T I * M *
  D Y L R N Y R L D P F P P C K L S K C N
   T T Y V I I D L I H F L H A N Y L N V I

TTAATTATGATTTTGATGATAATGTTACCATACATTATATCGCTACTTGGTTAGTGTATT   1020
 L I M I L M I M L P Y I I S L L G * C I
  * L * F * * * C Y H T L Y R Y L V S V L
   N Y D F D D N V T I H Y I A T W L V Y Y

ATTCAGTATGAAGACCTATTAATAATTACTTATCTTTTGACGATCTTGTTATAATTATAA   1080
 I Q Y E D L L I I T Y L L T I L L * L *
  F S M K T Y * * L L I F * R S C Y N Y N
   S V * R P I N N Y L S F D D L V I I I I

TATAAAAATACTTATGGCATAGTAACTCATAATTGCTGACGCGATAAATTCGTAATAATC   1140
 Y K N T Y G I V T H N C * R D K F V I I
  I K I L M A * * L I I A D A I N S * * S
   * K Y L W H S N S * L L T R * I R N N L

TGTTTTGTTCAAATTTTTATAAGGAATCTACAGGCATAAAAATAAAAATATAATTTATAA   1200
 C F V Q I F I R N L Q A * K * K Y N L *
  V L F K F L * G I Y R H K N K N I I Y N
   F C S N F Y K E S T G I K I K I * F I I

TATACTCTTACAGCGCGCCATCATGAATAACAGCAGTGAATTGATTGCTG             1260
 Y T L T A R H H E * Q Q * I D C
  I L L Q R A I M N N S S E L I A
   Y S Y S A P S * I T A V N * L L
```

```
ATATTTGGTATTACCGCATTAATTATATTGTCGGCCGTGGCAATTTTCTGTATTACATAT     60
 I  F  G  I  T  A  L  I  I  L  S  A  V  A  I  F  C  I  T  Y
  Y  L  V  L  P  H  *  L  Y  C  R  P  W  Q  F  S  V  L  H  I
   I  W  Y  Y  R  I  N  Y  I  V  G  R  G  N  F  L  Y  Y  I  L

TATATATATAATAAACGTTCACGTAAATACAAAACAGAGAACAAAGTCTAGATTTTTGAC    120
 Y  I  Y  N  K  R  S  R  K  Y  K  T  E  N  K  V  *  I  F  D
  I  Y  I  I  N  V  H  V  N  T  K  Q  R  T  K  S  R  F  L  T
   Y  I  *  *  T  F  T  *  I  Q  N  R  E  Q  S  L  D  F  *  L

TTACATAAATGTCTGGGATAGTAAAATCTATCATATTGAGCGGACCATCTGGTTTAGGAA    180
 L  H  K  C  L  G  *  *  N  L  S  Y  *  A  D  H  L  V  *  E
  Y  I  N  V  W  D  S  K  I  Y  H  I  E  R  T  I  W  F  R  K
   T  *  M  S  G  I  V  K  S  I  I  L  S  G  P  S  G  L  G  K

AGACAGCCATAGCCAAAAGACTATGGGAATATATTTGGATTTGTGGTGTCCCATACCACT    240
 R  Q  P  *  P  K  D  Y  G  N  I  F  G  F  V  V  S  H  T  T
  D  S  H  S  Q  K  T  M  G  I  Y  L  D  L  W  C  P  I  P  L
   T  A  I  A  K  R  L  W  E  Y  I  W  I  C  G  V  P  Y  H  *

AGATTTCCTCGTCCTATGGAACGAGAAGGTGTTGATTACCATTACGTTAACAGAGAGGCC    300
 R  F  P  R  P  M  E  R  E  G  V  D  Y  H  Y  V  N  R  E  A
  D  F  L  V  L  W  N  E  K  V  L  I  T  I  T  L  T  E  R  P
   I  S  S  S  Y  G  T  R  R  C  *  L  P  L  R  *  Q  R  G  H

ATCTGGAAGGGAATAGCCGCCGGAAACTTTCTAGAACATACTGAGTTTTTAGGAAATATT    360
 I  W  K  G  I  A  A  G  N  F  L  E  H  T  E  F  L  G  N  I
  S  G  R  E  *  P  P  E  T  F  *  N  I  L  S  F  *  E  I  F
   L  E  G  N  S  R  R  K  L  S  R  T  Y  *  V  F  R  K  Y  L

TACGGAACTTCTAAAACAGCTGTGAATACAGCGGCTATTAATAATCGTATTTGTGTGATG    420
 Y  G  T  S  K  T  A  V  N  T  A  A  I  N  N  R  I  C  V  M
  T  E  L  L  K  Q  L  *  I  Q  R  L  L  I  I  V  F  V  *  W
   R  N  F  *  N  S  C  E  Y  S  G  Y  *  *  S  Y  L  C  D  G

GATCTAAACATCGACGGTGTTAGAAGTCTTAAAAATACGTACCTAATGCCTTACTCGGTG    480
 D  L  N  I  D  G  V  R  S  L  K  N  T  Y  L  M  P  Y  S  V
  I  *  T  S  T  V  L  E  V  L  K  I  R  T  *  C  L  T  R  C
   S  K  H  R  R  C  *  K  S  *  K  Y  V  P  N  A  L  L  G  V

TATATAAGACCTACCTCTCTTAAAATGGTTGAGACCAAGCTTCGTTGTAGAAACACTGAA    540
 Y  I  R  P  T  S  L  K  M  V  E  T  K  L  R  C  R  N  T  E
  I  *  D  L  P  L  L  K  W  L  R  P  S  F  V  V  E  T  L  K
   Y  K  T  Y  L  S  *  N  G  *  D  Q  A  S  L  *  K  H  *  S
```

```
GCTAACGATGAGATTCATCGTCGCGTGATATTGGCAAAAACGGATATGGATGAGGCCAAC  600
 A  N  D  E  I  H  R  R  V  I  L  A  K  T  D  M  D  E  A  N
  L  T  M  R  F  I  V  A  *  Y  W  Q  K  R  I  W  M  R  P  T
   *  R  *  D  S  S  S  R  D  I  G  K  N  G  Y  G  *  G  Q  R

GAAGCAGGTCTATTCGACACTATTATCATTGAAGATGATGTGAATTTAGCATATAGTAAG  660
 E  A  G  L  F  D  T  I  I  I  E  D  D  V  N  L  A  Y  S  K
  K  Q  V  Y  S  T  L  L  S  L  K  M  M  *  I  *  H  I  V  S
   S  R  S  I  R  H  Y  Y  H  *  R  *  C  E  F  S  I  *  *  V

TTAATTCAGATACTACAGGACCGTATTAGAATGTATTTTAACACTAATTAGAGACTTAAG  720
 L  I  Q  I  L  Q  D  R  I  R  M  Y  F  N  T  N  *  R  L  K
  *  F  R  Y  Y  R  T  V  L  E  C  I  L  T  L  I  R  D  L  R
   N  S  D  T  T  G  P  Y  *  N  V  F  *  H  *  L  E  T  *  D

ACTTAAAACTTGATAATTAATAATATAACTCGTTTTTATATGTGGCTATTTCAACGTCTA  780
 T  *  N  L  I  I  N  N  I  T  R  F  Y  M  W  L  F  Q  R  L
  L  K  T  *  *  L  I  I  *  L  V  F  I  C  G  Y  F  N  V  *
   L  K  L  D  N  *  *  Y  N  S  F  L  Y  V  A  I  S  T  S  N

ATGTATTAGTTAAATATTAAAACTTACCACGTAAAACTTAAAATTTAAAATGATATTTCA  840
 M  Y  *  L  N  I  K  T  Y  H  V  K  L  K  I  *  N  D  I  S
  C  I  S  *  I  L  K  L  T  T  *  N  L  K  F  K  M  I  F  H
   V  L  V  K  Y  *  N  L  P  R  K  T  *  N  L  K  *  Y  F  I

TTGACAGATAGATCACACATTATGAACTTTCAAGGACTTGTGTTAACTGACAATTGCAAA  900
 L  T  D  R  S  H  I  M  N  F  Q  G  L  V  L  T  D  N  C  K
  *  Q  I  D  H  T  L  *  T  F  K  D  L  C  *  L  T  I  A  K
   D  R  *  I  T  H  Y  E  L  S  R  T  C  V  N  *  Q  L  Q  K

AATCAATGGGTCGTTGGACCATTAATAGGAAAAGGTGGATTCGGTAGTATTTATACTACT  960
 N  Q  W  V  V  G  P  L  I  G  K  G  G  F  G  S  I  Y  T  T
  I  N  G  S  L  D  H  *  *  E  K  V  D  S  V  V  F  I  L  L
   S  M  G  R  W  T  I  N  R  K  R  W  I  R  *  Y  L  Y  Y  *

AATGACAATAATTATGTAGTAAAAATAGAGCCCAAAGCTA                      1020
 N  D  N  N  Y  V  V  K  I  E  P  K  A
  M  T  I  I  M  *  *  K  *  S  P  K  L
   *  Q  *  L  C  S  K  N  R  A  Q  S  S
```

```
ACCATCGAGGTAACCACCTCTCTGGAAGACAGCGTGAATAATGTACTCATGAAACGTTTG    60
 T  I  E  V  T  T  S  L  E  D  S  V  N  N  V  L  M  K  R  L
  P  S  R  *  P  P  L  W  K  T  A  *  I  M  Y  S  *  N  V  W
   H  R  G  N  H  L  S  G  R  Q  R  E  *  C  T  H  E  T  F  G

GAAACTATACGCCATATGTGGTCTGTCGTATATGATCATTTTGATATTGTGAATGGTAAA    120
 E  T  I  R  H  M  W  S  V  V  Y  D  H  F  D  I  V  N  G  K
  K  L  Y  A  I  C  G  L  S  Y  M  I  I  L  I  L  *  M  V  K
   N  Y  T  P  Y  V  V  C  R  I  *  S  F  *  Y  C  E  W  *  R

GAATGCTGTTATGTGCATACGCATTTGTCTAATCAAAATCTTATACCGAGTACTGTAAAA    180
 E  C  C  Y  V  H  T  H  L  S  N  Q  N  L  I  P  S  T  V  K
  N  A  V  M  C  I  R  I  C  L  I  K  I  L  Y  R  V  L  *  K
   M  L  L  C  A  Y  A  F  V  *  S  K  S  Y  T  E  Y  C  K  N

ACAAATTTGTACATGAAGACTATGGGATCATGCATTCAAATGGATTCCATGGAAGCTCTA    240
 T  N  L  Y  M  K  T  M  G  S  C  I  Q  M  D  S  M  E  A  L
  Q  I  C  T  *  R  L  W  D  H  A  F  K  W  I  P  W  K  L  *
   K  F  V  H  E  D  Y  G  I  M  H  S  N  G  F  H  G  S  S  R

GAGTATCTTAGCGAACTGAAGGAATCAGGTGGATGGAGTCCCAGACCAGAAATGCAGGAA    300
 E  Y  L  S  E  L  K  E  S  G  G  W  S  P  R  P  E  M  Q  E
  S  I  L  A  N  *  R  N  Q  V  D  G  V  P  D  Q  K  C  R  N
   V  S  *  R  T  E  G  I  R  W  M  E  S  Q  T  R  N  A  G  I

TTTGAATATCCAGATGGAGTGGAAGACACTGAATCAATTGAGAGATTGGTAGAGGAGTTC    360
 F  E  Y  P  D  G  V  E  D  T  E  S  I  E  R  L  V  E  E  F
  L  N  I  Q  M  E  W  K  T  L  N  Q  L  R  D  W  *  R  S  S
   *  I  S  R  W  S  G  R  H  *  I  N  *  E  I  G  R  G  V  L

TTCAATAGATCAGAACTTCAGGCTGGTGAATCAGTCAAATTTGGTAATTCTATTAATGTT    420
 F  N  R  S  E  L  Q  A  G  E  S  V  K  F  G  N  S  I  N  V
  S  I  D  Q  N  F  R  L  V  N  Q  S  N  L  V  I  L  L  M  L
   Q  *  I  R  T  S  G  W  *  I  S  Q  I  W  *  F  Y  *  C  *

AAACATACATCTGTTTCAGCTAAGCAACTAAGAACACGTATACGGCAGCAGCTTCCTTTA    480
 K  H  T  S  V  S  A  K  Q  L  R  T  R  I  R  Q  Q  L  P  L
  N  I  H  L  F  Q  L  S  N  *  E  H  V  Y  G  S  S  F  L  Y
   T  Y  I  C  F  S  *  A  T  K  N  T  Y  T  A  A  A  S  F  I

TACTCTCATCTTTTACCAACACAAAGGGTGGATATTTGTTCATTGGAGTTGATAATAATA    540
 Y  S  H  L  L  P  T  Q  R  V  D  I  C  S  L  E  L  I  I  I
  T  L  I  F  Y  Q  H  K  G  W  I  F  V  H  W  S  *  *  *  Y
   L  S  S  F  T  N  T  K  G  G  Y  L  F  I  G  V  D  N  N  T

CACACAAAGTAATTGGATTCACGGTGGGTCATGACTACCTCAGACTGGTAGAGAATGATA    600
 H  T  K  *  L  D  S  R  W  V  M  T  T  S  D  W  *  R  M  I
  T  Q  S  N  W  I  H  G  G  S  *  L  P  Q  T  G  R  E  *  Y
   H  K  V  I  G  F  T  V  G  H  D  Y  L  R  L  V  E  N  D  I

TAGAAAAGCATATCAAAAGACTTCGTGTTGTGCATTTCTGTGAAGAAAGAGGACATCA    660
 *  K  S  I  S  K  D  F  V  L  C  I  S  V  R  R  K  R  T  S
  R  K  A  Y  Q  K  T  S  C  C  A  F  L  *  E  E  R  G  H  Q
   E  K  H  I  K  R  L  R  V  V  H  F  C  E  K  K  E  D  I  K
```

FIG._21b

```
AGTACACGTGTCGATTCATCAAGGTATATAAACCTGGGGATGAGGCTACCTCGACATACG    720
  S  T  R  V  D  S  S  R  Y  I  N  L  G  M  R  L  P  R  H  T
 V  H  V  S  I  H  Q  G  I  *  T  W  G  *  G  Y  L  D  I  R
   Y  T  C  R  F  I  K  V  Y  K  P  G  D  E  A  T  S  T  Y  V

TGTGCGCTATCAAAGTGGAAAGATGCTGTTGTGCTGTGTTTGCAGATTGGCCAGAATCAT    780
  C  A  L  S  K  W  K  D  A  V  V  L  C  L  Q  I  G  Q  N  H
 V  R  Y  Q  S  G  K  M  L  L  C  C  V  C  R  L  A  R  I  M
   C  A  I  K  V  E  R  C  C  A  V  F  A  D  W  P  E  S  W

GGTATATGGATACTAATGGTATCAAGAAGTATTCTCCAGATGAATGGGTGTCACATATAA    840
  G  I  W  I  L  M  V  S  R  S  I  L  Q  M  N  G  C  H  I  *
 V  Y  G  Y  *  W  Y  Q  E  V  F  S  R  *  M  G  V  T  Y  K
   Y  M  D  T  N  G  I  K  K  Y  S  P  D  E  W  V  S  H  I  K

AATTTTAATTAATGTAATAGAGAACAAATAATAAGGTTGTAATATCATATAGACAATAAC    900
  N  F  N  *  C  N  R  E  Q  I  I  R  L  *  Y  H  I  D  N  N
 I  L  I  N  V  I  E  N  K  *  *  G  C  N  I  I  *  T  I  T
   F  *  L  M  *  *  R  T  N  N  K  V  V  I  S  Y  R  Q  *  L

TAACAATTAATTAGTAACTGTTATCTCTTTTTTAACTAACCAACTAACTATATACCTATT    960
  *  Q  L  I  S  N  C  Y  L  F  F  N  *  P  T  N  Y  I  P  I
 N  N  *  L  V  T  V  I  S  F  L  T  N  Q  L  T  I  Y  L  L
   T  I  N  *  *  L  L  S  L  F  *  L  T  N  *  L  Y  T  Y  *

AATACATCGTAATTATAGTTCTTAACATCTATTAATCATTAATTCGCTTCTTTAATTTTT   1020
  N  T  S  *  L  *  F  L  T  S  I  N  H  *  F  A  S  L  I  F
 I  H  R  N  Y  S  S  *  H  L  L  I  I  N  S  L  L  *  F  F
   Y  I  V  I  I  V  L  N  I  Y  *  S  L  I  R  F  F  N  F  L

TATAAACTAACATTGTTAATTGAAAAGGGATAACATGTTACAGAATATAAATTATATATG   1080
  Y  K  L  T  L  L  I  E  K  G  *  H  V  T  E  Y  K  L  Y  M
 I  N  *  H  C  *  L  K  R  D  N  M  L  Q  N  I  N  Y  I  W
   *  T  N  I  V  N  *  K  G  I  T  C  Y  R  I  *  I  I  Y  G

GATTTTTTTAAAAAGGAAATACTTGACTGGAGTATATATTTATCTCTTCATTATATAGCA   1140
  D  F  F  K  K  E  I  L  D  W  S  I  Y  L  S  L  H  Y  I  A
 I  F  L  K  R  K  Y  L  T  G  V  Y  I  Y  L  F  I  I  *  H
   F  F  *  K  G  N  T  *  L  E  Y  I  F  I  S  S  L  Y  S  T
```

```
CGCGTGTTTTCCAATTTTTCCACATCCCATATAATACAGGATTATAATCTCGTTCGAACA      1200
 R  V  F  S  N  F  S  T  S  H  I  I  Q  D  Y  N  L  V  R  T
  A  C  F  P  I  F  P  H  P  I  *  Y  R  I  I  I  S  F  E  H
   R  V  F  Q  F  F  H  I  P  Y  N  T  G  L  *  S  R  S  N  I

TACGAGAAAGTGGATAAAACAATAGTTGATTTTTTATCTAGGTTGCCAAATTTATTCCAT      1260
 Y  E  K  V  D  K  T  I  V  D  F  L  S  R  L  P  N  L  F  H
  T  R  K  W  I  K  Q  *  L  I  F  Y  L  G  C  Q  I  Y  S  I
   R  E  S  G  *  N  N  S  *  F  F  I  *  V  A  K  F  I  P  Y

ATTTTAGAATATGGGGAAAATATTCTACATATTTATTCTATGGATGATGCTAATACGAAT      1320
 I  L  E  Y  G  E  N  I  L  H  I  Y  S  M  D  D  A  N  T  N
  F  *  N  M  G  K  I  F  Y  I  F  I  L  W  M  M  L  I  R  I
   F  R  I  W  G  K  Y  S  T  Y  L  F  Y  G  *  C  *  Y  E  Y

ATTATAATTTTTTTTCTAGATAGAGTATTAAATATTAATAAGAACGGGTCATTTATACAC      1380
 I  I  I  F  F  L  D  R  V  L  N  I  N  K  N  G  S  F  I  H
  L  *  F  F  F  *  I  E  Y  *  I  L  I  R  T  G  H  L  Y  T
   Y  N  F  F  S  R  *  S  I  K  Y  *  *  E  R  V  I  Y  T  Q

AATCTCAGGTTATCATCATCCATAATATAAAAGAATATGTATATCAATTAGTTAATAAT      1440
 N  L  R  L  S  S  S  I  N  I  K  E  Y  V  Y  Q  L  V  N  N
  I  S  G  Y  H  H  P  L  I  *  K  N  M  Y  I  N  *  L  I  M
   S  Q  V  I  I  I  H  *  Y  K  R  I  C  I  S  I  S  *  *  *

GATCATCCAGATAATAGGATAAGACTAATGCTTGAAAATGGACGTAGAACAAGACATTTT      1500
 D  H  P  D  N  R  I  R  L  M  L  E  N  G  R  R  T  R  H  F
  I  I  Q  I  I  G  *  D  *  C  L  K  M  D  V  E  Q  D  I  I
   S  S  R  *  *  D  K  T  N  A  *  K  W  T  *  N  K  T  F  F
```

*FIG._21c*

PCR amplification reactions to confirm presence and arrangement of inserted HPV sequences in the recombinant vaccinia virus A
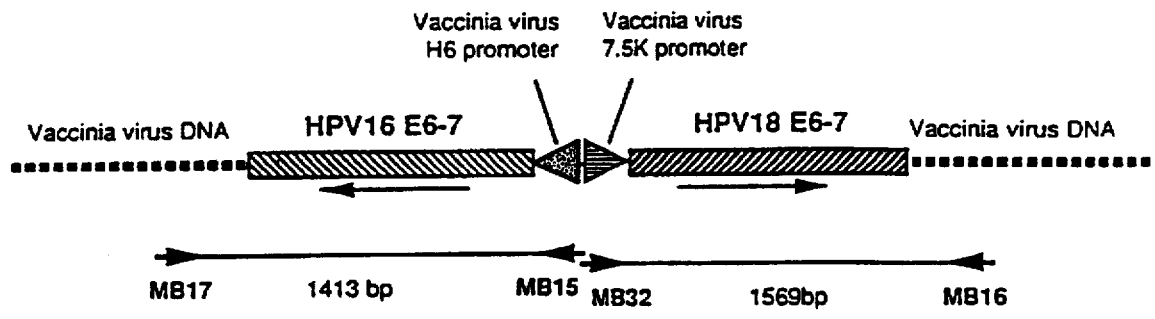
NOTE: The sequences present at the 5' end of PCR primers M15 and MB32 overlap by 6 nucleotides
FIG._22a
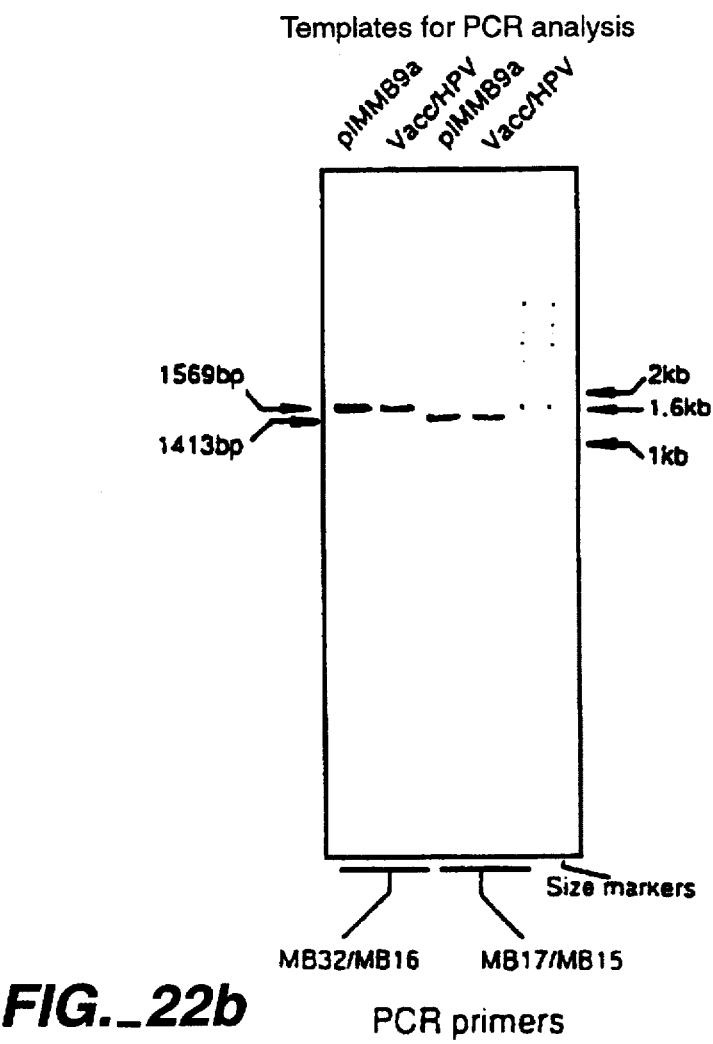
FIG._22b

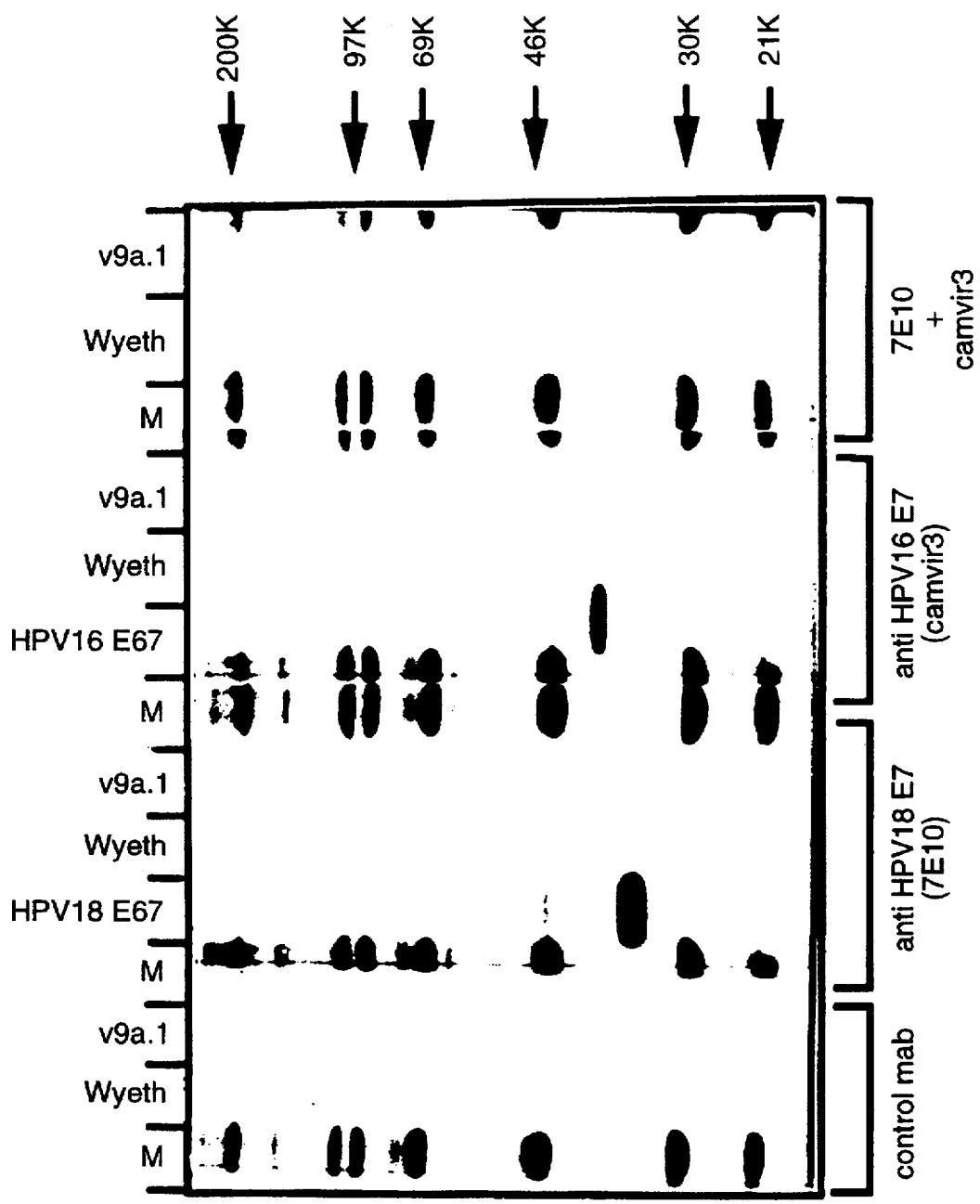
FIG._23

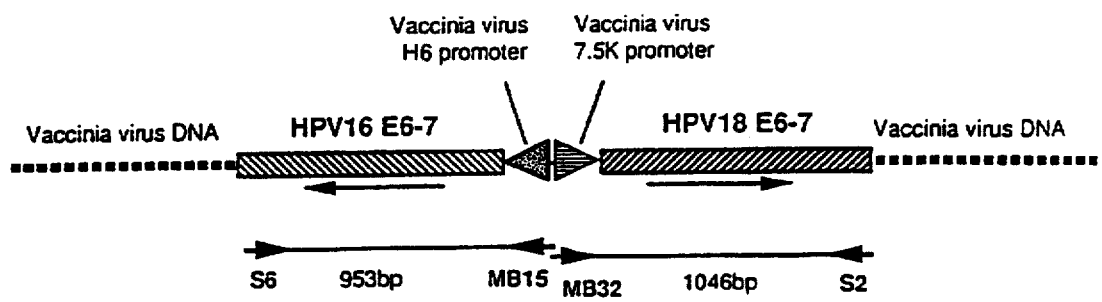
FIG._24a
| | Virus Titre ($log_{10}pfu$) | | | |
|---|---|---|---|---|
| | Experiment 1 | | Experiment 2 | |
| | Wyeth | v9a.1 | Wyeth | v9a.1 |
| 1 day | 4.02 | 4.65 | 4.11 | 2.93 |
| 3 days | 5.44 | 4.46 | 4.86 | 3.20 |
| 5 days | 4.20 | 3.76 | 3.93 | 3.26 |
FIG._25

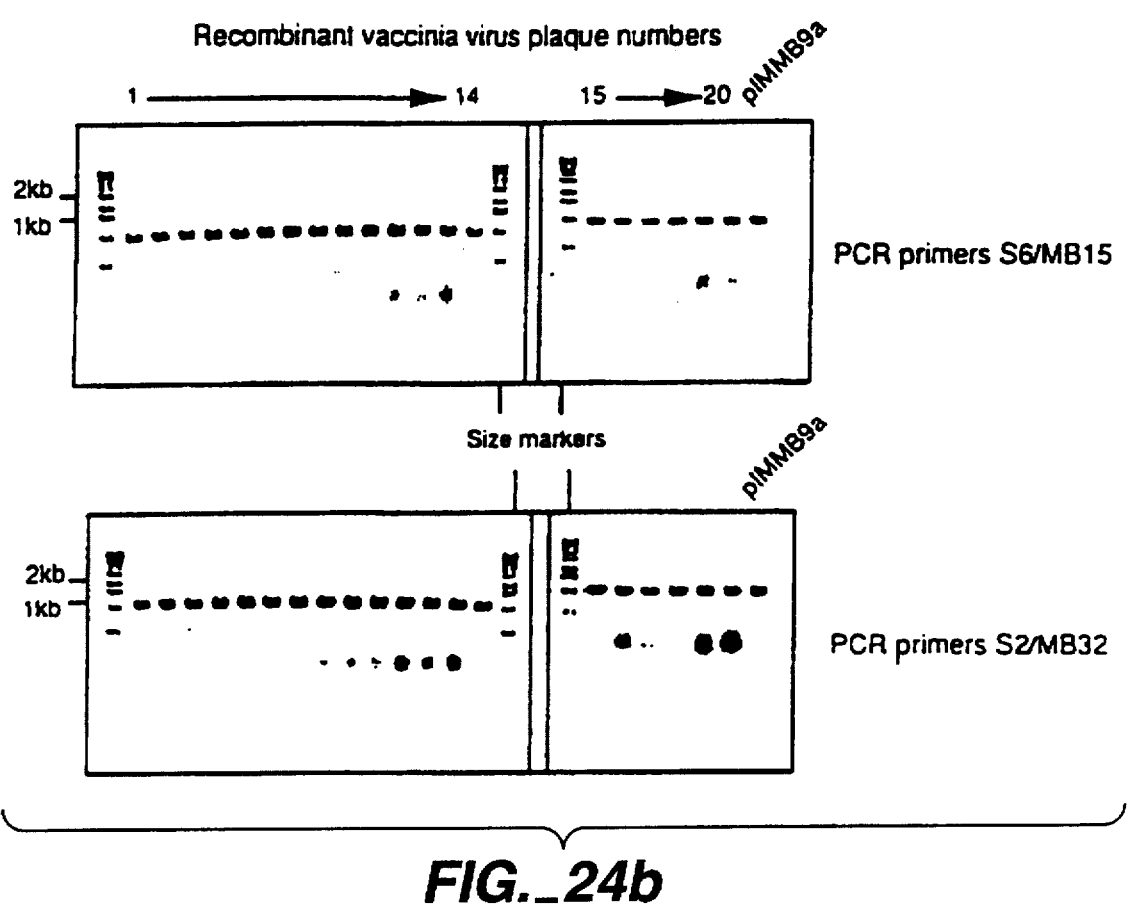
FIG._24b

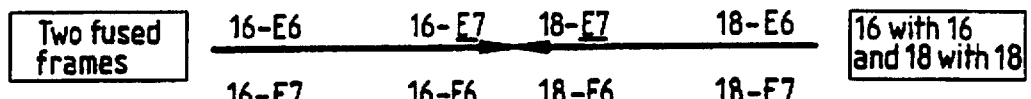
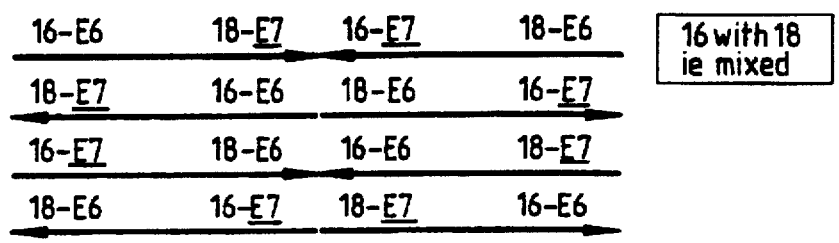
FIG._26a
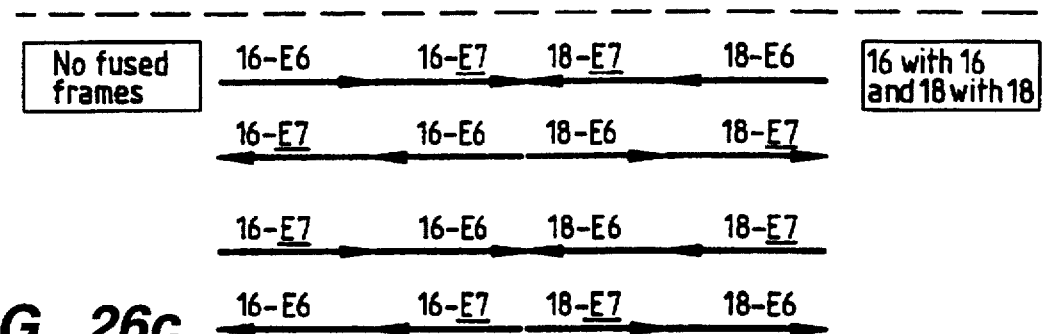
FIG._26b
FIG._26c
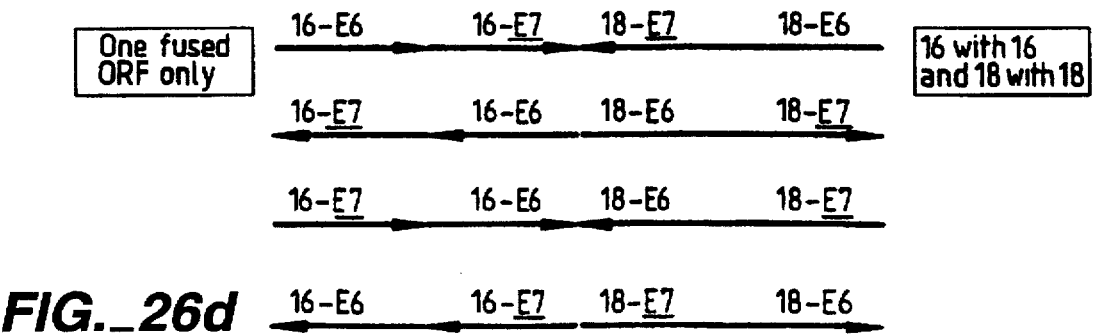
FIG._26d

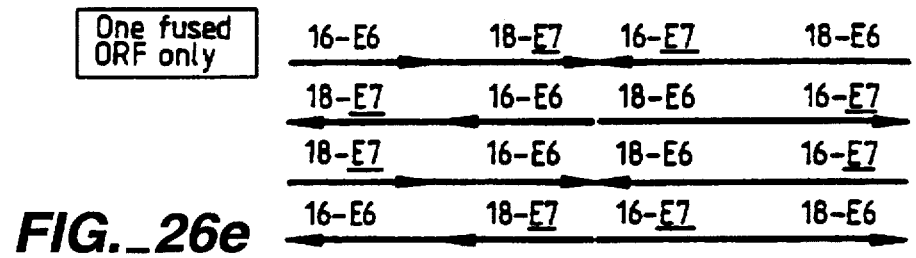
FIG._26e
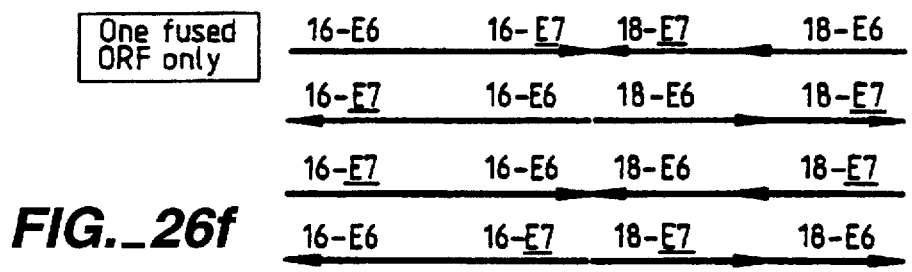
FIG._26f
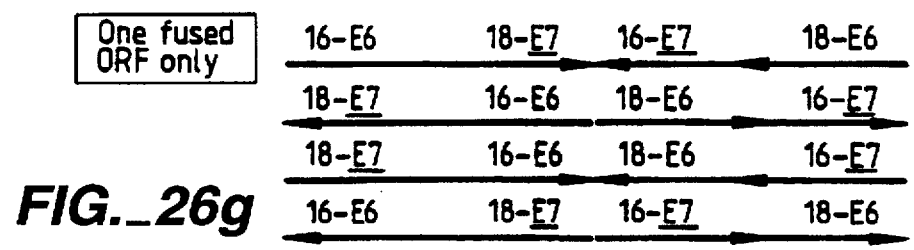
FIG._26g

RECOMBINANT VIRUS VECTORS ENCODING HUMAN PAPILLOMAVIRUS PROTEINS

FIELD OF THE INVENTION

This invention relates to recombinant virus vectors. In particular, it relates to recombinant virus vectors designed to overcome the problem of recombination between homologous nucleotide sequences. It also relates to recombinant virus vectors encoding human papillomavirus proteins; to immunotherapeutics and vaccines for conditions associated with HPV infection; to the production of a virus (e.g. vaccinia virus) engineered to express antigens encoded by human papillomavirus types 16 and 18 and to immunotherapeutics and vaccines for cervical cancer.

BACKGROUND OF THE INVENTION

In recent years, strong evidence has been adduced for a link between cervical carcinoma and infection with certain types of human papillomavirus (HPV), particularly with types 16, 18, 31, 33 and 35 (Gissman et al., Cancer Cells 5,275, 1987). This is based on hybridisation studies which have indicated that more than 85–90% of biopsies from cervical tumours can be shown to contain papillomavirus DNA. HPV16 DNA is most commonly found (in about 60% of tumours) with HPV18 the next most frequent (about 20%) and the other types accounting for a further 5–10%. In many instances, tumour cells from the biopsies do not however, contain the complete genome, but rather a deleted form. The extent and location of the deleted information within the virus genome is variable, but a general feature is the retention of the part of the genome encoding the E7 protein (Schwarz et al., Nature 314, 111, 1985). In addition, the adjacent E6-encoding region is usually present. The ubiquitous presence of the E7-encoding region in tumour cells suggests that the protein product of this gene might play a role in the induction or maintenance of the transformed phenotype. Indeed in most cell lines established from tumour biopsies, expression of the E7 gene can be detected (Smotkin & Wettstein, PNAS, 83, 4680, 1986). Furthermore, it has been shown that the E7 gene product can bind to the retinoblastoma (Rb) gene product, a recognised "anti-oncogene" in normal human cells (Munger et al., EMBO J. 8,4099, 1989). This strengthens the belief that E7 is directly involved in cell transformation.

The presence and expression of the E7 and E6 genes in tumour cells derived from cervical carcinoma biopsies, suggests the possibility that these proteins could be potential targets for the immunological recognition of the tumour cells. It is well known that viral proteins produced inside mammalian cells can be processed through a host cell pathway to short peptides, which then form a complex with host Major Histocompatibility Complex (MHC) Class 1 molecules and are transported to the cell surface. These complexes may then present a target for recognition by the host immune system. Interaction of the complex with the receptor molecule on the surface of cytotoxic T cells (the T cell receptor) can then lead to activation of the T cells to proliferate or to destroy the recognised cell. It is possible, therefore, that the presence in the body of a population of cytotoxic T lymphocytes (CTLs) which are capable of recognising cells expressing the HPV E6 and/or E7 proteins could afford protection against the development and proliferation of cervical tumours. Indeed it has been reported that normally oncogenic mouse cells engineered to express the HPV E7 protein are unable to form tumours in mice which have been previously immunised with non-tumorigenic E7-expressing cells, and that this rejection is mediated by CD8+lymphocytes (CTLs) (Chen et al., PNAS 88, 110, 1991). Further, the generation of an active population of such cells subsequent to tumour initiation could result in regression of the tumour.

There are numerous reports on the construction of recombinant viruses e.g. vaccinia viruses containing, and expressing foreign genes (Mackett & Smith, J. gen. Virol. 67,2067, 1986), and several reports of the use of these recombinant viruses to generate effective immune responses against the expressed foreign antigens. A particular advantage of this route for delivery of antigens for vaccination is that it may lead to the development of cellular as well as humoral immunity. This is because the foreign proteins will be produced inside cells of the infected individual in a manner similar to that which occurs during natural infection. This means that they should be processed through the correct pathway to allow generation of a CTL response. In several cases, it has been demonstrated directly that immunisation with the recombinant virus is capable of producing a cellular immune response in the form of foreign antigen-specific CTLs (Moss & Flexner, Ann. Rev. Immunol., 5,305, 1987). Furthermore, vaccination of animals with recombinant vaccinia viruses expressing certain tumour-specific antigens, such as the human melanoma-associated antigen P97 (Estin et al., PNAS, 85, 1052, 1988), the bovine papillomavirus E7 protein (Meneguzzi et al., Vaccine, 8, 199, 1990) and the human breast cancer-associated antigen ETA (Hareuveni et al., PNAS, 87, 9498, 1990) has been demonstrated to result in the induction of immunity against tumour initiation and progression.

SUMMARY OF THE INVENTION

The present applicants have recognised the desirability of producing a recombinant virus vector which is useful as an immunotherapeutic or vaccine for conditions caused by HPV infection, for example for cervical cancer. With respect to cervical cancer, the art at the time of the applicants making the present invention recognised the E7 gene as having the potential to immortalise cells. Therefore, it would be felt inappropriate to incorporate the E7 gene in an immunotherapeutic. The applicants however, have recognized the surprising usefulness of including the E7 gene in an immunotherapeutic. They have also recognized that the beneficial effects to be gained by treatment with an immunotherapeutic comprising the E7 gene are likely to outweigh by far any risk associated with the oncogenic activity of the E7 gene. Thus, an aspect of the applicants invention involves the use of a recombinant virus vector which expresses an E7 gene, as an immunotherapeutic or vaccine. Furthermore, the applicants provide embodiments of their invention in which these risks are reduced still further by specific alteration of the gene sequences in order to reduce the oncogenic potential of the E7 gene without compromising its ability to stimulate an appropriate immune response.

The present applicants have also recognized that where a number of HPV proteins which may be encoded by different HPV strains are implicated as being associated with a particular HPV-associated condition (for example, cervical carcinoma, HPV16 and HPV18; genital warts, condyloma acuminata, respiratory papillomatosis, HPV6 and HPV11; squamous cell carcinoma in immunosuppressed individuals, HPV5 and HPV8), rather than produce a plurality of recombinant viruses engineered separately to express each of the implicated proteins, it would be advantageous to produce a single virus recombinant which is able to express part or all of the sequences of more than one of the proteins. Thus, with respect to cervical cancer, rather than produce four recombinant viruses engineered separately to express each of the potential targets for immunological recognition of cervical tumour cells i.e. the HPV16 E6, HPV16 E7, HPV18 E6 and HPV18 E7 proteins, it would be especially advantageous to produce a single virus recombinant which is able to express the part or all of the sequences of more than one of the proteins, preferably at least two of the proteins and most preferably all four proteins. That the present applicants are able to achieve this is particularly surprising. This is because, the coding sequences for many HPV proteins are highly homologous to other equivalent HPV proteins (for example from other virus strains). Thus, the HPV16 E6 and HPV18 E6 proteins show overall homology of 62% and comprise regions of very high homology. The same is true for HPV16 E7 and HPV18 E7 which show overall homology of 57%, with particular regions of very high homology. This means that one would expect recombination to create problems such as loss of gene sequences. The applicants have, however, devised a novel strategy designed to minimise the likelihood of such recombination events and to circumvent the deleterious effect of those events should they indeed arise. Thus, surprisingly, the invention provides recombinant virus vectors which comprise at least one pair of nucleotide sequences which have sufficient sequence homology that recombination between them might be expected. The at least one pair of nucleotide sequences may encode part or all of human papillomavirus (HPV) wild-type proteins or mutant proteins immunologically cross-reactive therewith. In particular, the invention provides a recombinant vector which can maintain stably, and express, part or all of four of the desired gene sequences from HPV16 and HPV18.

Thus, the present invention provides a recombinant virus vector for use as an immunotherapeutic or vaccine which comprises at least one pair of nucleotide sequences heterologous to said virus and which have sufficient sequence homology that recombination between them might be expected wherein said pair of nucleotide sequences are arranged in said virus vector such that they are inverted with respect to each other to reduce the likelihood of recombination events leading to loss of part or all of said sequence and said virus vector is able to infect a mammalian host cell and express as polypeptide the heterologous nucleotide sequences in said host cell.

BRIEF DESCRIPTION OF THE DRAWINGS

In order that the present invention is more fully understood an embodiment will now be described in more detail with reference to the figures in which:

FIG. 1 (Parts a and b): FIG. 1(a) (SEQ ID NOS:7–10) shows the nucleotide sequence and three-frame translation of HPV16 E6/E7 polymerase chain reaction product (underlined regions indicate the E6 and E7 coding sequences); FIG. 1(b) (SEQ ID NO:11–14) shows the nucleotide sequence and three-frame translation of HPV18 E6/E7 polymerase chain reaction product (underlined regions indicate the E6 and E7 coding sequences);

FIG. 2 shows the cloning and modification of the HPV16 and HPV18 E6 and E7 Genes;

FIG. 3 shows an open reading frame plot of vaccinia virus from positions 17201–18450 of the region covered by the four fragments SalF,G,H and I; short vertical lines denote termination codons, lines topped with boxes denote initiation codons, rectangles show relevant open reading frames, and arrows show direction of upper and lower DNA strands;

FIG. 4 shows an open reading frame plot of vaccinia virus from positions 21001–22000 of the region covered by the four fragments SalF,G,H and I; short vertical lines denote termination codons, lines topped with boxes denote initiation codons, rectangles show relevant open reading frames and arrows show direction of upper and lower DNA strands;

FIG. 5 shows an open reading frame plot of vaccinia virus from positions 23501–25000 of the region covered by the four fragments SalF,G,H and I; short vertical lines denote termination codons, lines topped with boxes denote initiations codons, rectangles show relevant open reading frames and arrows show the direction of upper and lower strands of DNA;

FIG. 6 shows a codon usage plot of vaccinia virus from positions 17201–18450 of the region covered by the four fragments SalF,G,H and I; arrows show direction of each DNA strand;

FIG. 7 shows a codon usage plot of vaccinia virus from positions 21001–22000 of the region covered by the four fragments SalF,G,H and I; arrows show direction of each DNA strand;

FIG. 8 shows a codon usage plot of vaccinia virus from positions 23501–25000 of the region covered by the four fragments SalF,G,H and I; arrows show direction of each DNA strand;

FIG. 9 (SEQ ID NOS:15–17) shows the DNA sequence around site A showing translations in single letter amino acid code of genes SalF 17R and SalF 19R;

FIG. 10 (SEQ ID NOS:18–20) shows the DNA sequence around site B showing translations in single letter amino acid code of genes SalF 20R and SalF20.5R;

FIG. 11 (SEQ ID NOS:21–22) shows a comparison of the SalG2R open reading frame to the yeast guanylate kinase gene sequence;

FIG. 12 (SEQ ID NOS:23–25) shows the DNA sequence around site D showing translations in single letter amino acid code of genes HindB3R and Hind B4R;

FIG. 13 shows the cloning of vaccinia virus (Wyeth strain) neutral sites;

FIG. 14 shows the cloning of vaccinia virus promoter sequences;

FIG. 15 shows the construction of vaccinia promoter-driven E6-7 cassette;

FIG. 16 shows the cloning of the E6-7 cassette into vaccinia virus (Wyeth strain) neutral sites;

FIG. 17 is a diagram showing the recombination required to generate the final therapeutic vaccinia virus—HPV recombinant virus;

FIG. 18 (SEQ ID NOS:26–58) shows the synthetic oligonucleotides used in the construction of the therapeutic vaccinia virus HPV recombinant;

FIGS. 19a and 19b show (SEQ ID NOS:59–62) the nucleotide sequence of vaccinia virus (WR strain) from positions 17201–18450 of the region covered by the four fragments SalF,G,H and I;

FIGS. 20a and 20b show (SEQ ID NOS:63–66) the nucleotide sequence of vaccinia virus (WR strain) from positions 21001–22000 of the region covered by the four fragments SalF,G,H and I;

FIGS. 21a, 21b and 21c show (SEQ ID NOS:67–70) the nucleotide sequence of vaccinia virus (WR strain) from positions 23501–25000 of the region covered by the four fragments SalF,G,H and I.

FIG 22a shows the DNA fragments expected when the HPV DNA cassette is inserted at Site A (as marked on FIGS. 3 and 6) of recombinant vaccinia virus (V9a.1) and FIG. 22b depicts the PCR results;

FIG. 23 depicts Western blot analyis for the presence of HPV E67 fusion protein expressed by recombinant virus vector;

FIG. 24a shows the PCR amplification reaction to confirm presence and arrangment of the inserted HPV sequences and FIG. 24b depicts the PCR results;

FIG. 25 shows standard vaccina virus plaque assay results which shows that the recombinant virus retains the ability to replicate mice; and FIGS. 26a, 26b, 26c, 26d, 26e, 26f, and 26g show a variety of options for arrangment of HPV16E6 and E7 and HPV18E6 and E7 coding sequences in a recombinant virus vector.

The at least one pair of nucleotide sequences may encode part or all of human papillomavirus (HPV) wild-type proteins or mutant proteins immunologically cross-reactive therewith. The pair of nucleotide sequences may encode part or all of the protein E7 from both HPV16 and HPV18 or functional equivalents thereof. The pair of nucleotide sequences may encode part or all of the proteins E6 from both HPV16 and HPV18 or functional equivalents thereof.

The recombinant virus vector may comprise a further pair of nucleotide sequences heterologous to said virus and which (i) have sufficient sequence homology that recombination between them might be expected wherein said further pair of nucleotide sequences are arranged in said virus vector such that they are inverted with respect to each other and said virus vector is able to infect a mammalian host cell and express as polypeptide the further pair of heterologous nucleotide sequences in said host cell.

The further pair of nucleotide sequences may encode part or all of HPV wild-type proteins or mutant proteins immunologically cross-reactive therewith.

For example, the present invention also provides a recombinant virus vector which in addition to the E7 coding sequences, also comprises and is adapted to express genetic sequences encoding part or all of the protein E6 from both HPV16 and HPV18 or functional equivalents thereof. The genetic sequences may comprise sequences encoding HPV16 E6/E7 and HPV18 E6/E7 as shown in FIGS. 1(a) (SEQ ID NOS:7–10) and 1(b) (SEQ ID NOS:11–14) respectively.

The genetic sequences may encode an antigenic moiety of the said proteins.

Either or both of the nucleotide sequences in a pair of nucleotide sequences may be altered to make them less homologous than an equivalent pair of nucleotide sequences encoding wild-type HPV proteins. The alteration in nucleotide sequence may be in an area of high sequence homology Preferably, the alteration in nucleotide sequence will not result in an alteration of the encoded amino acid sequence.

Two or more nucleotide sequences each encoding separate proteins may be fused together to form a single open reading frame. Thus the genetic sequences encoding part or all of the proteins E6 and E7 from HPV16, may be fused together to form a single open reading frame. The genetic sequences encoding part or all of the proteins E6 and E7 from HPV18, may be fused together to form a single open reading frame. The genetic sequences encoding part or all of the proteins E6 and E7 from both HPV16 and HPV18, may be fused together to form a single open reading frame. Thus, the recombinant virus vector may have the pairs of nucleotide sequences arranged according to any one of the options shown in FIG. 26. Where the recombinant virus vector comprises an open reading frame having a fused genetic sequence encoding part or all of the proteins E6 and E7 from HPV16, and a separate open reading frame having fused genetic sequences encoding part or all of the proteins E6 and E7 from HPV18, the two open reading frames may be inverted with respect to one another. For example, the two open reading frames may be arranged in the recombinant virus vector adjacent to each other. The inversion may be such that the E6 coding sequences of HPV16 and HPV18 are both located between the E7 coding sequences of HPV16 and HPV18. Alternatively, the inversion could be such that the E7 coding sequences of HPV16 and HPV18 are both located between the E6 coding sequences of HPV16 and HPV18. In particular the two open reading frames, each with its respective promoter, may be arranged next to each other in the recombinant vector. In this case the promoters may be located between the genes, which are transcribed outwardly, or the promoters may be located outside the genes, which are transcribed inwardly.

Similarly, the genetic sequences encoding part or all of the E7 protein from HPV16 and the E7 protein from HPV18 may be fused together to form a single open reading frame. The genetic sequences encoding part or all of the E6 protein from HPV16 and the E6 protein from HPV18 may be fused together to form a single open reading frame. This leads to another range of arrangements similar to those shown in FIG. 26. The fusions may be via a single codon encoding a relatively small neutral amino acid e.g. glycine.

Thus the present invention also provides a recombinant virus vector which comprises a first open reading frame having a fuse genetic sequence encoding part or all of the wild-type proteins E6 and E7 from HPV16; and a separate second open reading frame having a fused genetic sequence encoding part or all of the wild-type proteins E6 and E7 from HPV18; wherein the first and second open reading frames may be inverted with respect to one another whereby either: i) the E6 coding sequences of HPV16 and HPV18 are both located between the E7 coding sequences of HPV16 and HPV18; or ii) the E7 coding sequences of HPV16 and HPV18 are both located between the E6 coding sequences of HPV16 and HPV18; and wherein any of said wild-type proteins may be replaced by a mutant protein immunologically cross-reactive therewith.

Each of the first and second open reading frames may have a corresponding promoter and the two open reading frames each with its promoter, are arranged next to each other in the virus.

The present invention also provides a recombinant virus vector wherein either: i) the promoters are located between the first and second reading frames whereby the open reading frames are transcribed outwardly; or ii) the promoters are located outside the first and second open reading frames whereby the open reading frames are transcribed inwardly.

The present invention also provides a recombinant virus vector which comprises a first open reading frame having a fused genetic sequence encoding part or all of the wild-type proteins E6 and E7 from HPV16; and a separate second open reading frame having a fused genetic sequence encoding part or all of the wild-type proteins E6 and E7 from HPV18; wherein the E6 coding sequences of HPV16 and HPV18 are both located between the E7 coding sequences of HPV16 and HPV18; and each open reading frame has a corresponding promoter, the promoters being located between the first and second open reading frames whereby the open reading frames are transcribed outwardly; and wherein any of said wild-type proteins may be replaced by a mutant protein immunologically cross-reactive therewith.

The wild-type proteins HPV16E7 and HPV18E7 may be replaced with mutant proteins which are substantially homologous to said wild-type proteins and in which the residues cys 24 and glu 26 of wild-type protein HPV16E7 and the residues cys 27 and glu 29 of wild-type protein HPV18E7 are replaced with glycine residues.

The recombinant virus vector may be derivable from vaccinia virus.

The applicants have also recognized that for effective function as an immunotherapeutic, it is desirable for the recombinant virus to retain its ability to replicate and thereby generate an active infection in order that a cellular immune response may be mounted against the virus-encoded proteins. Thus, the applicants propose that the foreign gene sequences should be inserted into the vector virus at sites, the disruption of which by the insertion of the heterologous gene sequences will not substantially interfere with, and therefore have a substantially adverse affect on any viral functions which relate to the replicative ability of the virus in the infected host animal. The applicants have named these sites 'neutral sites' (although the term 'neutral' should not be interpreted strictly as it is acknowledged that the disruption of these sites may have a small, but relatively speaking inconsequential adverse affect on replicative ability).

DNA sequences which affect virus replication can fall into several categories:

i) protein coding sequences;

ii) elements involved in control of gene expression; and iii) elements involved in virus DNA replication A non-essential and neutral insertion site must therefore avoid such regions, and, such sites have been identified on the basis of nucleotide sequencing studies. Thus the genetic sequences may be inserted into neutral sites within the virus genome. One or more genetic sequences may be inserted into the same neutral site.

Neutral sites can be easily tested for according to techniques well known in the art. For example, a site may be selected, interrupted or deleted using standard methodologies and the resultant recombinant virus placed in conditions which normally support growth of the wild type virus vector, to assess the effect of the manipulations. The pathogenicity of the virus may be further compared with that of the unmodified virus vector strain in animal models, in order to assess its level of attenuation.

In the present invention, the virus vector may be vaccinia virus. The vaccinia virus may be attenuated or disabled so that it is unable to fully replicate and establish an extensive infection of host cells.

Vaccinia virus has been used extensively in the past for vaccination against smallpox, and its use worldwide has led to the complete eradication of the disease (Bhebehami, Microbiol. Rev., 47, 455, 1983). During the World Health Organisation (WHO) campaign to eradicate smallpox, several different strains of vaccinia virus were used as vaccines. In 1984 a meeting was sponsored by the WHO to discuss the use of vaccinia virus as live virus vectors (Bulletin of the WHO 63(3): 471–477). The data in this report indicates that the number of complications associated with vaccination was lowest for the Wyeth strain of vaccinia virus, and so this strain has been chosen as a basis for the construction of the recombinant virus according to an embodiment of the present invention.

It is well known that insertion of foreign DNA into the genome of vaccinia virus at certain favoured sites, such as the thymidine kinase gene locus, can reduce dramatically the ability of the virus to replicate in vivo. As discussed above, the aim of the therapeutic approach described here is to generate an active in vivo infection, so that a cellular immune response may be mounted against the virus encoded proteins. The present invention provides a method for inserting foreign genes at neutral sites within the genome of a virus, the disruption of which sites by the insertion will not interfere with and therefore have a substantially adverse affect on virus replication.

Where the virus is vaccinia virus, the neutral site may be identified herein within the Wyeth strain of vaccinia virus on the basis of the related WR strain nucleotide sequence. Alternatively, where other vaccinia virus strains are used, sites equivalent to those sites identified above may be used. The neutral sites may be any as identified hereinafter as A (SEQ ID NO:03), B (SEQ ID NO:04), C (SEQ ID NOS:05), and D (SEQ ID NO:06), or a functional equivalent.

For successful expression of foreign proteins by the recombinant virus vector the foreign genes must be placed under the control of a promoter sequence which is operable by the virus. Thus the recombinant virus vector may comprise a single promoter which controls the expression of all the heterologous genetic sequences within a single open reading frame. Alternatively, where the recombinant virus vector encodes more than one open reading frame containing heterologous genetic sequences, the virus may comprise a first promoter which controls the expression of the genetic sequences from a first open reading frame, and one or more further promoters which control the expression of the genetic sequences from one or more further open reading frames. The promoter sequence may be virus—specific and several have been characterised so far (Davison & Moss, J. Mol. Biol., 210, 749, 1989; Davison & Moss, J. Mol. Biol., 210, 771, 1989). The single promoter and the first and one or more further promoters may be the p 7.5 promoter. There have been reports that the induction of foreign antigen-specific CTLs requires expression of the antigen early in the virus replication cycle (Coupar et al., Eur. J. Immunol., 16, 1479, 1986). Therefore, a recombinant virus as provided by the present invention may involve the use of the p7.5 promoter (Venkatesan et al., Cell, 125, 805, 1981) and/or the H6 promoter (Rosel et al., J. Virol. 60, 436, 1988), both of which are active both early and late in infection.

As mentioned earlier, it has been reported that the E7 gene on its own has the potential to immortalise cells (Phelps et al., Cell 53, 539, 1988). In an embodiment of the present invention, the strategy for expression of the protein involves production of E7 as a fusion protein with E6, which is unlikely to retain biological function. Embodiments of the invention provide for reducing this risk still further, by making changes within the E7 gene which are known to destroy its oncogenic capacity (Chesters et al., J. Gen Virol. 71, 449. 1990). Thus in the recombinant virus vectors of the present invention, the genetic sequences encoding part or all of the E7 proteins may be altered from the equivalent wild type sequences, in order to render the sequences, used in the recombinant virus vectors less oncogenic than their equivalent wild type sequences.

The present invention also provides pharmaceuticals comprising recombinant virus vectors as herein defined. The pharmaceutical may be for use against a condition caused by HPV infection which comprises an immunotherapeutically effective amount of a recombinant virus vector. The pharmaceutical may be for use against cervical cancer.

The pharmaceutical may be a vaccine to immunise against a condition caused by HPV infection which comprises an amount of recombinant virus vector as herein provided which when administered to a recipient can specifically activate cells of the immune system to HPV proteins. The vaccine may be for immunisation against cervical cancer.

The pharmaceuticals may comprise one or more excipients. The present invention also provides methods of using the recombinant virus vectors as herein defined to make medicaments for use as immunotherapeutics or vaccines against conditions thought to be caused by HPV infection. For example for the prophylaxis and treatment of cervical cancer.

The present invention also provides methods of treating mammalian patients with recombinant virus vectors and pharmaceuticals as herein provided.

The present invention also provides a method of determining a neutral site in a virus vector, the disruption of which by the insertion of heterologous gene sequences will not interfere with, and therefore, have a substantially adverse affect on viral function which relates to the replicative ability of the virus. The method for this determination comprises: (a) analysing a viral genome to identify open reading frames which are likely to encode functional genes, by looking for expected codon usage between spaced apart start and stop codons; and (b) selecting sites which are not in such open reading frames, likely to encode functional genes, as identified in (a) This may include selecting sites between open reading frames for sequences of functional genes and selecting sites which are in open reading frames which have some functional gene characteristics, such as an expected codon usage, but have lost other essential characteristics such as a start codon. The method may also comprise interrupting or deleting the selected sites from the viral genome and placing the resultant virus in conditions which normally support growth of the wild type virus.

The present invention also provides neutral sites identified by use of the above methods.

The present invention provides an embodiment which shows a way of inducing a cellular immune response against the papillomavirus proteins usually expressed in cervical tumour cells by the creation of a recombinant vaccinia virus, which has been engineered to produce the HPV E6 and E7 proteins, or proteins containing HPV E6 and E7 sequences, during its replication cycle. This therapeutic vaccinia virus contains the E6 and E7 genes from both HPV16 and HPV18, the viruses most commonly associated with cervical carcinoma. Vaccination with this single virus may thus stimulate immunity to the E6 and E7 proteins of the HPV types associated with more than 80% of cervical tumours. Expression of all four gene sequences (e.g. HPV16 E6 and E7; HPV18 E6 and E7) in a single virus however presents a problem, because of the likelihood of loss of genetic sequences through recombination. The present invention provides a method for circumventing this difficulty, firstly through specific sequence alteration, in order to reduce sequence homology and secondly through their insertion into the vaccinia virus genome in such a way that if such recombination were to occur, it would not lead to loss of sequences (i.e. in inverted orientation with respect to each other). Expression of the desired four gene sequences in the vaccinia virus genome could also be difficult (though not impossible) to achieve as independent expression units, and so the invention provides that instead, the E6 and E7 open reading frames may be fused together. A problem with standard methods for insertion of foreign information into the vaccinia virus genome is that the use of selectable markers to increase the efficiency of recombination results in the ultimate presence in the recombinant virus also of the selectable marker gene itself. Methods for insertion have been developed however, which allow subsequent elimination of these extraneous sequences (Falkner & Moss J. Virol., 64, 3108, 1990) and these are used in an embodiment of the present invention to ensure that the final recombinant vaccinia virus has only those additional sequences which are necessary for its required function.

All cloning procedures are carried out according to the protocols described in "Molecular Cloning", A Laboratory Manual, eds. Sambrook, Fritsch and Maniatis, Cold Spring Harbor Laboratory Press, 1989. All plasmids on which site directed mutagenesis is performed are of the "phagemid" type, which may be converted to single-stranded DNA by superinfection with the bacteriophage f1. Preparation and site directed mutagenesis of single-stranded DNA, is carried out as described by Brierley et al., Cell, 57, 537, 1989. The sequence of all the synthetic oligonucleotides used are provided in FIG. 18.

Preparation of the E6 and E7 genes from HPV16 and HPV18 for insertion into vaccinia virus Cloning of the HPV16 and HPV18 E6 and E7

A fragment of DNA containing the HPV16 E6/7 coding region is prepared by polymerase chain reaction (PCR) amplification from the plasmid pBR322/HPV16 (Durst et al., PNAS, 80, 3812, 1983) using the oligonucleotides SO5 and SO6. A fragment containing the same region from HPV18 is prepared by the same procedure from plasmid pBR322/HPV16 (Boshart et al., EMBO J. 3,1151) using the oligonucleotides SO1 and SO2. Plasmids pBR322/HPV16 and pBR322/HPV18 are both available from Behringwerke AG, P.O. Box 1140 D-3550, Marburg, Germany (alternatively the necessary sequences can be created synthetically from the sequence information provided by the present application).

In each case, this produces a DNA fragment of about 800 base pairs (bp) with a site for the restriction enzyme Nco 1 (CC<u>ATG</u>G) located exactly at the beginning of the E6 gene, and a SmaI site immediately downstream of the termination codon for the E7 gene (FIGS. 1(a) and (b)). The products are then digested with NcoI and SmaI , and cloned into NcoI-SmaI digested plasmid pUC118NS (a modified version of the "phagemid" pUC118 (Viera & Messing, Methods Enzymol., 153,3, 1987) in which NcoI and SmaI sites have been created by site-directed mutagenesis within the polylinker region) to generate the plasmid p1MS7, containing the HPV16 sequences, and pIMS8 containing the HPV18 sequences (FIG. 2). The use of pUC118 is not crucial to the present strategy as any plasmid which can be manipulated by site directed mutagenesis can be successfully used.

Fusion of the E6 and E7ORFs

For insertion into vaccinia virus, the E6 and E7 genes from each HPV type, are first fused together to form a single continuous ORF. This is achieved by site-directed mutagenesis as follows:

(i) The termination codon TAA of HPV16 E6 in pIMS7 is altered using the oligonucleotide S20 to the sequence GGAA. This is in order to convert the normally separate ORFs for HPV16 E6 and E7 into a single ORF (pIMS7.1—FIG. 2).

(ii) The termination codon TAA of HPV18 E6 in pIMS8 is altered using the oligonucleotide S21 to the sequence GGAA. This is in order to convert the normally separate ORFs for HPV18 E6 and E7 into a single ORF (pIMS8.1—FIG. 2). 5

Abolition of the immortalising potential of E7

In order to destroy the immortalising properties of each of the E7 proteins, two key codons within the HPV16 E7 coding sequence, (cys24 and glu26 —FIG. 1(a)) and the equivalent codons from HPV18 E7 (cys27 and glu29—FIG. 1(b)), are altered to glycine residues by site directed mutagenesis as follows.

(i) The sequence of the E7 gene is altered in pIMS7 to encode glycine at codons 24 and 26 (normally encoding cysteine and glutamate respectively, using oligonucleotide S22 (pIMS7.2—FIG. 2).

(ii) The sequence of the E7 gene is altered in pIMS8 to encode glycine at codons 27 and 29 (normally encoding cysteine and glutamate respectively, using oligonucleotide S23 (pIMS8.1B —FIG. 2).

Reduction in intertypic recombination potential of HPV16 and HPV18 E6 and E7 sequence and elimination of potential vaccinia virus transcription termination signal A potential difficulty with the presence of both HPV16 and HPV18 E6 and E7 specific DNA within the genome of a single virus, is that recombination between the two sets of related sequences could lead to loss or rearrangement of information such that expression of the required proteins is disrupted. The invention provides ways of minimising this risk. Firstly, by inserting the two sets of genetic information in the vaccinia genome in opposite orientation to each other (so that recombination will result not in the loss of sequence information, but rather in its inversion). Secondly, by creating specific changes in the E6/7 sequence of one of the HPV virus strains at sites where the homology is greatest. These changes however are made in such a way that the amino acid coding potential of the genes remains unaltered.

The HPV18 E6 sequences is therefore altered by site-directed mutagenesis as follows:

The sequence TTTTTATTCTAGAATTAGAG (SEQ ID NO:01) (which begins 210 nucleotides from the start of E6—underlined in FIG. 1(b)) is mutated, using oligonucleotide S24 to the sequence TTTCTACAGTAGAATCAGAG (SEQ ID NO:02)(pIMS8.2—FIG. 2) (changed nucleotides are in bold type).

A second aim of this change is to eliminate from the HPV18 E6 sequence, the sequence TTTTTAT, which is a potential termination signal for the early vaccinia virus transcription enzyme (Rohrmann et al., Cell., 46, 1029, 1986).

Source and propagation of vaccinia virus

The Wyeth strain of vaccinia virus is used for construction of the therapeutic virus. It is propagated in Vero cells for the purposes of genetic manipulation, and in the human diploid fibroblast cell line MRC5 for the production of the final therapeutic virus stock. Both cell lines are obtained from the National Institute of Biological Standards and Control, South Mims, U.K. The Wyeth strain of vaccinia virus, Vero cells and the cell line MRC5 are also available from the American Type Culture Collection, 12301 Parklawn Drive, Rockville, Md. 20852, U.S.A.

Identification and of neutral sites from the vaccinia virus

Description of neutral sites

For the purpose of insertion of papillomavirus genes within the vaccinia virus genome, sites have been chosen to have two characteristics.

Firstly, they should be non-essential regions, i.e. insertion of foreign genes at these points, will not disrupt any functions of the vaccinia virus to the extent that the virus can no longer grow in tissue culture.

Secondly, they should be neutral sites, i.e. insertion of foreign genes all these points, will not increase or decrease the level of attenuation of the vaccinia virus.

The difference between these two factors can be seen by looking at the thymidine kinase (TK) gene of vaccinia virus. It is a non-essential region, and hence viruses with genes inserted in the TK gene can grow well in tissue culture (Mackett at al., J. Virol., 49, 857, 1984). However, such viruses have been found to be greatly attenuated in vivo (Buller et al., Nature 317, 813, 1985). For the purpose of prophylactic vaccination, such increased attenuation might be desirable. However, for an immunotherapeutic strategy where the danger from the disease to be treated clearly outweighs the risk of vaccine associated complications, use of an attenuated virus is considered undesirable since it could compromise the immunological response to the papillomavirus antigens. Hence, the applicants have identified sites which they judge will not attenuate the virus any further, and have termed them 'neutral sites'. Such sites have been identified within the virus genome by careful analysis of the DNA sequence of the WR strain. The WR strain was originally derived from the Wyeth strain by passage in mouse brain. Therefore the two strains are closely related. The nucleotide sequence of three regions of the WR genome which contain the selected neutral sites are shown in FIGS. 19, 20 and 21. Four neutral sites (A–D) have been chosen on the above discussed criteria as follows:

Site A: gap between SalF17R and SalF19R

Site B: gap between SalF19R and SalF20.5R

Site C: in SalG2R, a potential non-functional gene Site D: in HindB3.5R, a potential non-functional gene These sites (A–D) can be identified by the following stretches of DNA sequence, each of which is 40 nucleotides in length.

A     CTATCTACCAGATTATTATGTGT-TATAAGGTACTTTTTCT (SEQ ID NO:03)

B     TATTGTGCTACTGATTCTTCACAGACT-GAAGATTGTTGAA (SEQ ID NO:04)

C     TCTCTTAAAATGGTTGAGACCAAGCT-TCGTTGTAGAAACA (SEQ ID NO:05)

D     TGAGGCTACCTCGACATACGTGTGCGC-TATCAAAGTGGAA (SEQ ID NO:06)

In other strains these sequences may vary, while still having substantial homology with those given above. In particular a site may have at least 90%, more preferably 95%, homology with the sequence given above.

FIGS. 3–5 show the distribution of initiation codons and open reading frames (ORFs) in the regions of the vaccinia virus genome shown in FIGS. 19, 20 and 21.

FIGS. 6–8 show the same regions with a plot showing to what extent each reading frame conforms to the pattern of codon usage expected for vaccinia genes. A graph of codon usage is plotted for each of the three possible reading frames in each direction (Staden, R., Nucl. Acids Res., 12, 521, 1984; Staden, R., Nucl. Acids Res., 12, 551, 1984). In these codon usage plots, the short vertical bar lines extending from the horizontal axes represent start codons. The longer vertical bar lines placed above the horizontal axes represent stop codons. This sort of plot is a useful way of helping to determine whether a particular ORF is a genuine vaccinia gene. Where there is a likely genuine gene, the graph of codon usage will rise between a start codon and a stop codon. For example, in FIG. 7, it can be seen that the graph of codon usage rises over the region of the SalG2R ORF (the dotted line shows that this frame conforms most of the expected codon usage). For the other two frames the graphs show that they do not conform to vaccinia codon usage. The peak labelled 'part of gk', and marked with a dashed line, also conforms well to vaccinia codon usage. In summary, a genuine gene must start with an initiation (start) codon, end with a termination (stop) codon, and should conform well to vaccinia codon usage along its length. In most cases the conformation to the vaccinia codon usage drops off sharply outside the gene. The neutral sites are further described as follows Site A. Gap between SalF17R and SalF19R Site A is marked on FIGS. 3 and 6. FIG. 9 (SEQ ID NO:15-17) shows the actual DNA sequence with a translation of the ORFs on either side of the site. It can be seen that Site A is placed in an intergenic region between SalF17R and SalF19R. It is placed some 195 bases upstream of SalF19R to avoid any promoter elements associated with that gene. The sequence TTTTTCT (shown in italics) will act as a terminator of early RNA transcription for the SalF17R gene if it is an early gene. However, the site is placed downstream of the first of these, so it will not affect early termination of transcription if it occurs. Examination of FIG. 6 shows that there is no recognisable gene on the opposite strand at this point, and hence this sequence location is suitable as a neutral insertion site.

Site B. Gap between SalF19R and SalF20.5R

Site B is marked on FIGS. 3 and 6. FIG. 10 (SEQ ID NOS:18-20)shows the actual DNA sequence with a translation of the ORFs on either side of the site. It can be seen that Site B is placed in an intergenic region between SalF19R and SalF20.5R. FIG. 6 shows that it is within a region of high vaccinia codon usage, but that this region does not form a genuine gene, having no initiation codon. In addition, FIG. 6 suggests that Sal20.5R is not a complete gene, as the conformation to vaccinia codon usage drops off dramatically at the start of the gene. In the event that SalF20.5R is a genuine gene, Site B is placed some 70 bases upstream of SalF20.5R which may well avoid any promoter elements associated with that gene. (Note: many vaccinia promoter elements are located in approximately 35 bases upstream of the start of the gene.) In addition SalF20R has no TTTTTNT (N=any nucleotide) transcription termination signal with which Site B could interfere. Hence this sequence location is suitable as a neutral insertion site.

Site C. Within SalG2R, a potential non-functional gene

Site C is marked on FIG. 4. The ORF SalG2R has considerable similarity to the guanylate kinase (GK) gene of yeast. This similarity is shown in FIG. 11. Sequence upstream of the SalG2R ORF (but in a different frame) has been added on to SalG2R, to see if the match to GK extends beyond the boundaries of the original open reading frame. The match appears to extend beyond the 5' and of the SalG2R ORF. In particular, an important site in the yeast GK gene, the ATP/GTP binding site (shown underlined) only matches in the out of frame sequence upstream of the SalG2R ORF. Hence, it is very likely that the SalG2R gene is not active as a guanylate kinase and can be referred to as a 'pseudogene'. If the gene is inactive as the applicants deduce, then it will serve as a neutral insertion site.

Site D. Within HindB3.5R, a potential non-functional gene

FIG. 5 shows that site D lies within the region designated HindB3.5R. This region, although conforming to vaccinia codon usage, has no start codon and is therefore not a genuine gene. The codon usage plot shown in FIG. 8 indicates that it probably was once a functional gene, and may well have been attached to HindB3R (a shift in the codon usage preference occurs here well away from the termination codon of the HindB3R ORF which suggests that the last section of HindB3R is not properly part of this gene.) Hence it is likely that HindB3.5R is not active as a gene and can be used as a neutral insertion site. FIG. 12 (SEQ ID NOS:23-25) shows the actual DNA sequence with a translation of the ORFs on either side of the site. It can be seen that site D is placed in an intergenic region between HindB3R and HindB4R as well as being within the nonfunctional HindB3.5R.

Preparation of vector for cloning of neutral sites

In order to insert foreign genetic information into the neutral sites described above, DNA copies of the neutral sites, together with an appropriate amount of flanking DNA from the vaccinia genome (approximately 500 bases on either side) must first be cloned into a plasmid vector. These plasmids may then be used to introduce the foreign DNA into the vaccinia virus genome; the vaccinia virus 'flanking sequences' around the inserted gene serve to allow homologous recombination between the plasmid DNA and the viral DNA, with the consequent insertion of the foreign gene at the desired location.

Cloning of neutral site sequences

Plasmids containing flanking regions from the neutral sites are constructed as follows. DNA is prepared from the Wyeth strain of vaccinia virus by the method of Esposito et al., (J. Virol. Meth. 2: 175, 1981). The polymerase chain reaction (PCR) is used to remove an approximately 1000 base pair (bp) fragment from DNA of the Wyeth strain of vaccinia virus. Pairs of oligonucleotides are chosen approximately 500 bp either side of the chosen neutral site. These oligonucleotides are based on the sequence of the WR strain, but are chosen in regions where the sequence of the WR strain is identical to that of the Copenhagen strain (Goebel et al., Virology 179:247, 1990). The oligonucleotides incorporate restriction enzyme recognition sequences so that they can be cloned easily into a plasmid. For neutral sites A (SEQ ID NO:03), B (SEQ ID NO:04), and D (SEQ ID NO:06) the restriction sites are EcoR1 and HindIII. For neutral site C (SEQ ID NO:05) the HindIII site is replaced by an SphI site, since there is an internal HindIII site in the chosen flanking sequences.

The oligonucleotides used for PCR are listed below:

Site A (SEQ ID NO:03) leftMB 16
Site A (SEQ ID NO:03) rightMB 17
Site B (SEQ ID NO:04) leftMB 24
Site B (SEQ ID NO:04) rightMB 25
Site C (SEQ ID NO:05) leftMB 18
Site C (SEQ ID NO:05) rightMB 19
Site D (SEQ ID NO:06) leftMB 22
Site D (SEQ ID NO:06) rightMB 23

DNA fragments of approximately 1kb are then prepared using these pairs of oligonucleotides by PCR amplification, digested with EcoRI and HindIII (for site A (SEQ NO:03), B (SEQ ID NO:04) and D (SEQ ID NO:06) or with EcoRI and SphI (for site C (SEQ ID NO:05)) and cloned into HindIII and EcoRI-digested pUC118 (FIG. 13) to generate the plasmids pIMMC7a, pIMMC7b, pIMMC7c and pIMMC7d.

Creation of unique restriction sites for insertion at the neutral sites

A suitable restriction enzyme site is then introduced at the selected location within each of the plasmids. This is achieved using site directed mutagenesis using an oligonucleotide containing the desired new unique site and flanked by 15 bases of sequence to either side (see below).

The plasmids modified in this fashion are designated pIMMC8a–d (FIG. 13).

| original plasmid | oligonucleotide site introduced | new plasmid |
|---|---|---|
| pIMMC7a | MB35SnaB1 | pIMMC8a |
| pIMMC7b | MB36Hpa1 | pIMMCb |
| pIMMC7c | MB37Stu1 | pIMMC8c |
| pIMMC7d | MB38SnaB1 | pIMMC8d |

Cloning of the vaccinia virus early/late promoter sequences

The p7.5 and H6 promoters from vaccinia virus genomic DNA are prepared by PCR amplification as described below.

A pair of complementary oligonucleotides (S7 and S8) is synthesised to include the following restriction enzyme sites, HindIII, SnaI HpaI, HindIII, SalI, NcoI, SmaI, SnaBI and EcoRI such that the pair, after annealing, present at one end HindIII compatible overhanging ends, and at the other, EcoRI compatible overhanging ends. The two oligonucleotides are allowed to anneal and are inserted into pUC118 cut with EcoRI and HindIII (FIG. 14). The resulting vector is called pIMMC3.

A DNA molecule of approximately 180 bp containing the H6 promoter is removed from the WR strain of vaccinia virus by PCR amplification using the oligonucleotides MB15 (anneals upstream and includes a 5'-SalI site) and MB7 (anneals downstream and includes a 5'-HindIII site). This is cloned into pIMMC3 cleaved with HindIII and SalI to create pIMMC4a (FIG. 14). A DNA molecule of approximately 200 bp containing the p7.5 promoter is then removed from the WR strain of vaccinia virus by PCR amplification using the oligonucleotides MB32 (anneals upstream and includes a 5'-SalI site) and MB33 (anneals downstream and includes a 5'NcoI site). This is cloned into pIMMC3 cleaved with NcoI and SalI to create pIMMC14b.

Construction of the therapeutic virus

The strategy required to generate a recombinant vaccinia virus containing and expressing the E6-E7 proteins from HPV16 and HPV18, based on the elements described above involves five main stages as outlined below.

i) Cloning of the modified E6-7 genes downstream of vaccinia early promoter sequences A DNA fragment containing the modified HPV16 E6-7 sequence is excised from pIMS7.2 by digestion with HindIII and SmaI, and cloned into HindIII and HpaI-digested pIMMC4a to generate pIMS12 (FIG. 15).

A DNA fragment containing the modified HPV18 E6-7 sequence is excised from pIMS8.2 by digestion with NcoI and SmaI, and cloned into NcoI and SmaI-digested pIMMC14b to generate pIMS14 (FIG. 15).

ii) Preparation of a plasmid vector containing both HPV16 and HPV18 E6-7 sequences together with their upstream vaccinia promoters.

A DNA fragment containing the HPV18 E6-7 region together with the upstream p7.5 promoter is excised from pIMS14 with SalI and SmaI and inserted into SalI and SmaI-digested pIMS12 to generate pIMS15 (FIG. 15)

iii) Insertion of the HPV E6-7/promoter "double" cartridge into the neutral site containing plasmids.

A DNA fragment containing both the HPV16 and HPV18 E6-7 coding regions together with their upstream promoter elements is excised from pIMS15 with SnaB1 and inserted into the appropriately-digested neutral site-containing plasmids pIMMC7a–d. This step is shown in FIG. 16, and the resulting plasmids are designated pIMMC9a–d.

iv) Introduction via homologous recombination of the neutral site DNA, together with the intervening HPV sequences, into the vaccinia virus genome to create a recombinant virus expressing the two modified HPV E6-7 sequences.

The recombinant plasmids pIMMC9a–d are purified and allowed to recombine into vaccinia (FIG. 17) using standard protocols (Mackett et al., in D. M. Glover (ed) DNA Cloning: a Practical Approach, Oxford and Washington D.C., IRL Press, 1985). Viruses which have acquired the HPV sequences are identified by probing with radiolabelled HPV specific sequences. Viral plaques are lifted onto nitrocellulose (Villareal and Berg, Science 196, 183, 1977) and probed with radiolabelled NcoI-SmaI fragment from pIMS14 containing the HPV18 E67 gene. Recombinant viruses are then isolated from the agarose overlay and plaque purified three times. They are checked for the presence of the appropriate DNA sequences by Southern blotting of purified virus DNA using DNA probes derived from the HPV E6 and E7 genes, and for expression of the appropriate sequences by western blotting using antisera specific for the HPV E6 and E7 proteins.

Cloning of the therapeutic virus in MRC5 cells

Stocks of the final recombinant virus are prepared by growth in Vero cells, and are used to infect MRC5 cells deemed suitable for the preparation of material suitable for use as human vaccines. The virus is plaque-purified three times by standard methods, and finally a stock prepared for clinical use.

Confirmation of presence of the correct HPV DNA insert

A sample of this stock virus is checked once again for the presence of correctly configured virus DNA, and for expression of the correct virus proteins. FIG. 22 shows the analysis by PCR, of a recombinant vaccinia virus (v9a.1) in which the HPV DNA cassette is inserted at Site A. The diagram shown in panel (a) indicates the DNA fragments expected if insertion of the correct DNA has occurred. It can be seen in panel (b) that the actual pattern of PCR products generated is consistent with that expected.

Confirmation of expression of the HPV DNA insert

The recombinant viruses are then checked for expression of the expected HPV proteins. An example of this analysis is shown in FIG. 23. Vero cells are infected with recombinant virus v9a.1 (HPV DNA inserted at Site A), and the cells examined by western blotting for the presence of the HPV E67 fusions proteins using monoclonal antibodies specific for the HPV16 E7 protein (camvir3) and for the HPV18 E7 protein (7E10). It can be seen that both monoclonal antibodies recognise specifically proteins of the expected size in cells infected with the recombinant virus v9a.1, but not in cells infected with the control parent virus Wyeth strain. These recognised proteins co-migrate with proteins synthesised by in vitro translation of mRNA encoding the expected HPV fusion proteins (HPV 16 E67 and HPV18 E67). This experiment indicates successful expression of the heterologous gene sequences from the recombinant virus.

Stability of the HPV DNA insert

For the recombinant virus to be of use clinically, it is important that the inserted sequences remain genetically stable over multiple virus passage, and the DNA insert was carefully designed to promote this genetic instability. To confirm the stability of the HPV information within the recombinant virus genome, the virus is subjected to 9 serial passages, (multiplicity of infection=10 pfu/cell) in Vero cells. Subsequently 20 plaque isolates are picked, and analysed for the presence of the correct HPV DNA insert by PCR analysis as described in FIG. 22. The data obtained for recombinant virus A are shown in FIG. 24. All 20 virus isolates retained the HPV information in the expected Genetic arrangement indicating a considerable degree of genetic stability.

Animal experiments

The virulence of the recombinant virus is compared in animal experiments with that of the parental Wyeth strain.

Groups of 20 mice are inoculated intranasally each with $10^7$ pfu of Wyeth strain or recombinant virus in a total volume of 20 μl. Two mice are sacrificed at 1 day, 3 days and 5 days following inoculation, and the lungs dissected out. The amount of virus present in the lungs is then measured by grinding the tissue, and assay of the homogenate by standard vaccinia virus plaque assay. The results of such an experiment for the recombinant virus v9a.1 (HPV infromation inserted at site A (SEQ ID NO:03) are shown in FIG. 25. It can be seen that the recombinant virus retains the ability to replicate in mice, and that the level of virus produced in the lungs of the infected animals is similar to that seen with the parental Wyeth strain.

Therapeutic Use

A stock of the recombinant virus is prepared by infection of MRC5 cells, and adjusted to a concentration of not less than $10^8$ pfu/ml. 20 μl of this material is applied to the arm of the patient, which is then scarified through the virus droplet with a bifurcated needle, according to the standard procedure used for vaccination against smallpox.

We claim:

1. The recombinant vaccinia virus vector which comprises at least one pair of nucleotide sequences, wherein each of said nucleotide sequences comprises a promoter and an open reading frame which is heterologous to said vaccinia virus and which encodes all or an antigenic part of a human papilloma virus (HPV) protein or an immunologically cross-reactive mutant thereof;

wherein said nucleotide sequences of said pair possess a degree of sequence homology with each other and are inverted with respect to each other in said vaccinia virus vector in order to reduce the risk of recombination which would otherwise occur if said sequences were not arranged in an inverted orientation.

2. The recombinant virus vector according to claim 1 wherein the pair of nucleotide sequences encode all or an antigenic part of the HPV wild-type proteins HPV16E7 and HPV18E7 or immunologically cross-reactive mutants thereof.

3. The recombinant virus vector according to claim 1 wherein the pair of nucleotide sequences encode all or an antigenic part of the HPV wild-type proteins HPV16E6 and HPV18E6 or immunologically cross-reactive mutants thereof.

4. The recombinant virus vector according to claim 1 wherein the nucleotide sequences are inserted into the virus vector at one or more neutral sites.

5. The recombinant virus vector according to claim 2 which comprises a further pair of nucleotide sequences which encode all or an antigenic part of the HPV wild-type proteins HPV16E6 and HPV18E6 or immunologically cross-reactive mutants thereof.

6. The recombinant virus vector according to claim 1 or 5 wherein two or more nucleotide sequences of different said pairs are fused together to form a single open reading frame.

7. The recombinant virus vector according to claim 2 wherein the pair of nucleotide sequences encode all or an antignic part of immunological cross-reactive mutants of the wild-type proteins HPV16E7 and HPV18E7 and wherein the nucleotide sequence encoding amino acids corresponding with residues cys 24 and glu 26 of wild-type protein HPV16E7 or to residues cys 27 and glu 29 of wild-type protein HPV18E7 is changed so as to encode glycine residues.

8. The recombinant virus vector according to claim 5 in which the pairs of nucleotide sequences are arranged in the virus vector according to any one of the options as shown in FIG. 26.

9. The recombinant virus vector according to claim 6 wherein the fusions are via a single codon encoding a small neutral amino acid.

10. The recombinant virus vector according to claim 9 wherein the amino acid is glycine.

11. The recombinant virus vector according to claim 8 which comprises a first open reading frame having a fused genetic sequence encoding part or all of the wild-type proteins E6 and E7 from HPV16; and a separate second open reading frame having a fused genetic sequence encoding part or all of the wild-type proteins E6 and E7 from HPV18;

wherein the first and second open reading frames are invented with respect to one another whereby either:
  i) the E6 coding sequences of HPV16 and HPV18 are both located between the E7 coding sequences of HPV16 and HPV18; or
  ii) the E7 coding sequences of HPV16 and HPV18 are both located between the E6 coding sequences of HPV16 and HPV18; and wherein any of said wild-type proteins may be replaced by a mutant protein immunologically cross-reactive therewith.

12. The recombinant virus vector according to claim 8 which comprises a first open reading frame having a fused genetic sequence encoding all or an antigenic part of the wild-type proteins E6 and E7 from HPV16; and a separate second open reading frame having a fused genetic sequence encoding all or an antigenic part of the wild-type proteins E6 and E7 from HPV18;

wherein the E6 coding sequences of HPV16 and HPV18 are both located between the E7 coding sequences of HPV16 and HPV18; and each open reading frame has a corresponding promoter, the promoters being located between the first and second open reading frames whereby the open reading frames are transcribed outwardly; and wherein any of said wild-type proteins may be replaced by immunologically cross-reactive mutants thereof.

13. The recombinant virus vector according to claim 8 or 12 wherein either or both of the nucleotide sequences in a said pair of nucleotide sequences comprise nucleotide mutations that do not change the translated amino acid sequences but make the nucleotide sequences themselves less homologous than the corresponding wild-type nucleotide sequences.

14. The recombiant virus vector according to claim 1, 5, 8, or 12 wherein said heterologous nucleotide sequences may comprise part or all of the sequences shown in FIG. 1(a) and 1(b) (SEQ ID NOS:7–14).

15. The recombinant virus vector according to claim 11 wherein each of the first and second open reading frames has a corresponding promoter and the two open reading frames each with its promoter, are arranged next to each other in the virus.

16. The recombinant virus vector according to claim 15 wherein either:
   i) the promoters are located between the first and second open reading frames whereby the open reading frames are transcribed outwardly; or
   ii) the promoters are located outside the first and second open reading frames whereby the open reading frames are transcribed inwardly.

17. The recombinant virus vector according to claim 13 wherein the alteration in nucleotide sequence does not result in an alteration of the encoded amino acid sequence.

18. A recombinant vaccinia virus vector which comprises at least one pair of nucleotide sequences heterologous to said vaccinia virus, wherein each of said nucleotide sequences encodes all or an antigenic part of a human papillomavirus (HPV) protein or an immunologically cross-reactive mutant thereof; wherein said nucleotide sequences of said pair encode corresponding antigens of different HPV strains; and wherein said nucleotide sequences of said pair are arranged in said virus vector such that they are inverted with respect to each other.

19. The recombinant vaccinia virus vector according to claim 18 wherein the pair of nucleotide sequences encode all or an antigenic part of the HPV wild-type proteins HPV16E7 and HPV18E7 or immunologically cross-reactive mutants thereof.

20. The recombinant vaccinia virus vector according to claim 18 wherein the pair of nucleotide sequences encode all or an antigenic part of the HPV wild-type proteins HPV 16E6 and HPV 18E6 or immunologically cross-reactive mutants thereof.

21. The recombinant vaccinia virus vector according to claim 18 wherein said nucleotide sequence are inserted into the virus vector at one or more neutral sites.

22. The recombinant vaccinia virus vector according to claim 4 wherein said one or more neutral sites is selected from sites having at least 90% sequence homology with:

A) the gap between SalIF17R and SalIF19R of strain WR having the sequence

CTATCTACCAGATTATTATGTGTTATAAGGTACTTTTTCT (SEQ ID NO:03);

B) the gap between SalIF19R and SalIF20.5R of strain WR having the sequence
   ti TATTGTGCTACTGATTCTTCACAGACT-GAAGATTGTTGAA (SEQ ID NO:04);

C) a region in SalIG2R of strain WR having the sequence

TCTCTTAAAATGGTTGAGACCAAGCTTCGTTGTAGAAACA (SEQ ID NO:05);

D) a region in HindB3.5R of strain WR having the sequence

TGAGGCTACCTCGACATACGTGTGCGCTATCAAAGTGGAA (SEQ ID NO:06).

23. The recombinant vaccinia virus vector according to claim 19 which comprises a further pair of nucleotide sequences which encode all or an antigenic part of the HPV wild-type proteins HPV16E6 and HPV18E6 or immunologically cross-reactive mutants thereof.

24. The recombinant vaccinia virus vector according to claim 19 wherein the pair of nucleotide sequences encode all or an antigenic part of immunological cross-reactive mutants of the wild-type proteins HPV16E7 and HPV18E7 and wherein the nucleotide sequence encoding amino acids corresponding to residues cys 24 and glu 26 of wild-type protein HPV16E7 or to residues cys 27 and glu 29 of wild-type protein HPV18E7 is changed so as to encode glycine residues.

25. The recombinant vaccinia virus vector according to claim 18 or 23 wherein two or more nucleotide sequences of said different pairs are fused together to form a single open reading frame.

26. The recombinant vaccinia virus vector according to claim 23 in which the pairs of nucleotide sequences are arranged in the virus vector according to any one of the options as shown in FIG. 26.

27. The recombinant vaccinia virus vector according to claim 25 wherein the fusions are via a single codon encoding a small neutral amino acid.

28. The recombinant vaccinia virus vector according to claim 27 wherein the amino acid is glycine.

29. The recombinant vaccinia virus vector according to claim 26 which comprises a first open reading frame having a fused genetic sequence encoding part or all of the wild-type proteins E6 and E7 from HPV16; and a separate second open reading frame having a fused genetic sequence encoding part or all of the wild-type proteins E6 and E7 from HPV18;

wherein the first and second open reading frames are inverted with respect to one another whereby either:
   i) the E6 coding sequences of HPV16 and HPV18 are both located between the E7 coding sequences of HPV16 and HPV18; or
   ii) the E7 coding sequences of HPV16 and HPV18 are both located between the E6 coding sequences of HPV16 and HPV18; and wherein any of said wild-type proteins may be replaced by a mutant protein immunologically cross-reactive therewith.

30. The recombinant vaccinia virus vector according to claim 26 which comprises a first open reading frame having a fused genetic sequence encoding all or an antigenic part of the wild-type proteins E6 and E7 from HPV16; and a separate second open reading frame having a fused genetic sequence encoding all or an antigenic part of the wild-type proteins E6 and E7 from HPV18;

wherein the E6 coding sequences of HPV16 and HPV18 are both located between the E7 coding sequences of HPV16 and HPV18; and each open reading frame has a corresponding promoter, the promoters being located between the first and second open reading frames whereby the open reading frames are transcribed outwardly; and wherein any of said wild-type proteins may be replaced by immunologically cross-reactive mutants thereof.

31. The recombinant vaccinia virus vector according to claim 26 or 30 wherein either or both of the nucleotide sequences in a said pair of nucleotide sequences comprise nucleotide mutations that do not change the translated amino acid sequences but make the nucleotide sequences themselves less homologous than the corresponding wild-type nucleotide sequences.

32. The recombinant vaccinia virus vector according to claim 29 wherein each of the first and second open reading frames has a corresponding promoter and the two open reading frames each with its promoter, are arranged next to each other in the virus.

33. The recombinant virus vector according to claim 32 wherein either:

i) the promoters are located between the first and second open reading frames whereby the open reading frames are transcribed outwardly; or ii) the promoters are located outside the first and second open reading frames whereby the open reading frames are transcribed inwardly.

34. The recombinant vaccinia virus vector according to claim 18, 23, 26, or 30, wherein said heterologous nucleotide sequences comprise part or all of the sequences shown in FIGS. 1(*a*) and 1(*b*) (SEQ ID NOS:7–14).

35. The recombinant vaccinia virus vector according to claim 31 wherein the alteration in nucleotide sequence does not result in an alteration of the encoded amino acid sequence.

36. The recombinant virus vector according to claim 21 which is a recombinant vaccinia virus and wherein said one or more neutral sites is selected from sites having at least 90% sequence homology with:

A) the gap between SalIF17R and SalIF19R of strain WR having the sequence

CTATCTACCAGATTATTATGTGTTATAAGGTACTTTTTCT (SEQ ID NO:03);

B) the gap between SalIF19R and SalIF20.5R of strain WR having the sequence

TATTGTGCTACTGATTCTTCACAGACTGAAGATTGTTGAA (SEQ ID NO:04);

C) a region in SalIG2R of strain WR having the sequence

TCTCTTAAAATGGTTGAGACCAAGCTTCGTTGTAGAAACA (SEQ ID NO:05);

D) a region in HindB3.5R of strain WR having the sequence

TGAGGCTACCTCGACATACGTGTGCGCTATCAAAGTGGAA (SEQ ID NO:06).

37. A recombinant vaccinia virus vector which comprises at least one pair of nucleotide sequences, wherein each of said nucleotide sequences comprises a promoter and an open reading frame which is heterologous to said vaccinia virus and which encodes all or an antigenic part of a human papilloma virus (HPV) protein or an immunologically cross-reactive mutant thereof;

wherein said nucleotide sequences of said pair have sequence homology of about 57% or greater whereby the degree of homology is sufficient for recombination between said sequences to occur; and wherein said nucleotide sequences of said pair are arranged in said virus vector such that they are inverted with respect to each other, thereby to reduce the risk of said recombination.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

TTTTTATTCT AGAATTAGAG    20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TTTCTACAGT AGAATCAGAG    20

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

CTATCTACCA GATTATTATG TGTTATAAGG TACTTTTCT    40

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

TATTGTGCTA CTGATTCTTC ACAGACTGAA GATTGTTGAA    40

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

TCTCTTAAAA TGGTTGAGAC CAAGCTTCGT TGTAGAAACA    40

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

TGAGGCTACC TCGACATACG TGTGCGCTAT CAAAGTGGAA    40

( 2 ) INFORMATION FOR SEQ ID NO:7:

( i ) SEQUENCE CHARACTERISTICS:
        ( A ) LENGTH: 790 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| | | | | | | |
|---|---|---|---|---|---|---|
| ATCCATGGA | CCAAAAGAGA | ACTGCAATGT | TTCAGGACCC | ACAGGAGCGA | CCCAGAAAGT | 60 |
| TACCACAGTT | ATGCACAGAG | CTGCAAACAA | CTATACATGA | TATAATATTA | GAATGTGTGT | 120 |
| ACTGCAAGCA | ACAGTTACTG | CGACGTGAGG | TATATGACTT | TGCTTTTCGG | GATTTATGCA | 180 |
| TAGTATATAG | AGATGGGAAT | CCATATGCTG | TATGTGATAA | ATGTTTAAAG | TTTTATTCTA | 240 |
| AAATTAGTGA | GTATAGACAT | TATTGTTATA | GTTGTATGG | AACAACATTA | GAACAGCAAT | 300 |
| ACAACAAACC | GTTGTGTGAT | TTGTTAATTA | GGTGTATTAA | CTGTCAAAAG | CCACTGTGTC | 360 |
| CTGAAGAAAA | GCAAAGACAT | CTGGACAAAA | AGCAAAGATT | CCATAATATA | AGGGGTCGGT | 420 |
| GGACCGGTCG | ATGTATGTCT | TGTTGCAGAT | CATCAAGAAC | ACGTAGAGAA | ACCCAGCTGT | 480 |
| AATCATGCAT | GGAGATACAC | CTACATTGCA | TGAATATATG | TTAGATTTGC | AACCAGAGAC | 540 |
| AACTGATCTC | TACTGTTATG | AGCAATTAAA | TGACAGCTCA | GAGGAGGAGG | ATGAAATAGA | 600 |
| TGGTCCAGCT | GGACAAGCAG | AACCGGACAG | AGCCCATTAC | AATATTGTAA | CCTTTTGTTG | 660 |
| CAAGTGTGAC | TCTACGCTTC | GGTTGTGCGT | ACAAAGCACA | CACGTAGACA | TTCGTACTTT | 720 |
| GGAAGACCTG | TTAATGGGCA | CACTAGGAAT | TGTGTGCCCC | ATCTGTTCTC | AGAAACCATA | 780 |
| ACCCGGGTGA | | | | | | 790 |

( 2 ) INFORMATION FOR SEQ ID NO:8:

( i ) SEQUENCE CHARACTERISTICS:
        ( A ) LENGTH: 263 amino acids
        ( B ) TYPE: amino acid
        ( C ) STRANDEDNESS: single
        ( D ) TOPOLOGY: linear (ii) MOLECULE TYPE: protein (ix) FEATURE:
(A) NAME/KEY: Protein
(B) LOCATION: 1..263
(D) OTHER INFORMATION: /note= "Xaa refers to stop codon in the open reading frame."

(xi) SEQUENCE DESCRIPTION: SEQ ID NO:8:

| Ile | Pro | Trp | Thr | Lys | Arg | Glu | Leu | Gln | Cys | Phe | Arg | Thr | His | Arg | Ser |
|---|---|---|---|---|---|---|---|---|---|---|---|---|---|---|---|
| 1 | | | | 5 | | | | | 10 | | | | | 15 | |
| Asp | Pro | Glu | Ser | Tyr | His | Ser | Tyr | Ala | Gln | Ser | Cys | Lys | Gln | Leu | Tyr |
| | | | 20 | | | | | 25 | | | | | 30 | | |
| Met | Ile | Xaa | Tyr | Xaa | Asn | Val | Cys | Thr | Ala | Ser | Asn | Ser | Tyr | Cys | Asp |
| | | 35 | | | | | 40 | | | | | 45 | | | |
| Val | Arg | Tyr | Met | Thr | Leu | Leu | Phe | Gly | Ile | Tyr | Ala | Xaa | Tyr | Ile | Glu |
| | 50 | | | | | 55 | | | | | 60 | | | | |
| Met | Gly | Ile | His | Met | Leu | Tyr | Val | Ile | Asn | Val | Xaa | Ser | Phe | Ile | Leu |
| 65 | | | | | 70 | | | | | 75 | | | | | 80 |
| Lys | Leu | Val | Ser | Ile | Asp | Ile | Ile | Val | Ile | Val | Cys | Met | Glu | Gln | His |
| | | | | 85 | | | | | 90 | | | | | 95 | |
| Xaa | Asn | Ser | Asn | Thr | Thr | Asn | Arg | Cys | Val | Ile | Cys | Xaa | Leu | Gly | Val |
| | | | | 100 | | | | | 105 | | | | | 110 | |
| Leu | Thr | Val | Lys | Ser | His | Cys | Val | Leu | Lys | Lys | Ser | Lys | Asp | Ile | Trp |
| | | | 115 | | | | | 120 | | | | | 125 | | |
| Thr | Lys | Ser | Lys | Asp | Ser | Ile | Ile | Xaa | Gly | Val | Gly | Gly | Pro | Val | Asp |
| | 130 | | | | | 135 | | | | | 140 | | | | |
| Val | Cys | Leu | Val | Ala | Asp | His | Gln | Glu | His | Val | Glu | Lys | Pro | Ser | Cys |
| 145 | | | | | 150 | | | | | 155 | | | | | 160 |
| Asn | His | Ala | Trp | Arg | Tyr | Thr | Tyr | Ile | Ala | Xaa | Ile | Tyr | Val | Arg | Phe |
| | | | | 165 | | | | | 170 | | | | | 175 | |
| Ala | Thr | Arg | Asp | Asn | Xaa | Ser | Leu | Leu | Leu | Xaa | Ala | Ile | Lys | Xaa | Gln |
| | | | 180 | | | | | 185 | | | | | 190 | | |
| Leu | Arg | Gly | Gly | Gly | Xaa | Asn | Arg | Trp | Ser | Ser | Trp | Thr | Ser | Arg | Thr |
| | | 195 | | | | | 200 | | | | | 205 | | | |
| Gly | Gln | Ser | Pro | Leu | Gln | Tyr | Cys | Asn | Leu | Leu | Leu | Gln | Val | Xaa | Leu |
| | 210 | | | | | 215 | | | | | 220 | | | | |
| Tyr | Ala | Ser | Val | Val | Arg | Thr | Lys | His | Thr | Arg | Arg | His | Ser | Tyr | Phe |
| 225 | | | | | 230 | | | | | 235 | | | | | 240 |
| Gly | Arg | Pro | Val | Asn | Gly | His | Thr | Arg | Asn | Cys | Val | Pro | His | Leu | Phe |
| | | | | 245 | | | | | 250 | | | | | 255 | |
| Ser | Glu | Thr | Ile | Thr | Arg | Val | | | | | | | | | |
| | | | 260 | | | | | | | | | | | | |

(2) INFORMATION FOR SEQ ID NO:9:

(i) SEQUENCE CHARACTERISTICS:
(A) LENGTH: 263 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..263
(D) OTHER INFORMATION: /note= "Xaa refers to stop codon in the open reading frame."

(xi) SEQUENCE DESCRIPTION: SEQ ID NO:9:

| Ser | His | Gly | Pro | Lys | Glu | Asn | Cys | Asn | Val | Ser | Gly | Pro | Thr | Gly | Ala |
| 1 | | | | 5 | | | | | 10 | | | | | 15 | |
| Thr | Gln | Lys | Val | Thr | Thr | Val | Met | His | Arg | Ala | Ala | Asn | Asn | Tyr | Thr |
| | | | 20 | | | | | 25 | | | | | 30 | | |
| Xaa | Tyr | Asn | Ile | Arg | Met | Cys | Val | Leu | Gln | Ala | Thr | Val | Thr | Ala | Thr |
| | | 35 | | | | | 40 | | | | | 45 | | | |
| Xaa | Gly | Ile | Xaa | Leu | Cys | Phe | Ser | Gly | Phe | Met | His | Ser | Ile | Xaa | Arg |
| | 50 | | | | | 55 | | | | | 60 | | | | |
| Trp | Glu | Ser | Ile | Cys | Cys | Met | Xaa | Xaa | Met | Phe | Lys | Val | Leu | Phe | Xaa |
| 65 | | | | | 70 | | | | | 75 | | | | | 80 |
| Asn | Xaa | Xaa | Val | Xaa | Thr | Leu | Leu | Leu | Xaa | Phe | Val | Trp | Asn | Asn | Ile |
| | | | | 85 | | | | | 90 | | | | | 95 | |
| Arg | Thr | Ala | Ile | Gln | Gln | Thr | Val | Val | Xaa | Phe | Val | Asn | Xaa | Val | Tyr |
| | | | 100 | | | | | 105 | | | | | 110 | | |
| Xaa | Leu | Ser | Lys | Ala | Thr | Val | Ser | Xaa | Arg | Lys | Ala | Lys | Thr | Ser | Gly |
| | | 115 | | | | | 120 | | | | | 125 | | | |
| Gln | Lys | Ala | Lys | Ile | Pro | Xaa | Tyr | Lys | Gly | Ser | Val | Asp | Arg | Ser | Met |
| | 130 | | | | | 135 | | | | | 140 | | | | |
| Tyr | Val | Leu | Leu | Gln | Ile | Ile | Lys | Asn | Thr | Xaa | Arg | Asn | Pro | Ala | Val |
| 145 | | | | | 150 | | | | | 155 | | | | | 160 |
| Ile | Met | His | Gly | Asp | Thr | Pro | Thr | Leu | His | Glu | Tyr | Met | Leu | Asp | Leu |
| | | | | 165 | | | | | 170 | | | | | 175 | |
| Gln | Pro | Glu | Thr | Thr | Asp | Leu | Tyr | Cys | Tyr | Glu | Gln | Leu | Asn | Asp | Ser |
| | | | 180 | | | | | 185 | | | | | 190 | | |
| Ser | Glu | Glu | Glu | Asp | Glu | Ile | Asp | Gly | Pro | Ala | Gly | Gln | Ala | Glu | Pro |
| | | 195 | | | | | 200 | | | | | 205 | | | |
| Asp | Arg | Ala | His | Tyr | Asn | Ile | Val | Thr | Phe | Cys | Cys | Lys | Cys | Asp | Ser |
| | 210 | | | | | 215 | | | | | 220 | | | | |
| Thr | Leu | Arg | Leu | Cys | Val | Gln | Ser | Thr | His | Val | Asp | Ile | Arg | Thr | Leu |
| 225 | | | | | 230 | | | | | 235 | | | | | 240 |
| Glu | Asp | Leu | Leu | Met | Gly | Thr | Leu | Gly | Ile | Val | Cys | Pro | Ile | Cys | Ser |
| | | | | 245 | | | | | 250 | | | | | 255 | |
| Gln | Lys | Pro | Xaa | Pro | Gly | Xaa | | | | | | | | | |
| | | | 260 | | | | | | | | | | | | |

( 2 ) INFORMATION FOR SEQ ID NO:10:

( i ) SEQUENCE CHARACTERISTICS:
        ( A ) LENGTH: 182 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..182
        ( D ) OTHER INFORMATION: /note= "Xaa refers to stop codon in
           the open reading frame."

( x i ) SEQUENCE DESCRIPTION: SEQ ID NO:10:

| Pro | Met | Asp | Gln | Lys | Arg | Thr | Ala | Met | Phe | Gln | Asp | Pro | Gln | Glu | Arg |
| 1 | | | | 5 | | | | | 10 | | | | | 15 | |
| Pro | Arg | Lys | Leu | Pro | Gln | Leu | Cys | Thr | Glu | Leu | Gln | Thr | Thr | Ile | His |
| | | | 20 | | | | | 25 | | | | | 30 | | |
| Asp | Ile | Ile | Leu | Glu | Cys | Val | Tyr | Cys | Lys | Gln | Gln | Leu | Leu | Arg | Arg |
| | | 35 | | | | | 40 | | | | | 45 | | | |
| Glu | Val | Tyr | Asp | Phe | Ala | Phe | Arg | Asp | Leu | Cys | Ile | Ile | Ser | Glu | Tyr |

|   |   |   |   | 50 |   |   |   |   | 55 |   |   |   |   | 60 |   |   |   |
|---|---|---|---|----|---|---|---|---|----|---|---|---|---|----|---|---|---|
| Arg 65 | His | Tyr | Cys | Tyr | Ser 70 | Leu | Tyr | Gly | Thr | Thr 75 | Leu | Glu | Gln | Gln | Tyr 80 |
| Glu | Glu | Lys | Gln | Arg 85 | His | Leu | Asp | Lys | Lys 90 | Gln | Arg | Phe | His | Asn 95 | Ile |
| Arg | Gly | Arg | Trp 100 | Ser | Cys | Met | Glu | Ile 105 | His | Leu | His | Cys | Met 110 | Asn | Ile |
| Cys | Xaa | Ile 115 | Cys | Asn | Gln | Arg | Gln 120 | Val | Gln | Leu | Asp | Lys 125 | Gln | Asn | Arg |
| Thr | Glu 130 | Pro | Ile | Thr | Ile | Leu 135 | Xaa | Pro | Phe | Val | Ala 140 | Ser | Val | Thr | Leu |
| Arg 145 | Phe | Gly | Cys | Ala | Tyr 150 | Lys | Ala | His | Thr | Xaa 155 | Thr | Phe | Val | Leu | Trp 160 |
| Lys | Thr | Cys | Xaa | Trp 165 | Ala | His | Xaa | Glu | Leu 170 | Cys | Ala | Pro | Ser | Val 175 | Leu |
| Arg | Asn | His | Asn 180 | Pro | Gly |   |   |   |   |   |   |   |   |   |   |

( 2 ) INFORMATION FOR SEQ ID NO:11:

( i ) SEQUENCE CHARACTERISTICS:
        ( A ) LENGTH: 817 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
ATCCCATGGC GCGCTTTGAG GATCCAACAC GGCGACCCTA CAAGCTACCT GATCTGTGCA      60
CGGAACTGAA CACTTCACTG CAAGACATAG AAATAACCTG TGTATATTGC AAGACAGTAT     120
TGGAACTTAC AGAGGTATTT GAATTTGCAT TTAAAGATTT ATTTGTGGTG TATAGAGACA     180
GTATACCCCA TGCTGCATGC CATAAATGTA TAGATTTTTA TTCTAGAATT AGAGAATTAA     240
GACATTATTC AGACTCTGTG TATGGAGACA CATTGGAAAA ACTAACTAAC ACTGGGTTAT     300
ACAATTTATT AATAAGGTGC CTGCGGTGCC AGAAACCGTT GAATCCAGCA GAAAAACTTA     360
GACACCTTAA TGAAAAACGA CGATTTCACA ACATAGCTGG CACTATAGA GGCCAGTGCC      420
ATTCGTGCTG CAACCGAGCA CGACAGGAAC GACTCCAACG ACGCAGAGAA ACACAAGTAT     480
AATATTAAGT ATGCATGGAC CTAAGGCAAC ATTGCAAGAC ATTGTATTGC ATTTAGAGCC     540
CCAAAATGAA ATTCCGGTTG ACCTTCTATG TCACGAGCAA TTAAGCGACT CAGAGGAAGA     600
AAACGATGAA ATAGATGGAG TTAATCATCA ACATTTACCA GCCCGACGAG CCGAACCACA     660
ACGTCACACA ATGTTGTGTA TGTGTTGTAA GTGTGAAGCC AGAATTGAGC TAGTAGTAGA     720
AAGCTCAGCA GACGACCTTC GAGCATTCCA GCAGCTGTTT CTGAACACCC TGTCCTTTGT     780
GTGTCCGTGG TGTGCATCCC AGCAGTAACC CGGGTGA                              817
```

( 2 ) INFORMATION FOR SEQ ID NO:12:

( i ) SEQUENCE CHARACTERISTICS:
        ( A ) LENGTH: 272 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein (B) LOCATION: 1..272
(D) OTHER INFORMATION: /note= "Xaa refers to stop codon in the open reading frame."

(xi) SEQUENCE DESCRIPTION: SEQ ID NO:12:

| Ile | Pro | Trp | Arg | Ala | Leu | Arg | Ile | Gln | His | Gly | Asp | Pro | Thr | Ser | Tyr |
|-----|-----|-----|-----|-----|-----|-----|-----|-----|-----|-----|-----|-----|-----|-----|-----|
| 1 | | | | 5 | | | | | 10 | | | | | 15 | |
| Leu | Ile | Cys | Ala | Arg | Asn | Xaa | Thr | Leu | His | Cys | Lys | Thr | Xaa | Lys | Xaa |
| | | | 20 | | | | 25 | | | | | 30 | | | |
| Pro | Val | Tyr | Ile | Ala | Arg | Gln | Tyr | Trp | Asn | Leu | Gln | Arg | Tyr | Leu | Asn |
| | | 35 | | | | 40 | | | | | | 45 | | | |
| Leu | His | Leu | Lys | Ile | Tyr | Leu | Trp | Cys | Ile | Glu | Thr | Val | Tyr | Pro | Met |
| | 50 | | | | | 55 | | | | | 60 | | | | |
| Leu | His | Ala | Ile | Asn | Val | Xaa | Ile | Phe | Ile | Leu | Glu | Leu | Glu | Asn | Xaa |
| 65 | | | | | 70 | | | | | 75 | | | | | 80 |
| Asp | Ile | Ile | Gln | Thr | Leu | Cys | Met | Glu | Thr | His | Trp | Lys | Asn | Xaa | Leu |
| | | | | 85 | | | | | 90 | | | | | 95 | |
| Thr | Leu | Gly | Tyr | Thr | Ile | Tyr | Xaa | Xaa | Gly | Ala | Cys | Gly | Ala | Arg | Asn |
| | | | 100 | | | | | 105 | | | | | 110 | | |
| Arg | Xaa | Ile | Gln | Gln | Lys | Asn | Leu | Asp | Thr | Leu | Met | Lys | Asn | Asp | Asp |
| | | 115 | | | | | 120 | | | | | 125 | | | |
| Phe | Thr | Thr | Xaa | Leu | Gly | Thr | Ile | Glu | Ala | Ser | Ala | Ile | Arg | Ala | Ala |
| | 130 | | | | | 135 | | | | | 140 | | | | |
| Thr | Glu | His | Asp | Arg | Asn | Asp | Ser | Asn | Asp | Ala | Glu | Lys | His | Lys | Tyr |
| 145 | | | | | 150 | | | | | 155 | | | | | 160 |
| Asn | Ile | Lys | Tyr | Ala | Trp | Thr | Xaa | Gly | Asn | Ile | Ala | Arg | His | Cys | Ile |
| | | | | 165 | | | | | 170 | | | | | 175 | |
| Ala | Phe | Arg | Ala | Pro | Lys | Xaa | Asn | Ser | Gly | Xaa | Pro | Ser | Met | Ser | Arg |
| | | | 180 | | | | | 185 | | | | | 190 | | |
| Ala | Ile | Lys | Arg | Leu | Arg | Gly | Arg | Lys | Arg | Xaa | Asn | Arg | Trp | Ser | Xaa |
| | | 195 | | | | 200 | | | | | 205 | | | | |
| Ser | Ser | Thr | Phe | Thr | Ser | Pro | Thr | Ser | Arg | Thr | Thr | Thr | Ser | His | Asn |
| | 210 | | | | | 215 | | | | | 220 | | | | |
| Val | Val | Tyr | Val | Leu | Xaa | Val | Xaa | Ser | Gln | Asn | Xaa | Ala | Ser | Ser | Arg |
| 225 | | | | | 230 | | | | | 235 | | | | | 240 |
| Lys | Leu | Ser | Arg | Arg | Pro | Ser | Ser | Ile | Pro | Ala | Ala | Val | Ser | Glu | His |
| | | | | 245 | | | | | 250 | | | | | 255 | |
| Pro | Val | Leu | Cys | Val | Ser | Val | Val | Cys | Ile | Pro | Ala | Val | Thr | Arg | Val |
| | | | 260 | | | | | 265 | | | | | 270 | | |

(2) INFORMATION FOR SEQ ID NO:13:

(i) SEQUENCE CHARACTERISTICS:
(A) LENGTH: 272 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..272
(D) OTHER INFORMATION: /note= "Xaa refers to stop codon in the open reading frame."

(xi) SEQUENCE DESCRIPTION: SEQ ID NO:13:

| Ser | His | Gly | Ala | Leu | Xaa | Gly | Ser | Asn | Thr | Ala | Thr | Leu | Gln | Ala | Thr |
|-----|-----|-----|-----|-----|-----|-----|-----|-----|-----|-----|-----|-----|-----|-----|-----|
| 1 | | | | 5 | | | | | 10 | | | | | 15 | |
| Xaa | Ser | Val | His | Gly | Thr | Glu | His | Phe | Thr | Ala | Arg | His | Arg | Asn | Asn |

-continued

|   |   |   | 20 |   |   |   | 25 |   |   |   | 30 |   |   |   |
|---|---|---|---|---|---|---|---|---|---|---|---|---|---|---|
| Leu | Cys | Ile<br>35 | Leu | Gln | Asp | Ser | Ile<br>40 | Gly | Thr | Tyr | Arg | Gly<br>45 | Ile | Xaa | Ile |
| Cys | Ile<br>50 | Xaa | Arg | Phe | Ile | Cys<br>55 | Gly | Val | Xaa | Arg | Gln<br>60 | Tyr | Thr | Pro | Cys |
| Cys<br>65 | Met | Pro | Xaa | Met<br>70 | Tyr | Arg | Phe | Leu | Phe | Xaa<br>75 | Asn | Xaa | Arg | Ile | Lys<br>80 |
| Thr | Leu | Phe | Arg | Leu<br>85 | Cys | Val | Trp | Arg | His<br>90 | Ile | Gly | Lys | Thr | Asn<br>95 | Xaa |
| His | Trp | Val | Ile<br>100 | Gln | Phe | Ile | Asn | Lys<br>105 | Val | Pro | Ala | Val | Pro<br>110 | Glu | Thr |
| Val | Glu | Ser<br>115 | Ser | Arg | Lys | Thr | Xaa<br>120 | Thr | Pro | Xaa | Xaa | Lys<br>125 | Thr | Thr | Ile |
| Ser | Gln<br>130 | His | Ser | Trp | Ala | Leu<br>135 | Xaa | Arg | Pro | Val | Pro<br>140 | Phe | Val | Leu | Gln |
| Pro<br>145 | Ser | Thr | Thr | Gly | Thr<br>150 | Thr | Pro | Thr | Thr | Gln<br>155 | Arg | Asn | Thr | Ser | Ile<br>160 |
| Ile | Leu | Ser | Met | His<br>165 | Gly | Pro | Lys | Ala | Thr<br>170 | Leu | Gln | Asp | Ile | Val<br>175 | Leu |
| His | Leu | Glu | Pro<br>180 | Gln | Asn | Glu | Ile | Pro<br>185 | Val | Asp | Leu | Leu | Cys<br>190 | His | Glu |
| Gln | Leu | Ser<br>195 | Asp | Ser | Glu | Glu | Glu<br>200 | Asn | Asp | Glu | Ile | Asp<br>205 | Gly | Val | Asn |
| His | Gln<br>210 | His | Leu | Pro | Ala | Arg<br>215 | Arg | Ala | Glu | Pro | Gln<br>220 | Arg | His | Thr | Met |
| Leu<br>225 | Cys | Met | Cys | Cys | Lys<br>230 | Cys | Glu | Ala | Arg | Ile<br>235 | Glu | Leu | Val | Val | Glu<br>240 |
| Ser | Ser | Ala | Asp | Asp<br>245 | Leu | Arg | Ala | Phe | Gln<br>250 | Gln | Leu | Phe | Leu | Asn<br>255 | Thr |
| Leu | Ser | Phe | Val | Cys<br>260 | Pro | Trp | Cys | Ala | Ser<br>265 | Gln | Gln | Xaa | Pro<br>270 | Gly | Xaa |

( 2 ) INFORMATION FOR SEQ ID NO:14:

( i ) SEQUENCE CHARACTERISTICS:
        ( A ) LENGTH: 271 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..271
        ( D ) OTHER INFORMATION: /note= "Xaa refers to stop codon in
           the open reading frame."

( x i ) SEQUENCE DESCRIPTION: SEQ ID NO:14:

| Pro<br>1 | Met | Ala | Arg | Phe<br>5 | Glu | Asp | Pro | Thr | Arg<br>10 | Arg | Pro | Tyr | Lys | Leu<br>15 | Pro |
|---|---|---|---|---|---|---|---|---|---|---|---|---|---|---|---|
| Asp | Leu | Cys | Thr<br>20 | Glu | Leu | Asn | Thr | Ser<br>25 | Leu | Gln | Asp | Ile | Glu<br>30 | Ile | Thr |
| Cys | Val | Tyr<br>35 | Cys | Lys | Thr | Val | Leu<br>40 | Glu | Leu | Thr | Glu | Val<br>45 | Phe | Glu | Phe |
| Ala | Phe<br>50 | Lys | Asp | Leu | Phe | Val<br>55 | Val | Tyr | Arg | Asp | Ser<br>60 | Ile | Pro | His | Ala |
| Ala<br>65 | Cys | His | Lys | Cys | Ile<br>70 | Asp | Phe | Tyr | Ser | Arg<br>75 | Ile | Arg | Glu | Leu | Arg<br>80 |

```
His Tyr Ser Asp Ser Val Tyr Gly Asp Thr Leu Glu Lys Leu Thr Asn
                85                  90                  95

Thr Gly Leu Tyr Asn Leu Leu Ile Arg Cys Leu Arg Cys Gln Lys Pro
            100                 105                 110

Leu Asn Pro Ala Glu Lys Leu Arg His Leu Asn Glu Lys Arg Arg Phe
        115                 120                 125

His Asn Ile Ala Gly His Tyr Arg Gly Gln Cys His Ser Cys Cys Asn
    130                 135                 140

Arg Ala Arg Gln Glu Arg Leu Gln Arg Arg Arg Glu Thr Gln Val Xaa
145                 150                 155                 160

Tyr Xaa Val Cys Met Asp Leu Arg Gln His Cys Lys Thr Leu Tyr Cys
                165                 170                 175

Ile Xaa Ser Pro Lys Met Lys Phe Arg Leu Thr Phe Tyr Val Thr Ser
            180                 185                 190

Asn Xaa Ala Thr Gln Arg Lys Lys Thr Met Lys Xaa Met Glu Leu Ile
        195                 200                 205

Ile Asn Ile Tyr Gln Pro Asp Glu Pro Asn His Asn Val Thr Gln Cys
    210                 215                 220

Cys Val Cys Val Val Ser Val Lys Pro Glu Leu Ser Xaa Xaa Xaa Lys
225                 230                 235                 240

Ala Gln Gln Thr Thr Phe Glu His Ser Ser Ser Cys Phe Xaa Thr Pro
                245                 250                 255

Cys Pro Leu Cys Val Arg Gly Val His Pro Ser Ser Asn Pro Gly
            260                 265                 270
```

( 2 ) INFORMATION FOR SEQ ID NO:15:

( i ) SEQUENCE CHARACTERISTICS:
        ( A ) LENGTH: 540 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
GATTGTGTGC ATGCGTGGTA GATGTTTGGA GAAATGAGAA ACTGTTTTCT AGATGGAAAT    60
ATTGTTTACG AGCTATTAAA CTGTTTATTA ATGATCACAT GCTTGATAAG ATAAAATCTA   120
TACTGCAGAA TAGACTAGTA TATGTGGAAA TGTCATAGAA AGTTAAAAGT TAATGAGAGC   180
AAAAATATAT AAGGTTGTAT TCCATATTTG TTATTTTTTC TGTAATAGTT AGAAAAATAC   240
ATTCGATGGT CTATCTACCA GATTATTATG TGTTATAAGG TACTTTTTCT CATAATAAAC   300
TAGAGTATGA GTAAGATAGT GTTTTTCAAA ACATATAAAT CTAAAATTGA TGGATGAGAT   360
ATACAGCTAT TAATTTCGAA AATATATTTT AATCTGATAA CTTTAAACAT GGATTTTTGA   420
TGGTGGTTTA ACGTTTTAAA AAAAGATTTT GTTATTGTAG TATATGATAA TATTAAAAGA   480
TGGATATAAA GAATTTGCTG ACTGCATGTA CTATTTTTTA CATTACTACA TTGGCTACGG   540
```

( 2 ) INFORMATION FOR SEQ ID NO:16:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: protein ( i x ) FEATURE:

( A ) NAME/KEY: Protein (B) LOCATION: 1..52
( D ) OTHER INFORMATION: /note= "Xaa refers to stop codon in
the open reading frame."

( x i ) SEQUENCE DESCRIPTION: SEQ ID NO:16:

| Leu | Cys | Ala | Cys | Val | Val | Asp | Val | Trp | Arg | Asn | Glu | Lys | Leu | Phe | Ser |
|---|---|---|---|---|---|---|---|---|---|---|---|---|---|---|---|
| 1 | | | | 5 | | | | | 10 | | | | | 15 | |

| Arg | Trp | Lys | Tyr | Cys | Leu | Arg | Ala | Ile | Lys | Leu | Phe | Ile | Asn | Asp | His |
|---|---|---|---|---|---|---|---|---|---|---|---|---|---|---|---|
| | | | 20 | | | | | 25 | | | | | 30 | | |

| Met | Leu | Asp | Lys | Ile | Lys | Ser | Ile | Leu | Gln | Asn | Arg | Leu | Val | Tyr | Val |
|---|---|---|---|---|---|---|---|---|---|---|---|---|---|---|---|
| | | 35 | | | | | 40 | | | | | 45 | | | |

Glu Met Ser Xaa
50

( 2 ) INFORMATION FOR SEQ ID NO:17:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:17:

| Met | Ile | Ile | Leu | Lys | Asp | Gly | Tyr | Lys | Glu | Phe | Ala | Asp | Cys | Met | Tyr |
|---|---|---|---|---|---|---|---|---|---|---|---|---|---|---|---|
| 1 | | | | 5 | | | | | 10 | | | | | 15 | |

| Tyr | Phe | Leu | His | Tyr | Tyr | Ile | Gly | Tyr | Gly |
|---|---|---|---|---|---|---|---|---|---|
| | | | 20 | | | | | 25 | |

( 2 ) INFORMATION FOR SEQ ID NO:18:

( i ) SEQUENCE CHARACTERISTICS:
( A ) LENGTH: 540 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:18:

| TGCCAAGGTT | AGATGTAATG | GTAACGATAA | CACAAAATGT | GAACGCTGCC | CACCTCATAC | 60 |
| ATATACCACA | ATCCCAATTA | TTCTAATGGA | TGTCATCAAT | GTAGAAAATG | CCCAACCGGA | 120 |
| TCATTTGATA | AGGTAAAGTG | TACCGGAACA | CAGAACAGTA | AATGTTCGTG | TCTTCCTGGT | 180 |
| TGGTATTGTG | CTACTGATTC | TTCACAGACT | GAAGATTGTT | GAAATTGTGT | ACCAAAAAGG | 240 |
| AGATGTCCAT | GCGGATACTT | TGGTGGAATA | GATGAACAAG | GAAATCCTAT | TTGTAAATCG | 300 |
| TGTTGTGTTG | GTGAATATTG | CGACTACCTA | CGTAATTATA | GACTTGATCC | ATTTCCTCCA | 360 |
| TGCAAACTAT | CTAAATGTAA | TTAATTATGA | TTTTGATGAT | AATGTTACCA | TACATTATAT | 420 |
| CGCTACTTGG | TTAGTGTATT | ATTCAGTATG | AAGACCTATT | AATAATTACT | TATCTTTTGA | 480 |
| CGATCTTGTT | ATAATTATAA | TATAAAAATA | CTTATGGCAT | AGTAACTCAT | AATTGCTGAC | 540 |

( 2 ) INFORMATION FOR SEQ ID NO:19:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( i i ) MOLECULE TYPE: protein ( i x ) FEATURE:

(A) NAME/KEY: Protein
(B) LOCATION: 1..45
(D) OTHER INFORMATION: /note= "Xaa refers to stop codon in the open reading frame."

(xi) SEQUENCE DESCRIPTION: SEQ ID NO:19:

| Ala | Lys | Val | Arg | Cys | Asn | Gly | Asn | Asp | Asn | Thr | Lys | Cys | Glu | Arg | Cys |
|---|---|---|---|---|---|---|---|---|---|---|---|---|---|---|---|
| 1 | | | | 5 | | | | | 10 | | | | | 15 | |

| Pro | Pro | His | Thr | Tyr | Thr | Thr | Ile | Pro | Ile | Ile | Leu | Met | Asp | Val | Ile |
|---|---|---|---|---|---|---|---|---|---|---|---|---|---|---|---|
| | | | 20 | | | | | 25 | | | | | 30 | | |

| Asn | Val | Glu | Asn | Ala | Gln | Pro | Asp | His | Leu | Ile | Arg | Xaa |
|---|---|---|---|---|---|---|---|---|---|---|---|---|
| | | 35 | | | | | 40 | | | | | 45 |

(2) INFORMATION FOR SEQ ID NO:20:

(i) SEQUENCE CHARACTERISTICS:
(A) LENGTH: 60 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..60
(D) OTHER INFORMATION: /note= "Xaa refers to stop codon in the open reading frame."

(xi) SEQUENCE DESCRIPTION: SEQ ID NO:20:

| Met | Asn | Lys | Glu | Ile | Leu | Phe | Val | Asn | Arg | Val | Val | Leu | Val | Asn | Ile |
|---|---|---|---|---|---|---|---|---|---|---|---|---|---|---|---|
| 1 | | | | 5 | | | | | 10 | | | | | 15 | |

| Ala | Thr | Thr | Tyr | Val | Ile | Ile | Asp | Leu | Ile | His | Phe | Leu | His | Ala | Asn |
|---|---|---|---|---|---|---|---|---|---|---|---|---|---|---|---|
| | | | 20 | | | | | 25 | | | | | 30 | | |

| Tyr | Leu | Asn | Val | Ile | Asn | Tyr | Asp | Phe | Asp | Asp | Asn | Val | Thr | Ile | His |
|---|---|---|---|---|---|---|---|---|---|---|---|---|---|---|---|
| | | 35 | | | | | 40 | | | | | 45 | | | |

| Tyr | Ile | Ala | Thr | Trp | Leu | Val | Tyr | Tyr | Ser | Val | Xaa |
|---|---|---|---|---|---|---|---|---|---|---|---|
| | 50 | | | | | 55 | | | | | 60 |

(2) INFORMATION FOR SEQ ID NO:21:

(i) SEQUENCE CHARACTERISTICS:
(A) LENGTH: 194 amino acids
(B) TYPE: amino acid
(C) STRANDEDNESS: double
(D) TOPOLOGY: linear (ii) MOLECULE TYPE: protein (xi) SEQUENCE DESCRIPTION: SEQ ID NO:21:

| Met | Ser | Gly | Ile | Val | Lys | Ser | Ile | Ile | Leu | Ser | Gly | Pro | Ser | Gly | Leu |
|---|---|---|---|---|---|---|---|---|---|---|---|---|---|---|---|
| 1 | | | | 5 | | | | | 10 | | | | | 15 | |

| Gly | Lys | Thr | Ala | Ile | Ala | Lys | Arg | Leu | Met | Gly | Ile | Tyr | Leu | Asp | Leu |
|---|---|---|---|---|---|---|---|---|---|---|---|---|---|---|---|
| | | | 20 | | | | | 25 | | | | | 30 | | |

| Trp | Cys | Pro | Ile | Pro | Leu | Asp | Phe | Leu | Val | Leu | Met | Glu | Arg | Glu | Gly |
|---|---|---|---|---|---|---|---|---|---|---|---|---|---|---|---|
| | | | 35 | | | | | 40 | | | | | 45 | | |

| Val | Asp | Tyr | His | Tyr | Val | Asn | Arg | Glu | Ala | Ile | Trp | Lys | Gly | Ile | Ala |
|---|---|---|---|---|---|---|---|---|---|---|---|---|---|---|---|
| | 50 | | | | | 55 | | | | | 60 | | | | |

| Ala | Gly | Asn | Phe | Leu | Glu | His | Thr | Glu | Phe | Leu | Gly | Asn | Ile | Tyr | Gly |
|---|---|---|---|---|---|---|---|---|---|---|---|---|---|---|---|
| 65 | | | | | 70 | | | | | 75 | | | | | 80 |

| Thr | Ser | Lys | Thr | Ala | Val | Asn | Thr | Ala | Ala | Ile | Asn | Asn | Arg | Ile | Cys |
|---|---|---|---|---|---|---|---|---|---|---|---|---|---|---|---|
| | | | | 85 | | | | | 90 | | | | | 95 | |

| Val | Met | Asp | Leu | Asn | Ile | Asp | Gly | Val | Arg | Ser | Leu | Lys | Asn | Thr | Tyr |
|---|---|---|---|---|---|---|---|---|---|---|---|---|---|---|---|
| | | | 100 | | | | | 105 | | | | | 110 | | |

|       |       |            |       |       |       |            |       |       |       |            |       |       |       |            |       |
|-------|-------|------------|-------|-------|-------|------------|-------|-------|-------|------------|-------|-------|-------|------------|-------|
| Leu   | Met   | Pro<br>115 | Tyr   | Ser   | Val   | Tyr<br>    | Ile<br>120 | Arg   | Pro   | Thr   | Ser        | Leu<br>125 | Lys   | Met   | Val   |
| Glu   | Thr<br>130 | Lys   | Leu   | Arg   | Cys   | Arg<br>135 | Asn   | Thr   | Glu   | Ala   | Asn<br>140 | Asp   | Glu   | Ile   | His   |
| Arg<br>145 | Arg   | Val   | Ile   | Leu   | Ala<br>150 | Lys   | Thr   | Asp   | Met   | Asp<br>155 | Glu   | Ala   | Asn   | Glu   | Ala<br>160 |
| Gly   | Leu   | Phe   | Asp   | Thr<br>165 | Ile   | Ile   | Ile   | Glu   | Asp<br>170 | Asp   | Val   | Asn   | Leu   | Ala<br>175 | Tyr   |
| Ser   | Lys   | Leu   | Ile<br>180 | Gln   | Ile   | Leu   | Gln   | Asp<br>185 | Arg   | Ile   | Arg   | Met   | Tyr<br>190 | Phe   | Asn   |
| Thr   | Asn   |            |       |       |       |            |       |       |       |            |       |       |       |            |       |

( 2 ) INFORMATION FOR SEQ ID NO:22:

( i ) SEQUENCE CHARACTERISTICS:
        ( A ) LENGTH: 186 amino acids
        ( B ) TYPE: amino acid
        ( C ) STRANDEDNESS: double
        ( D ) TOPOLOGY: linear ( i i ) MOLECULE TYPE: protein ( x i ) SEQUENCE DESCRIPTION: SEQ ID NO:22:

|       |       |            |       |       |       |            |       |       |       |            |       |       |       |            |       |
|-------|-------|------------|-------|-------|-------|------------|-------|-------|-------|------------|-------|-------|-------|------------|-------|
| Ser<br>1 | Arg   | Pro   | Ile   | Val<br>5 | Ile   | Ser   | Gly   | Pro   | Ser<br>10 | Gly   | Thr   | Gly   | Lys   | Ser<br>15 | Thr   |
| Leu   | Leu   | Lys   | Lys<br>20 | Leu   | Phe   | Ala   | Glu   | Tyr<br>25 | Pro   | Asp   | Ser   | Phe   | Gly<br>30 | Phe   | Ser   |
| Val   | Ser   | Ser<br>35 | Thr   | Thr   | Arg   | Thr   | Pro<br>40 | Arg   | Ala   | Gly   | Glu   | Val<br>45 | Asn   | Gly   | Lys   |
| Asp   | Tyr<br>50 | Asn   | Phe   | Val   | Ser   | Val<br>55 | Asp   | Glu   | Phe   | Lys   | Ser<br>60 | Met   | Ile   | Lys   | Asn   |
| Asn<br>65 | Glu   | Phe   | Ile   | Glu   | Trp<br>70 | Ala   | Gln   | Phe   | Ser   | Gly<br>75 | Asn   | Tyr   | Tyr   | Gly   | Ser<br>80 |
| Thr   | Val   | Ala   | Ser   | Val<br>85 | Lys   | Gln   | Val   | Ser   | Lys<br>90 | Ser   | Gly   | Lys   | Thr   | Cys<br>95 | Ile   |
| Leu   | Asp   | Ile   | Asp<br>100 | Met   | Gln   | Gly   | Val   | Lys<br>105 | Ser   | Val   | Lys   | Ala   | Ile<br>110 | Pro   | Glu   |
| Leu   | Asn   | Ala<br>115 | Arg   | Phe   | Leu   | Phe   | Ile<br>120 | Ala   | Pro   | Pro   | Ser   | Val<br>125 | Glu   | Asp   | Leu   |
| Lys   | Lys<br>130 | Arg   | Leu   | Glu   | Gly   | Arg<br>135 | Gly   | Thr   | Glu   | Thr   | Glu<br>140 | Glu   | Ser   | Ile   | Asn   |
| Lys<br>145 | Arg   | Leu   | Ser   | Ala   | Ala<br>150 | Gln   | Ala   | Glu   | Leu   | Ala<br>155 | Tyr   | Ala   | Glu   | Thr   | Gly<br>160 |
| Ala   | His   | Asp   | Lys   | Val<br>165 | Ile   | Val   | Asn   | Asp   | Asp<br>170 | Leu   | Asp   | Lys   | Ala   | Tyr<br>175 | Lys   |
| Glu   | Leu   | Lys   | Asp<br>180 | Phe   | Ile   | Phe   | Ala   | Glu<br>185 | Lys   |       |       |       |       |            |       |

( 2 ) INFORMATION FOR SEQ ID NO:23:

( i ) SEQUENCE CHARACTERISTICS:
        ( A ) LENGTH: 720 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:23:

-continued

```
CTAAGAACAC GTATACGGCA GCAGCTTCCT TTATACTCTC ATCTTTTACC AACACAAAGG      60
GTGGATATTT GTTCATTGGA GTTGATAATA ATACACACAA AGTAATTGGA TTCACGGTGG     120
GTCATGACTA CCTCAGACTG GTAGAGAATG ATATAGAAAA GCATATCAAA AGACTTCGTG     180
TTGTGCATTT CTGTGAGAAG AAAGAGGACA TCAAGTACAC GTGTCGATTC ATCAAGGTAT     240
ATAAACCTGG GGATGAGGCT ACCTCGACAT ACGTGTGCGC TATCAAAGTG GAAAGATGCT     300
GTTGTGCTGT GTTGCAGAT TGGCCAGAAT CATGGTATAT GGATACTAAT GGTATCAAGA      360
AGTATTCTCC AGATGAATGG GTGTCACATA TAAAATTTTA ATTAATGTAA TAGAGAACAA     420
ATAATAAGGT TGTAATATCA TATAGACAAT AACTAACAAT TAATTAGTAA CTGTTATCTC     480
TTTTTTAACT AACCAACTAA CTATATACCT ATTAATACAT CGTAATTATA GTTCTTAACA     540
TCTATTAATC ATTAATTCGC TTCTTTAATT TTTTATAAAC TAACATTGTT AATTGAAAAG     600
GGATAACATG TTACAGAATA TAAATTATAT ATGGATTTTT TTAAAAAGGA AATACTTGAC     660
TGGAGTATAT ATTTATCTCT TCATTATATA GCACGCGTGT TTTCCAATTT TTCCACATCC     720
```

( 2 ) INFORMATION FOR SEQ ID NO:24:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..35
        ( D ) OTHER INFORMATION: /note= "Xaa refers to stop codon in
        the open reading frame."

( x i ) SEQUENCE DESCRIPTION: SEQ ID NO:24:

```
Leu Arg Thr Arg Ile Arg Gln Gln Leu Pro Leu Tyr Ser His Leu Leu
 1               5                  10                 15

Pro Thr Gln Arg Val Asp Ile Cys Ser Leu Glu Leu Ile Ile Ile His
                20                 25                 30

Thr Lys Xaa
         35
```

( 2 ) INFORMATION FOR SEQ ID NO:25:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Met Asp Phe Phe Lys Lys Glu Ile Leu Asp Trp Ser Ile Tyr Leu Ser
 1               5                  10                 15

Leu His Tyr Ile Ala Arg Val Phe Ser Asn Phe Ser Thr Ser
                20                 25                 30
```

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

TCAGGATCCC ACATGAGCGA AAAATACATC G    31

( 2 ) INFORMATION FOR SEQ ID NO:27:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

TCAAAGCTTA TTACGATACA AACTTAACGG A    31

( 2 ) INFORMATION FOR SEQ ID NO:28:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

TCAGTTAACA TAAAAAGAAC AACGCCCGGC AG    32

( 2 ) INFORMATION FOR SEQ ID NO:29:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

TCAAGGGCCT CTATATAGTA ATACCAATAC TC    32

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

TCAGTCGACT TACAAACAAC TAGGAAATTG G    31

( 2 ) INFORMATION FOR SEQ ID NO:31:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

TCAGAATTCT ATGTACAGAG GTCTATTAGG C    31

( 2 ) INFORMATION FOR SEQ ID NO:32:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:32:

TCAAAGCTTG TATGAGGTGG GCAGCGTTCA C    31

( 2 ) INFORMATION FOR SEQ ID NO:33:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:33:

TCAGAATTCT TAATTATATT GTCGGCCGTG G    31

( 2 ) INFORMATION FOR SEQ ID NO:34:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:34:

TCAGCATGCA TGATCCGTTA GCTTTGGGCT C    31

( 2 ) INFORMATION FOR SEQ ID NO:35:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:35:

TCAGAATTCG AAGCTCTAGA GTATCTTAGC G    31

( 2 ) INFORMATION FOR SEQ ID NO:36:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:36:

TCAAAGCTTT CCTGTATTAT ATGGGATGTG G    31

( 2 ) INFORMATION FOR SEQ ID NO:37:

( i ) SEQUENCE CHARACTERISTICS:

(A) LENGTH: 31 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:37:

TCAGAATTCA TTGATGGATG AGATATACAG C    31

(2) INFORMATION FOR SEQ ID NO:38:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:38:

TCAAAGCTTT CACAAAATCG    20

(2) INFORMATION FOR SEQ ID NO:39:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:39:

TCAGAATTCC ACGTATACGG CAGCAGCTTC C    31

(2) INFORMATION FOR SEQ ID NO:40:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:40:

TCAAAGCTTT GTTCTACGTC CATTTTCAAG C    31

(2) INFORMATION FOR SEQ ID NO:41:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:41:

TCAGTCGACA TACCAATACT CAAGACTACG A    31

(2) INFORMATION FOR SEQ ID NO:42:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (  i  i  ) MOLECULE TYPE: cDNA (  x  i  ) SEQUENCE DESCRIPTION: SEQ ID NO:42:

TCACCATGGA TTGCTATTGA TTGAGTACTG TTC        33

( 2 ) INFORMATION FOR SEQ ID NO:43:

(  i  ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear (  i  i  ) MOLECULE TYPE: cDNA (  x  i  ) SEQUENCE DESCRIPTION: SEQ ID NO:43:

AGTACCTTAT AATACGTAAT AATCTGGTAG        30

( 2 ) INFORMATION FOR SEQ ID NO:44:

(  i  ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear (  i  i  ) MOLECULE TYPE: cDNA (  x  i  ) SEQUENCE DESCRIPTION: SEQ ID NO:44:

AATCTTCAGT CTGTTAACAA TCAGTAGCAC        30

( 2 ) INFORMATION FOR SEQ ID NO:45:

(  i  ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear (  i  i  ) MOLECULE TYPE: cDNA (  x  i  ) SEQUENCE DESCRIPTION: SEQ ID NO:45:

TACAACGAAG CTAGGCCTCA ACCATTTTAA        30

( 2 ) INFORMATION FOR SEQ ID NO:46:

(  i  ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear (  i  i  ) MOLECULE TYPE: cDNA (  x  i  ) SEQUENCE DESCRIPTION: SEQ ID NO:46:

TTTGATAGCG CATACGTATG TCGAGGTAGC        30

( 2 ) INFORMATION FOR SEQ ID NO:47:

(  i  ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear (  i  i  ) MOLECULE TYPE: cDNA (  x  i  ) SEQUENCE DESCRIPTION: SEQ ID NO:47:

AATAGGTATA TAGTTAACTG GTTAGTTAAA        30

( 2 ) INFORMATION FOR SEQ ID NO:48:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

ATCCCATGGC GCGCTTTGAG GATCCAAC  28

( 2 ) INFORMATION FOR SEQ ID NO:49:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

TCACCCGGGT TACTGCTGGG ATGCACACCA C  31

( 2 ) INFORMATION FOR SEQ ID NO:50:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

ATCCCATGGA CCAAAAGAGA ACTGCAATGT TTC  33

( 2 ) INFORMATION FOR SEQ ID NO:51:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

TCACCCGGGT TATGGTTTCT GAGAACAGAT G  31

( 2 ) INFORMATION FOR SEQ ID NO:52:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

AGCTCTACGT AGTTAACAAG CTTGTCGACC CATGGCCCGG GTACGTA  47

( 2 ) INFORMATION FOR SEQ ID NO:53:

( i ) SEQUENCE CHARACTERISTICS:

(A) LENGTH: 47 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:53:

AATTTACGTA CCCGGGCCAT GGGTCGACAA GCTTGTTAAC TACGTAG     47

(2) INFORMATION FOR SEQ ID NO:54:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:54:

GAAACCCAGC TGGGAATCAT GCATGG     26

(2) INFORMATION FOR SEQ ID NO:55:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:55:

GAAACACAAG TAGGAATATT AAGTATG     27

(2) INFORMATION FOR SEQ ID NO:56:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:56:

GATCTCTACG GTTATGGGCA ATTAAATGAC     30

(2) INFORMATION FOR SEQ ID NO:57:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:57:

GACCTTCTAG GTCACGGGCA ATTAAGCGAC     30

(2) INFORMATION FOR SEQ ID NO:58:

(i) SEQUENCE CHARACTERISTICS:
(A) LENGTH: 36 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:58:

ATGTATAGAT TTCTACAGTA GAATCAGAGA ATTAAG     36

( 2 ) INFORMATION FOR SEQ ID NO:59:

( i ) SEQUENCE CHARACTERISTICS:
        ( A ) LENGTH: 1250 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:59:

| | | | | | | |
|---|---|---|---|---|---|---|
| TATTGTTTAC | GAGCTATTAA | ACTGTTATT | AATGATCACA | TGCTTGATAA | GATAAAATCT | 60 |
| ATACTGCAGA | ATAGACTAGT | ATATGTGGAA | ATGTCATAGA | AAGTTAAAAG | TTAATGAGAG | 120 |
| CAAAAATATA | TAAGGTTGTA | TTCCATATTT | GTTATTTTTT | CTGTAATAGT | TAGAAAAATA | 180 |
| CATTCGATGG | TCTATCTACC | AGATTATTAT | GTGTTATAAG | GTACTTTTC | TCATAATAAA | 240 |
| CTAGAGTATG | AGTAAGATAG | TGTTTTTCAA | AACATATAAA | TCTAAAATTG | ATGGATGAGA | 300 |
| TATACAGCTA | TTAATTTCGA | AAATATATTT | TAATCTGATA | ACTTTAAACA | TGGATTTTTG | 360 |
| ATGGTGGTTT | AACGTTTTAA | AAAAAGATTT | TGTTATTGTA | GTATATGATA | ATATTAAAAG | 420 |
| ATGGATATAA | AGAATTTGCT | GACTGCATGT | ACTATTTTTT | ACATTACTAC | ATTGGCTACG | 480 |
| GCAGATATAC | CTACTCCGCC | ACCAACGGGT | CATGTGACAA | GGGAGAATAT | CTTGATAAGA | 540 |
| GGCATAATCA | ATGTTGTAAT | CGGTGTCCAC | CTGGAGAATT | TGCCAAGGTT | AGATGTAATG | 600 |
| GTAACGATAA | CACAAAATGT | GAACGCTGCC | CACCTCATAC | ATATACCACA | ATCCCAATTA | 660 |
| TTCTAATGGA | TGTCATCAAT | GTAGAAAATG | CCCAACCGGA | TCATTTGATA | AGGTAAAGTG | 720 |
| TACCGGAACA | CAGAACAGTA | AATGTTCGTG | TCTTCCTGGT | TGGTATTGTG | CTACTGATTC | 780 |
| TTCACAGACT | GAAGATTGTT | GAAATTGTGT | ACCAAAAAGG | AGATGTCCAT | GCGGATACTT | 840 |
| TGGTGGAATA | GATGAACAAG | GAAATCCTAT | TTGTAAATCG | TGTTGTGTTG | GTGAATATTG | 900 |
| CGACTACCTA | CGTAATTATA | GACTTGATCC | ATTTCCTCCA | TGCAAACTAT | CTAAATGTAA | 960 |
| TTAATTATGA | TTTTGATGAT | AATGTTACCA | TACATTATAT | CGCTACTTGG | TTAGTGTATT | 1020 |
| ATTCAGTATG | AAGACCTATT | AATAATTACT | TATCTTTTGA | CGATCTTGTT | ATAATTATAA | 1080 |
| TATAAAAATA | CTTATGGCAT | AGTAACTCAT | AATTGCTGAC | GCGATAAATT | CGTAATAATC | 1140 |
| TGTTTTGTTC | AAATTTTTAT | AAGGAATCTA | CAGGCATAAA | AATAAAAATA | TAATTTATAA | 1200 |
| TATACTCTTA | CAGCGCGCCA | TCATGAATAA | CAGCAGTGAA | TTGATTGCTG | | 1250 |

( 2 ) INFORMATION FOR SEQ ID NO:60:

( i ) SEQUENCE CHARACTERISTICS:
        ( A ) LENGTH: 416 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..416
        ( D ) OTHER INFORMATION: /note= "Xaa refers to stop codon in
            the open reading frame."

( x i ) SEQUENCE DESCRIPTION: SEQ ID NO:60:

| | | | | | | | | | | | | | | |
|---|---|---|---|---|---|---|---|---|---|---|---|---|---|---|
| Tyr<br>1 | Cys | Leu | Arg | Ala<br>5 | Ile | Lys | Leu | Phe | Ile<br>10 | Asn | Asp | His | Met | Leu<br>15 | Asp |
| Lys | Ile | Lys | Ser<br>20 | Ile | Leu | Gln | Asn | Arg<br>25 | Leu | Val | Tyr | Val | Glu<br>30 | Met | Ser |
| Xaa | Lys | Val<br>35 | Lys | Ser | Xaa | Xaa<br>40 | Glu | Gln | Lys | Tyr | Ile<br>45 | Arg | Leu | Tyr | Ser |
| Ile | Phe<br>50 | Val | Ile | Phe | Ser | Val<br>55 | Ile | Val | Arg | Lys | Ile<br>60 | His | Ser | Met | Val |
| Tyr<br>65 | Leu | Pro | Asp | Tyr<br>70 | Tyr | Val | Leu | Xaa | Gly<br>75 | Thr | Phe | Ser | His | Asn | Lys<br>80 |
| Leu | Glu | Tyr | Glu | Xaa<br>85 | Asp | Ser | Val | Phe | Gln<br>90 | Asn | Ile | Xaa | Ile | Xaa<br>95 | Asn |
| Xaa | Trp | Met | Arg<br>100 | Tyr | Thr | Ala | Ile | Asn<br>105 | Phe | Glu | Asn | Ile | Phe<br>110 | Xaa | Ser |
| Asp | Asn | Phe<br>115 | Lys | His | Gly | Phe | Leu<br>120 | Met | Val | Val | Xaa | Arg<br>125 | Phe | Lys | Lys |
| Arg | Phe<br>130 | Cys | Tyr | Cys | Ser | Ile<br>135 | Xaa | Xaa | Tyr | Xaa | Lys<br>140 | Met | Asp | Ile | Lys |
| Asn<br>145 | Leu | Leu | Thr | Ala | Cys<br>150 | Thr | Ile | Phe | Tyr | Ile<br>155 | Thr | Thr | Leu | Ala | Thr<br>160 |
| Ala | Asp | Ile | Pro | Thr<br>165 | Pro | Pro | Pro | Thr | Gly<br>170 | His | Val | Thr | Arg | Glu<br>175 | Asn |
| Ile | Leu | Ile | Arg<br>180 | Gly | Ile | Ile | Asn | Val<br>185 | Val | Ile | Gly | Val | His<br>190 | Leu | Glu |
| Asn | Leu | Pro<br>195 | Arg | Leu | Asp | Val | Met<br>200 | Val | Thr | Ile | Thr | Gln<br>205 | Asn | Val | Asn |
| Ala | Ala<br>210 | His | Leu | Ile | His | Ile<br>215 | Pro | Gln | Ser | Gln | Leu<br>220 | Phe | Xaa | Trp | Met |
| Ser<br>225 | Ser | Met | Xaa | Lys | Met<br>230 | Pro | Asn | Arg | Ile | Ile<br>235 | Xaa | Xaa | Gly | Lys | Val<br>240 |
| Tyr | Arg | Asn | Thr | Glu<br>245 | Gln | Xaa | Met | Phe | Val<br>250 | Ser | Ser | Trp | Leu | Val<br>255 | Leu |
| Cys | Tyr | Xaa | Phe<br>260 | Phe | Thr | Asp | Xaa | Arg<br>265 | Leu | Leu | Lys | Leu | Cys<br>270 | Thr | Lys |
| Lys | Glu | Met<br>275 | Ser | Met | Arg | Ile | Leu<br>280 | Trp | Trp | Asn | Arg | Xaa<br>285 | Thr | Arg | Lys |
| Ser | Tyr<br>290 | Leu | Xaa | Ile | Val | Leu<br>295 | Cys | Trp | Xaa | Ile | Leu<br>300 | Arg | Leu | Pro | Thr |
| Xaa<br>305 | Leu | Xaa | Thr | Xaa | Ser<br>310 | Ile | Ser | Ser | Met | Gln<br>315 | Thr | Ile | Xaa | Met | Xaa<br>320 |
| Leu | Ile | Met | Ile | Leu<br>325 | Met | Ile | Met | Leu | Pro<br>330 | Tyr | Ile | Ile | Ser | Leu<br>335 | Leu |
| Gly | Xaa | Cys | Ile<br>340 | Ile | Gln | Tyr | Glu | Asp<br>345 | Leu | Leu | Ile | Ile | Thr<br>350 | Tyr | Leu |
| Leu | Thr | Ile<br>355 | Leu | Leu | Xaa | Leu | Xaa<br>360 | Tyr | Lys | Asn | Thr | Tyr<br>365 | Gly | Ile | Val |
| Thr | His<br>370 | Asn | Cys | Xaa | Arg | Asp<br>375 | Lys | Phe | Val | Ile | Ile<br>380 | Cys | Phe | Val | Gln |
| Ile<br>385 | Phe | Ile | Arg | Asn | Leu<br>390 | Gln | Ala | Xaa | Lys | Xaa<br>395 | Lys | Tyr | Asn | Leu | Xaa<br>400 |
| Tyr | Thr | Leu | Thr | Ala<br>405 | Arg | His | His | Glu | Xaa<br>410 | Gln | Gln | Xaa | Ile | Asp<br>415 | Cys |

( 2 ) INFORMATION FOR SEQ ID NO:61:

( i ) SEQUENCE CHARACTERISTICS:
    ( A ) LENGTH: 416 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..416
    ( D ) OTHER INFORMATION: /note= "Xaa refers to stop codon in the open reading frame."

( x i ) SEQUENCE DESCRIPTION: SEQ ID NO:61:

```
Ile Val Tyr Glu Leu Leu Asn Cys Leu Leu Met Ile Thr Cys Leu Ile
 1               5                  10                  15

Arg Xaa Asn Leu Tyr Cys Arg Ile Asp Xaa Tyr Met Trp Lys Cys His
                20                  25                  30

Arg Lys Leu Lys Val Asn Glu Ser Lys Asn Ile Xaa Gly Cys Ile Pro
            35                  40                  45

Tyr Leu Leu Phe Phe Leu Xaa Xaa Leu Glu Lys Tyr Ile Arg Trp Ser
        50                  55                  60

Ile Tyr Gln Ile Ile Met Cys Tyr Lys Val Leu Phe Leu Ile Ile Asn
 65                  70                  75                  80

Xaa Ser Met Ser Lys Ile Val Phe Phe Lys Thr Tyr Lys Ser Lys Ile
                85                  90                  95

Asp Gly Xaa Asp Ile Gln Leu Leu Ile Ser Lys Ile Tyr Phe Asn Leu
                100                 105                 110

Ile Thr Leu Asn Met Asp Phe Xaa Trp Trp Phe Asn Val Leu Lys Lys
            115                 120                 125

Asp Phe Val Ile Val Val Tyr Asp Asn Ile Lys Arg Trp Ile Xaa Arg
        130                 135                 140

Ile Cys Xaa Leu His Val Leu Phe Phe Thr Leu Leu His Trp Leu Arg
145                 150                 155                 160

Gln Ile Tyr Leu Leu Arg His Gln Arg Val Met Xaa Gln Gly Arg Ile
                165                 170                 175

Ser Xaa Xaa Glu Ala Xaa Ser Met Leu Xaa Ser Val Ser Thr Trp Arg
                180                 185                 190

Ile Cys Gln Gly Xaa Met Xaa Trp Xaa Arg Xaa His Lys Met Xaa Thr
            195                 200                 205

Leu Pro Thr Ser Tyr Ile Tyr His Asn Pro Asn Tyr Ser Asn Gly Cys
        210                 215                 220

His Gln Cys Arg Lys Cys Pro Thr Gly Ser Phe Asp Lys Val Lys Cys
225                 230                 235                 240

Thr Gly Thr Gln Asn Ser Lys Cys Ser Cys Leu Pro Gly Trp Tyr Cys
                245                 250                 255

Ala Thr Asp Ser Ser Gln Thr Glu Asp Cys Xaa Asn Cys Val Pro Lys
                260                 265                 270

Arg Arg Cys Pro Cys Gly Tyr Phe Gly Gly Ile Asp Glu Gln Gly Asn
            275                 280                 285

Pro Ile Cys Lys Ser Cys Cys Val Gly Glu Tyr Cys Asp Tyr Leu Arg
        290                 295                 300

Asn Tyr Arg Leu Asp Pro Phe Pro Pro Cys Lys Leu Ser Lys Cys Asn
305                 310                 315                 320

Xaa Leu Xaa Phe Xaa Xaa Xaa Cys Tyr His Thr Leu Tyr Arg Tyr Leu
                325                 330                 335
```

| Val | Ser | Val | Leu | Phe | Ser | Met | Lys | Thr | Tyr | Xaa | Xaa | Leu | Leu | Ile | Phe |
| --- | --- | --- | --- | --- | --- | --- | --- | --- | --- | --- | --- | --- | --- | --- | --- |
| | | | 340 | | | | 345 | | | | | | 350 | | |
| Xaa | Arg | Ser | Cys | Tyr | Asn | Tyr | Asn | Ile | Lys | Ile | Leu | Met | Ala | Xaa | Xaa |
| | | 355 | | | | | 360 | | | | | 365 | | | |
| Leu | Ile | Ile | Ala | Asp | Ala | Ile | Asn | Ser | Xaa | Xaa | Ser | Val | Leu | Phe | Lys |
| | 370 | | | | 375 | | | | | | 380 | | | | |
| Phe | Leu | Xaa | Gly | Ile | Tyr | Arg | His | Lys | Asn | Lys | Asn | Ile | Ile | Tyr | Asn |
| 385 | | | | | 390 | | | | 395 | | | | | | 400 |
| Ile | Leu | Leu | Gln | Arg | Ala | Ile | Met | Asn | Asn | Ser | Ser | Glu | Leu | Ile | Ala |
| | | | | 405 | | | | | 410 | | | | | 415 | |

( 2 ) INFORMATION FOR SEQ ID NO:62:

( i ) SEQUENCE CHARACTERISTICS:
        ( A ) LENGTH: 416 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..416
        ( D ) OTHER INFORMATION: /note= "Xaa refers to stop codon in
            the open reading frame."

( x i ) SEQUENCE DESCRIPTION: SEQ ID NO:62:

| Leu | Phe | Thr | Ser | Tyr | Xaa | Thr | Val | Tyr | Xaa | Xaa | Ser | His | Ala | Xaa | Xaa |
| --- | --- | --- | --- | --- | --- | --- | --- | --- | --- | --- | --- | --- | --- | --- | --- |
| 1 | | | | 5 | | | | | 10 | | | | | 15 | |
| Asp | Lys | Ile | Tyr | Thr | Ala | Glu | Xaa | Thr | Ser | Ile | Cys | Gly | Asn | Val | Ile |
| | | | 20 | | | | | 25 | | | | | 30 | | |
| Glu | Ser | Xaa | Lys | Leu | Met | Arg | Ala | Lys | Ile | Tyr | Lys | Val | Val | Phe | His |
| | | 35 | | | | | 40 | | | | | 45 | | | |
| Ile | Cys | Tyr | Phe | Phe | Cys | Asn | Ser | Xaa | Lys | Asn | Thr | Phe | Asp | Gly | Leu |
| | 50 | | | | | 55 | | | | | 60 | | | | |
| Ser | Thr | Arg | Leu | Leu | Cys | Val | Ile | Arg | Tyr | Phe | Phe | Ser | Xaa | Xaa | Thr |
| 65 | | | | | 70 | | | | | 75 | | | | | 80 |
| Arg | Val | Xaa | Val | Arg | Xaa | Cys | Phe | Ser | Lys | His | Ile | Asn | Leu | Lys | Leu |
| | | | | 85 | | | | | 90 | | | | | 95 | |
| Met | Asp | Glu | Ile | Tyr | Ser | Tyr | Xaa | Phe | Arg | Lys | Tyr | Ile | Leu | Ile | Xaa |
| | | | 100 | | | | | 105 | | | | | 110 | | |
| Xaa | Leu | Xaa | Thr | Trp | Ile | Phe | Asp | Gly | Gly | Leu | Thr | Phe | Xaa | Lys | Lys |
| | | 115 | | | | | 120 | | | | | 125 | | | |
| Ile | Leu | Leu | Leu | Xaa | Tyr | Met | Ile | Ile | Leu | Lys | Asp | Gly | Tyr | Lys | Glu |
| | 130 | | | | | 135 | | | | | 140 | | | | |
| Phe | Ala | Asp | Cys | Met | Tyr | Tyr | Phe | Leu | His | Tyr | Tyr | Ile | Gly | Tyr | Gly |
| 145 | | | | | 150 | | | | | 155 | | | | | 160 |
| Arg | Tyr | Thr | Tyr | Ser | Ala | Thr | Asn | Gly | Ser | Cys | Asp | Lys | Gly | Glu | Tyr |
| | | | | 165 | | | | | 170 | | | | | 175 | |
| Leu | Asp | Lys | Arg | His | Asn | Gln | Cys | Cys | Asn | Arg | Cys | Pro | Pro | Gly | Glu |
| | | | 180 | | | | | 185 | | | | | 190 | | |
| Phe | Ala | Lys | Val | Arg | Cys | Asn | Gly | Asn | Asp | Asn | Thr | Lys | Cys | Glu | Arg |
| | | 195 | | | | | 200 | | | | | 205 | | | |
| Cys | Pro | Pro | His | Thr | Tyr | Thr | Thr | Ile | Pro | Ile | Ile | Leu | Met | Asp | Val |
| | 210 | | | | | 215 | | | | | 220 | | | | |
| Ile | Asn | Val | Glu | Asn | Ala | Gln | Pro | Asp | His | Leu | Ile | Arg | Xaa | Ser | Val |
| 225 | | | | | 230 | | | | | 235 | | | | | 240 |
| Pro | Glu | His | Arg | Thr | Val | Asn | Val | Arg | Val | Phe | Leu | Val | Gly | Ile | Val |

```
                          245                      250                          255
       Leu  Leu  Ile  Leu  His  Arg  Leu  Lys  Ile  Val  Glu  Ile  Val  Tyr  Gln  Lys
                      260                      265                      270

Gly  Asp  Val  His  Ala  Asp  Thr  Leu  Val  Glu  Xaa  Met  Asn  Lys  Glu  Ile
                 275                      280                      285

Leu  Phe  Val  Asn  Arg  Val  Val  Leu  Val  Asn  Ile  Ala  Thr  Thr  Tyr  Val
            290                      295                      300

Ile  Ile  Asp  Leu  Ile  His  Phe  Leu  His  Ala  Asn  Tyr  Leu  Asn  Val  Ile
       305                      310                      315                      320

Asn  Tyr  Asp  Phe  Asp  Asp  Asn  Val  Thr  Ile  His  Tyr  Ile  Ala  Thr  Trp
                           325                      330                      335

Leu  Val  Tyr  Tyr  Ser  Val  Xaa  Arg  Pro  Ile  Asn  Asn  Tyr  Leu  Ser  Phe
                      340                      345                      350

Asp  Asp  Leu  Val  Ile  Ile  Ile  Xaa  Lys  Tyr  Leu  Trp  His  Ser  Asn
                 355                      360                      365

Ser  Xaa  Leu  Leu  Thr  Arg  Xaa  Ile  Arg  Asn  Asn  Leu  Phe  Cys  Ser  Asn
            370                      375                      380

Phe  Tyr  Lys  Glu  Ser  Thr  Gly  Ile  Lys  Ile  Lys  Ile  Xaa  Phe  Ile  Ile
       385                      390                      395                      400

Tyr  Ser  Tyr  Ser  Ala  Pro  Ser  Xaa  Ile  Thr  Ala  Val  Asn  Xaa  Leu  Leu
                           405                      410                      415
```

( 2 ) INFORMATION FOR SEQ ID NO:63:

( i ) SEQUENCE CHARACTERISTICS:
        ( A ) LENGTH: 1000 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:63:

```
ATATTTGGTA  TTACCGCATT  AATTATATTG  TCGGCCGTGG  CAATTTCTG   TATTACATAT    60
TATATATATA  ATAAACGTTC  ACGTAAATAC  AAAACAGAGA  ACAAAGTCTA  GATTTTTGAC   120
TTACATAAAT  GTCTGGGATA  GTAAAATCTA  TCATATTGAG  CGGACCATCT  GGTTTAGGAA   180
AGACAGCCAT  AGCCAAAAGA  CTATGGGAAT  ATATTTGGAT  TTGTGGTGTC  CCATACCACT   240
AGATTTCCTC  GTCCTATGGA  ACGAGAAGGT  GTTGATTACC  ATTACGTTAA  CAGAGAGGCC   300
ATCTGGAAGG  GAATAGCCGC  CGGAAACTTT  CTAGAACATA  CTGAGTTTTT  AGGAAATATT   360
TACGGAACTT  CTAAAACAGC  TGTGAATACA  GCGGCTATTA  ATAATCGTAT  TTGTGTGATG   420
GATCTAAACA  TCGACGGTGT  TAGAAGTCTT  AAAAATACGT  ACCTAATGCC  TTACTCGGTG   480
TATATAAGAC  CTACCTCTCT  TAAAATGGTT  GAGACCAAGC  TTCGTTGTAG  AAACACTGAA   540
GCTAACGATG  AGATTCATCG  TCGCGTGATA  TTGGCAAAAA  CGGATATGGA  TGAGGCCAAC   600
GAAGCAGGTC  TATTCGACAC  TATTATCATT  GAAGATGATG  TGAATTTAGC  ATATAGTAAG   660
TTAATTCAGA  TACTACAGGA  CCGTATTAGA  ATGTATTTTA  ACACTAATTA  GAGACTTAAG   720
ACTTAAAACT  TGATAATTAA  TAATATAACT  CGTTTTTATA  TGTGGCTATT  TCAACGTCTA   780
ATGTATTAGT  TAAATATTAA  AACTTACCAC  GTAAAACTTA  AAATTTAAAA  TGATATTTCA   840
TTGACAGATA  GATCACACAT  TATGAACTTT  CAAGGACTTG  TGTTAACTGA  CAATTGCAAA   900
AATCAATGGG  TCGTTGGACC  ATTAATAGGA  AAAGGTGGAT  TCGGTAGTAT  TTATACTACT   960
AATGACAATA  ATTATGTAGT  AAAAATAGAG  CCCAAAGCTA                         1000
```

( 2 ) INFORMATION FOR SEQ ID NO:64:

( i ) SEQUENCE CHARACTERISTICS:
    ( A ) LENGTH: 333 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: Protein
    ( B ) LOCATION: 1..333
    ( D ) OTHER INFORMATION: /note= "Xaa refers to stop codon in
      the open reading frame."

( x i ) SEQUENCE DESCRIPTION: SEQ ID NO:64:

| | | | | | | | | | | | | | | |
|---|---|---|---|---|---|---|---|---|---|---|---|---|---|---|
| Ile | Phe | Gly | Ile | Thr | Ala | Leu | Ile | Ile | Leu | Ser | Ala | Val | Ala | Ile | Phe |
| 1 | | | | 5 | | | | | 10 | | | | | 15 | |
| Cys | Ile | Thr | Tyr | Tyr | Ile | Tyr | Asn | Lys | Arg | Ser | Arg | Lys | Tyr | Lys | Thr |
| | | | 20 | | | | | 25 | | | | | 30 | | |
| Glu | Asn | Lys | Val | Xaa | Ile | Phe | Asp | Leu | His | Lys | Cys | Leu | Gly | Xaa | Xaa |
| | | | 35 | | | | 40 | | | | | 45 | | | |
| Asn | Leu | Ser | Tyr | Xaa | Ala | Asp | His | Leu | Val | Xaa | Glu | Arg | Gln | Pro | Xaa |
| | 50 | | | | | 55 | | | | | 60 | | | | |
| Pro | Lys | Asp | Tyr | Gly | Asn | Ile | Phe | Gly | Phe | Val | Val | Ser | His | Thr | Thr |
| 65 | | | | | 70 | | | | | 75 | | | | | 80 |
| Arg | Phe | Pro | Arg | Pro | Met | Glu | Arg | Glu | Gly | Val | Asp | Tyr | His | Tyr | Val |
| | | | | 85 | | | | | 90 | | | | | 95 | |
| Asn | Arg | Glu | Ala | Ile | Trp | Lys | Gly | Ile | Ala | Ala | Gly | Asn | Phe | Leu | Glu |
| | | | | 100 | | | | | 105 | | | | | 110 | |
| His | Thr | Glu | Phe | Leu | Gly | Asn | Ile | Tyr | Gly | Thr | Ser | Lys | Thr | Ala | Val |
| | | | | 115 | | | | | 120 | | | | | 125 | |
| Asn | Thr | Ala | Ala | Ile | Asn | Asn | Arg | Ile | Cys | Val | Met | Asp | Leu | Asn | Ile |
| | 130 | | | | | 135 | | | | | 140 | | | | |
| Asp | Gly | Val | Arg | Ser | Leu | Lys | Asn | Thr | Tyr | Leu | Met | Pro | Tyr | Ser | Val |
| 145 | | | | | 150 | | | | | 155 | | | | | 160 |
| Tyr | Ile | Arg | Pro | Thr | Ser | Leu | Lys | Met | Val | Glu | Thr | Lys | Leu | Arg | Cys |
| | | | | 165 | | | | | 170 | | | | | 175 | |
| Arg | Asn | Thr | Glu | Ala | Asn | Asp | Glu | Ile | His | Arg | Arg | Val | Ile | Leu | Ala |
| | | | | 180 | | | | | 185 | | | | | 190 | |
| Lys | Thr | Asp | Met | Asp | Glu | Ala | Asn | Glu | Ala | Gly | Leu | Phe | Asp | Thr | Ile |
| | | 195 | | | | | 200 | | | | | 205 | | | |
| Ile | Ile | Glu | Asp | Asp | Val | Asn | Leu | Ala | Tyr | Ser | Lys | Leu | Ile | Gln | Ile |
| | 210 | | | | | 215 | | | | | 220 | | | | |
| Leu | Gln | Asp | Arg | Ile | Arg | Met | Tyr | Phe | Asn | Thr | Asn | Xaa | Arg | Leu | Lys |
| 225 | | | | | 230 | | | | | 235 | | | | | 240 |
| Thr | Xaa | Asn | Leu | Ile | Ile | Asn | Asn | Ile | Thr | Arg | Phe | Tyr | Met | Trp | Leu |
| | | | | 245 | | | | | 250 | | | | | 255 | |
| Phe | Gln | Arg | Leu | Met | Tyr | Xaa | Leu | Asn | Ile | Lys | Thr | Tyr | His | Val | Lys |
| | | | | 260 | | | | | 265 | | | | | 270 | |
| Leu | Lys | Ile | Xaa | Asn | Asp | Ile | Ser | Leu | Thr | Asp | Arg | Ser | His | Ile | Met |
| | | | 275 | | | | | 280 | | | | | 285 | | |
| Asn | Phe | Gln | Gly | Leu | Val | Leu | Thr | Asp | Asn | Cys | Lys | Asn | Gln | Trp | Val |
| | | 290 | | | | | 295 | | | | | 300 | | | |
| Val | Gly | Pro | Leu | Ile | Gly | Lys | Gly | Gly | Phe | Gly | Ser | Ile | Tyr | Thr | Thr |
| 305 | | | | | 310 | | | | | 315 | | | | | 320 |
| Asn | Asp | Asn | Asn | Tyr | Val | Val | Lys | Ile | Glu | Pro | Lys | Ala | | | |
| | | | | 325 | | | | | 330 | | | | | | |

( 2 ) INFORMATION FOR SEQ ID NO:65:

( i ) SEQUENCE CHARACTERISTICS:
        ( A ) LENGTH: 333 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..333
        ( D ) OTHER INFORMATION: /note= "Xaa refers to stop codon in the open reading frame."

( x i ) SEQUENCE DESCRIPTION: SEQ ID NO:65:

```
Tyr Leu Val Leu Pro His Xaa Leu Tyr Cys Arg Pro Trp Gln Phe Ser
  1               5                  10                  15

Val Leu His Ile Ile Tyr Ile Ile Asn Val His Val Asn Thr Lys Gln
             20                  25                  30

Arg Thr Lys Ser Arg Phe Leu Thr Tyr Ile Asn Val Trp Asp Ser Lys
         35                  40                  45

Ile Tyr His Ile Glu Arg Thr Ile Trp Phe Arg Lys Asp Ser His Ser
     50                  55                  60

Gln Lys Thr Met Gly Ile Tyr Leu Asp Leu Trp Cys Pro Ile Pro Leu
 65                  70                  75                  80

Asp Phe Leu Val Leu Trp Asn Glu Lys Val Leu Ile Thr Ile Thr Leu
                 85                  90                  95

Thr Glu Arg Pro Ser Gly Arg Glu Xaa Pro Pro Glu Thr Phe Xaa Asn
            100                 105                 110

Ile Leu Ser Phe Xaa Glu Ile Phe Thr Glu Leu Leu Lys Gln Leu Xaa
        115                 120                 125

Ile Gln Arg Leu Leu Ile Ile Val Phe Val Xaa Trp Ile Xaa Thr Ser
    130                 135                 140

Thr Val Leu Glu Val Leu Lys Ile Arg Thr Xaa Cys Leu Thr Arg Cys
145                 150                 155                 160

Ile Xaa Asp Leu Pro Leu Leu Lys Trp Leu Arg Pro Ser Phe Val Val
                165                 170                 175

Glu Thr Leu Lys Leu Thr Met Arg Phe Ile Val Ala Xaa Tyr Trp Gln
            180                 185                 190

Lys Arg Ile Trp Met Arg Pro Thr Lys Gln Val Tyr Ser Thr Leu Leu
        195                 200                 205

Ser Leu Lys Met Met Xaa Ile Xaa His Ile Val Ser Xaa Phe Arg Tyr
    210                 215                 220

Tyr Arg Thr Val Leu Glu Cys Ile Leu Thr Leu Ile Arg Asp Leu Arg
225                 230                 235                 240

Leu Lys Thr Xaa Xaa Leu Ile Ile Xaa Leu Val Phe Ile Cys Gly Tyr
                245                 250                 255

Phe Asn Val Xaa Cys Ile Ser Xaa Ile Leu Lys Leu Thr Thr Xaa Asn
            260                 265                 270

Leu Lys Phe Lys Met Ile Phe His Xaa Gln Ile Asp His Thr Leu Xaa
        275                 280                 285

Thr Phe Lys Asp Leu Cys Xaa Leu Thr Ile Ala Lys Ile Asn Gly Ser
    290                 295                 300

Leu Asp His Xaa Xaa Glu Lys Val Asp Ser Val Val Phe Ile Leu Leu
305                 310                 315                 320
```

```
     Met  Thr  Ile  Ile  Met  Xaa  Xaa  Lys  Xaa  Ser  Pro  Lys  Leu
                    325                      330
```

( 2 ) INFORMATION FOR SEQ ID NO:66:

( i ) SEQUENCE CHARACTERISTICS:
        ( A ) LENGTH: 333 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..333
        ( D ) OTHER INFORMATION: /note= "Xaa refers to stop codon in
            the open reading frame."

( x i ) SEQUENCE DESCRIPTION: SEQ ID NO:66:

```
Ile  Trp  Tyr  Tyr  Arg  Ile  Asn  Tyr  Ile  Val  Gly  Arg  Gly  Asn  Phe  Leu
1                   5                    10                       15

Tyr  Tyr  Ile  Leu  Tyr  Ile  Xaa  Xaa  Thr  Phe  Thr  Xaa  Ile  Gln  Asn  Arg
               20                  25                       30

Glu  Gln  Ser  Leu  Asp  Phe  Xaa  Leu  Thr  Xaa  Met  Ser  Gly  Ile  Val  Lys
          35                       40                       45

Ser  Ile  Ile  Leu  Ser  Gly  Pro  Ser  Gly  Leu  Gly  Lys  Thr  Ala  Ile  Ala
     50                       55                       60

Lys  Arg  Leu  Trp  Glu  Tyr  Ile  Trp  Ile  Cys  Gly  Val  Pro  Tyr  His  Xaa
65                       70                       75                       80

Ile  Ser  Ser  Ser  Tyr  Gly  Thr  Arg  Arg  Cys  Xaa  Leu  Pro  Leu  Arg  Xaa
                    85                       90                       95

Gln  Arg  Gly  His  Leu  Glu  Gly  Asn  Ser  Arg  Arg  Lys  Leu  Ser  Arg  Thr
               100                      105                      110

Tyr  Xaa  Val  Phe  Arg  Lys  Tyr  Leu  Arg  Asn  Phe  Xaa  Asn  Ser  Cys  Glu
          115                      120                      125

Tyr  Ser  Gly  Tyr  Xaa  Xaa  Ser  Tyr  Leu  Cys  Asp  Gly  Ser  Lys  His  Arg
     130                      135                      140

Arg  Cys  Xaa  Lys  Ser  Xaa  Lys  Tyr  Val  Pro  Asn  Ala  Leu  Leu  Gly  Val
145                      150                      155                      160

Tyr  Lys  Thr  Tyr  Leu  Ser  Xaa  Asn  Gly  Xaa  Asp  Gln  Ala  Ser  Leu  Xaa
                    165                      170                      175

Lys  His  Xaa  Ser  Xaa  Arg  Xaa  Asp  Ser  Ser  Arg  Asp  Ile  Gly  Lys
               180                      185                      190

Asn  Gly  Tyr  Gly  Xaa  Gly  Gln  Arg  Ser  Arg  Ser  Ile  Arg  His  Tyr  Tyr
               195                      200                      205

His  Xaa  Arg  Xaa  Cys  Glu  Phe  Ser  Ile  Xaa  Xaa  Val  Asn  Ser  Asp  Thr
     210                      215                      220

Thr  Gly  Pro  Tyr  Xaa  Asn  Val  Phe  Xaa  His  Xaa  Leu  Glu  Thr  Xaa  Asp
225                      230                      235                      240

Leu  Lys  Leu  Asp  Asn  Xaa  Xaa  Tyr  Asn  Ser  Phe  Leu  Tyr  Val  Ala  Ile
                    245                      250                      255

Ser  Thr  Ser  Asn  Val  Leu  Val  Lys  Tyr  Xaa  Asn  Leu  Pro  Arg  Lys  Thr
               260                      265                      270

Xaa  Asn  Leu  Lys  Xaa  Tyr  Phe  Ile  Asp  Arg  Xaa  Ile  Thr  His  Tyr  Glu
          275                      280                      285

Leu  Ser  Arg  Thr  Cys  Val  Asn  Xaa  Gln  Leu  Gln  Lys  Ser  Met  Gly  Arg
     290                      295                      300

Trp  Thr  Ile  Asn  Arg  Lys  Arg  Trp  Ile  Arg  Xaa  Tyr  Leu  Tyr  Tyr  Xaa
```

```
                305                    310                    315                    320
            Xaa Gln Xaa Leu Cys Ser Lys Asn Arg Ala Gln Ser Ser
                                  325                    330
```

( 2 ) INFORMATION FOR SEQ ID NO:67:

( i ) SEQUENCE CHARACTERISTICS:
        ( A ) LENGTH: 1500 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:67:

```
ACCATCGAGG TAACCACCTC TCTGGAAGAC AGCGTGAATA ATGTACTCAT GAAACGTTTG      60
GAAACTATAC GCCATATGTG GTCTGTCGTA TATGATCATT TTGATATTGT GAATGGTAAA     120
GAATGCTGTT ATGTGCATAC GCATTTGTCT AATCAAAATC TTATACCGAG TACTGTAAAA     180
ACAAATTTGT ACATGAAGAC TATGGGATCA TGCATTCAAA TGGATTCCAT GGAAGCTCTA     240
GAGTATCTTA GCGAACTGAA GGAATCAGGT GGATGGAGTC CCAGACCAGA ATGCAGGAA      300
TTTGAATATC CAGATGGAGT GGAAGACACT GAATCAATTG AGAGATTGGT AGAGGAGTTC     360
TTCAATAGAT CAGAACTTCA GGCTGGTGAA TCAGTCAAAT TTGGTAATTC TATTAATGTT     420
AAACATACAT CTGTTTCAGC TAAGCAACTA GAACACGTA TACGGCAGCA GCTTCCTTTA      480
TACTCTCATC TTTTACCAAC ACAAGGGTG GATATTGTT CATTGGAGTT GATAATAATA       540
CACACAAAGT AATTGGATTC ACGGTGGGTC ATGACTACCT CAGACTGGTA GAGAATGATA     600
TAGAAAAGCA TATCAAAAGA CTTCGTGTTG TGCATTTCTG TGAGAAGAAA GAGGACATCA     660
AGTACACGTG TCGATTCATC AAGGTATATA AACCTGGGGA TGAGGCTACC TCGACATACG     720
TGTGCGCTAT CAAAGTGGAA AGATGCTGTT GTGCTGTGTT TGCAGATTGG CCAGAATCAT     780
GGTATATGGA TACTAATGGT ATCAAGAAGT ATTCTCCAGA TGAATGGGTG TCACATATAA     840
AATTTTAATT AATGTAATAG AGAACAAATA ATAAGGTTGT AATATCATAT AGACAATAAC     900
TAACAATTAA TTAGTAACTG TTATCTCTTT TTTAACTAAC CAACTAACTA TATACCTATT     960
AATACATCGT AATTATAGTT CTTAACATCT ATTAATCATT AATTCGCTTC TTTAATTTTT    1020
TATAAACTAA CATTGTTAAT TGAAAAGGGA TAACATGTTA CAGAATATAA ATTATATATG    1080
GATTTTTTTA AAAAGGAAAT ACTTGACTGG AGTATATATT TATCTCTTCA TTATATAGCA    1140
CGCGTGTTTT CCAATTTTTC CACATCCCAT ATAATACAGG ATTATAATCT CGTTCGAACA    1200
TACGAGAAAG TGGATAAAAC AATAGTTGAT TTTTTATCTA GGTTGCCAAA TTTATTCCAT    1260
ATTTTAGAAT ATGGGGAAAA TATTCTACAT ATTTATTCTA TGGATGATGC TAATACGAAT    1320
ATTATAATTT TTTTTCTAGA TAGAGTATTA AATATTAATA AGAACGGGTC ATTTATACAC    1380
AATCTCAGGT TATCATCATC CATTAATATA AAAGAATATG TATATCAATT AGTTAATAAT    1440
GATCATCCAG ATAATAGGAT AAGACTAATG CTTGAAAATG GACGTAGAAC AAGACATTTT    1500
```

( 2 ) INFORMATION FOR SEQ ID NO:68:

( i ) SEQUENCE CHARACTERISTICS:
        ( A ) LENGTH: 500 amino acids
        ( B ) TYPE: amino acid
        ( C ) STRANDEDNESS: single
        ( D ) TOPOLOGY: linear ( i i ) MOLECULE TYPE: protein ( i x ) FEATURE:

( A ) NAME/KEY: Protein
( B ) LOCATION: 1..500
( D ) OTHER INFORMATION: /note= "Xaa refers to stop codon in the open reading frame."

( x i ) SEQUENCE DESCRIPTION: SEQ ID NO:68:

| Thr | Ile | Glu | Val | Thr | Thr | Ser | Leu | Glu | Asp | Ser | Val | Asn | Asn | Val | Leu |
|---|---|---|---|---|---|---|---|---|---|---|---|---|---|---|---|
| 1 | | | | 5 | | | | | 10 | | | | | 15 | |
| Met | Lys | Arg | Leu | Glu | Thr | Ile | Arg | His | Met | Trp | Ser | Val | Val | Tyr | Asp |
| | | | 20 | | | | | 25 | | | | | 30 | | |
| His | Phe | Asp | Ile | Val | Asn | Gly | Lys | Glu | Cys | Cys | Tyr | Val | His | Thr | His |
| | | | 35 | | | | | 40 | | | | | 45 | | |
| Leu | Ser | Asn | Gln | Asn | Leu | Ile | Pro | Ser | Thr | Val | Lys | Thr | Asn | Leu | Tyr |
| | 50 | | | | | 55 | | | | | | 60 | | | |
| Met | Lys | Thr | Met | Gly | Ser | Cys | Ile | Gln | Met | Asp | Ser | Met | Glu | Ala | Leu |
| 65 | | | | | 70 | | | | | 75 | | | | | 80 |
| Glu | Tyr | Leu | Ser | Glu | Leu | Lys | Glu | Ser | Gly | Gly | Trp | Ser | Pro | Arg | Pro |
| | | | | 85 | | | | | 90 | | | | | 95 | |
| Glu | Met | Gln | Glu | Phe | Glu | Tyr | Pro | Asp | Gly | Val | Glu | Asp | Thr | Glu | Ser |
| | | | 100 | | | | | 105 | | | | | 110 | | |
| Ile | Glu | Arg | Leu | Val | Glu | Glu | Phe | Phe | Asn | Arg | Ser | Glu | Leu | Gln | Ala |
| | | | 115 | | | | | 120 | | | | | 125 | | |
| Gly | Glu | Ser | Val | Lys | Phe | Gly | Asn | Ser | Ile | Asn | Val | Lys | His | Thr | Ser |
| | 130 | | | | | 135 | | | | | 140 | | | | |
| Val | Ser | Ala | Lys | Gln | Leu | Arg | Thr | Arg | Ile | Arg | Gln | Gln | Leu | Pro | Leu |
| 145 | | | | | 150 | | | | | 155 | | | | | 160 |
| Tyr | Ser | His | Leu | Leu | Pro | Thr | Gln | Arg | Val | Asp | Ile | Cys | Ser | Leu | Glu |
| | | | | 165 | | | | | 170 | | | | | 175 | |
| Leu | Ile | Ile | Ile | His | Thr | Lys | Xaa | Leu | Asp | Ser | Arg | Trp | Val | Met | Thr |
| | | | 180 | | | | | 185 | | | | | 190 | | |
| Thr | Ser | Asp | Trp | Xaa | Arg | Met | Ile | Xaa | Lys | Ser | Ile | Ser | Lys | Asp | Phe |
| | | | 195 | | | | | 200 | | | | | 205 | | |
| Val | Leu | Cys | Ile | Ser | Val | Arg | Arg | Lys | Arg | Thr | Ser | Ser | Thr | Arg | Val |
| | 210 | | | | | 215 | | | | | 220 | | | | |
| Asp | Ser | Ser | Arg | Tyr | Ile | Asn | Leu | Gly | Met | Arg | Leu | Pro | Arg | His | Thr |
| 225 | | | | | 230 | | | | | 235 | | | | | 240 |
| Cys | Ala | Leu | Ser | Lys | Trp | Lys | Asp | Ala | Val | Val | Leu | Cys | Leu | Gln | Ile |
| | | | | 245 | | | | | 250 | | | | | 255 | |
| Gly | Gln | Asn | His | Gly | Ile | Trp | Ile | Leu | Met | Val | Ser | Arg | Ser | Ile | Leu |
| | | | 260 | | | | | 265 | | | | | 270 | | |
| Gln | Met | Asn | Gly | Cys | His | Ile | Xaa | Asn | Phe | Asn | Xaa | Cys | Asn | Arg | Glu |
| | | | 275 | | | | | 280 | | | | | 285 | | |
| Gln | Ile | Ile | Arg | Leu | Xaa | Tyr | His | Ile | Asp | Asn | Asn | Xaa | Gln | Leu | Ile |
| | 290 | | | | | 295 | | | | | 300 | | | | |
| Ser | Asn | Cys | Tyr | Leu | Phe | Phe | Asn | Xaa | Pro | Thr | Asn | Tyr | Ile | Pro | Ile |
| 305 | | | | | 310 | | | | | 315 | | | | | 320 |
| Asn | Thr | Ser | Xaa | Leu | Xaa | Phe | Leu | Thr | Ser | Ile | Asn | His | Xaa | Phe | Ala |
| | | | | 325 | | | | | 330 | | | | | 335 | |
| Ser | Leu | Ile | Phe | Tyr | Lys | Leu | Thr | Leu | Leu | Ile | Glu | Lys | Gly | Xaa | His |
| | | | 340 | | | | | 345 | | | | | 350 | | |
| Val | Thr | Glu | Tyr | Lys | Leu | Tyr | Met | Asp | Phe | Phe | Lys | Lys | Glu | Ile | Leu |
| | | | 355 | | | | | 360 | | | | | 365 | | |
| Asp | Trp | Ser | Ile | Tyr | Leu | Ser | Leu | His | Tyr | Ile | Ala | Arg | Val | Phe | Ser |
| | | | 370 | | | | | 375 | | | | | 380 | | |
| Asn | Phe | Ser | Thr | Ser | His | Ile | Ile | Gln | Asp | Tyr | Asn | Leu | Val | Arg | Thr |

|     |     |     |     |     | 385 |     |     |     |     | 390 |     |     |     |     | 395 |     |     |     |     | 400 |
|-----|-----|-----|-----|-----|-----|-----|-----|-----|-----|-----|-----|-----|-----|-----|-----|-----|-----|-----|-----|-----|

Tyr Glu Lys Val Asp Lys Thr Ile Val Asp Phe Leu Ser Arg Leu Pro
            405             410                 415

Asn Leu Phe His Ile Leu Glu Tyr Gly Glu Asn Ile Leu His Ile Tyr
            420             425                 430

Ser Met Asp Asp Ala Asn Thr Asn Ile Ile Ile Phe Phe Leu Asp Arg
            435             440                 445

Val Leu Asn Ile Asn Lys Asn Gly Ser Phe Ile His Asn Leu Arg Leu
        450             455             460

Ser Ser Ser Ile Asn Ile Lys Glu Tyr Val Tyr Gln Leu Val Asn Asn
465             470             475                     480

Asp His Pro Asp Asn Arg Ile Arg Leu Met Leu Glu Asn Gly Arg Arg
                485             490                 495

Thr Arg His Phe
            500

( 2 ) INFORMATION FOR SEQ ID NO:69:

( i ) SEQUENCE CHARACTERISTICS:
        ( A ) LENGTH: 500 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..500
        ( D ) OTHER INFORMATION: /note= "Xaa refers to stop codon in
          the open reading frame."

( x i ) SEQUENCE DESCRIPTION: SEQ ID NO:69:

Pro Ser Arg Xaa Pro Pro Leu Trp Lys Thr Ala Xaa Ile Met Tyr Ser
1           5               10              15

Xaa Asn Val Trp Lys Leu Tyr Ala Ile Cys Gly Leu Ser Tyr Met Ile
            20              25              30

Ile Leu Ile Leu Xaa Met Val Lys Asn Ala Val Met Cys Ile Arg Ile
            35              40              45

Cys Leu Ile Lys Ile Leu Tyr Arg Val Leu Xaa Lys Gln Ile Cys Thr
        50              55              60

Xaa Arg Leu Trp Asp His Ala Phe Lys Trp Ile Pro Trp Lys Leu Xaa
65              70              75              80

Ser Ile Leu Ala Asn Xaa Arg Asn Gln Val Asp Gly Val Pro Asp Gln
            85              90              95

Lys Cys Arg Asn Leu Asn Ile Gln Met Glu Trp Lys Thr Leu Asn Gln
            100             105             110

Leu Arg Asp Trp Xaa Arg Ser Ser Ser Ile Asp Gln Asn Phe Arg Leu
            115             120             125

Val Asn Gln Ser Asn Leu Val Ile Leu Leu Met Leu Asn Ile His Leu
        130             135             140

Phe Gln Leu Ser Asn Xaa Glu His Val Tyr Gly Ser Ser Phe Leu Tyr
145             150             155                     160

Thr Leu Ile Phe Tyr Gln His Lys Gly Trp Ile Phe Val His Trp Ser
            165             170             175

Xaa Xaa Xaa Tyr Thr Gln Ser Asn Trp Ile His Gly Gly Ser Xaa Leu
            180             185             190

Pro Gln Thr Gly Arg Glu Xaa Tyr Arg Lys Ala Tyr Gln Lys Thr Ser
            195             200             205

| | | | | | | | | | | | | | | |
|---|---|---|---|---|---|---|---|---|---|---|---|---|---|---|
| Cys | Cys 210 | Ala | Phe | Leu | Xaa 215 | Glu | Ar

| Glu | Thr | Phe | Gly | Asn | Tyr | Thr | Pro | Tyr | Val | Val | Cys | Arg | Ile | Xaa | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |
| Phe | Xaa | Tyr | Cys | Glu | Trp | Xaa | Arg | Met | Leu | Leu | Cys | Ala | Tyr | Ala | Phe |
|     |     | 35  |     |     |     | 40  |     |     |     |     |     | 45  |     |     |     |
| Val | Xaa | Ser | Lys | Ser | Tyr | Thr | Glu | Tyr | Cys | Lys | Asn | Lys | Phe | Val | His |
|     | 50  |     |     |     |     | 55  |     |     |     |     | 60  |     |     |     |     |
| Glu | Asp | Tyr | Gly | Ile | Met | His | Ser | Asn | Gly | Phe | His | Gly | Ser | Ser | Arg |
| 65  |     |     |     |     | 70  |     |     |     |     | 75  |     |     |     |     | 80  |
| Val | Ser | Xaa | Arg | Thr | Glu | Gly | Ile | Arg | Trp | Met | Glu | Ser | Gln | Thr | Arg |
|     |     |     |     | 85  |     |     |     |     | 90  |     |     |     |     | 95  |     |
| Asn | Ala | Gly | Ile | Xaa | Ile | Ser | Arg | Trp | Ser | Gly | Arg | His | Xaa | Ile | Asn |
|     |     |     |     | 100 |     |     |     |     | 105 |     |     |     |     | 110 |     |
| Xaa | Glu | Ile | Gly | Arg | Gly | Val | Leu | Gln | Xaa | Ile | Arg | Thr | Ser | Gly | Trp |
|     |     | 115 |     |     |     |     | 120 |     |     |     |     | 125 |     |     |     |
| Xaa | Ile | Ser | Gln | Ile | Trp | Xaa | Phe | Tyr | Xaa | Cys | Xaa | Thr | Tyr | Ile | Cys |
|     | 130 |     |     |     |     | 135 |     |     |     |     | 140 |     |     |     |     |
| Phe | Ser | Xaa | Ala | Thr | Lys | Asn | Thr | Tyr | Thr | Ala | Ala | Ala | Ser | Phe | Ile |
| 145 |     |     |     |     | 150 |     |     |     |     | 155 |     |     |     |     | 160 |
| Leu | Ser | Ser | Phe | Thr | Asn | Thr | Lys | Gly | Gly | Tyr | Leu | Phe | Ile | Gly | Val |
|     |     |     |     | 165 |     |     |     |     | 170 |     |     |     |     | 175 |     |
| Asp | Asn | Asn | Thr | His | Lys | Val | Ile | Gly | Phe | Thr | Val | Gly | His | Asp | Tyr |
|     |     |     | 180 |     |     |     |     | 185 |     |     |     |     | 190 |     |     |
| Leu | Arg | Leu | Val | Glu | Asn | Asp | Ile | Glu | Lys | His | Ile | Lys | Arg | Leu | Arg |
|     |     | 195 |     |     |     |     | 200 |     |     |     |     | 205 |     |     |     |
| Val | Val | His | Phe | Cys | Glu | Lys | Lys | Glu | Asp | Ile | Lys | Tyr | Thr | Cys | Arg |
|     | 210 |     |     |     |     | 215 |     |     |     |     | 220 |     |     |     |     |
| Phe | Ile | Lys | Val | Tyr | Lys | Pro | Gly | Asp | Glu | Ala | Thr | Ser | Thr | Tyr | Val |
| 225 |     |     |     |     | 230 |     |     |     |     | 235 |     |     |     |     | 240 |
| Cys | Ala | Ile | Lys | Val | Glu | Arg | Cys | Cys | Cys | Ala | Val | Phe | Ala | Asp | Trp |
|     |     |     |     | 245 |     |     |     |     | 250 |     |     |     |     | 255 |     |
| Pro | Glu | Ser | Trp | Tyr | Met | Asp | Thr | Asn | Gly | Ile | Lys | Lys | Tyr | Ser | Pro |
|     |     |     | 260 |     |     |     |     | 265 |     |     |     |     | 270 |     |     |
| Asp | Glu | Trp | Val | Ser | His | Ile | Lys | Phe | Xaa | Leu | Met | Xaa | Xaa | Arg | Thr |
|     |     | 275 |     |     |     |     | 280 |     |     |     |     | 285 |     |     |     |
| Asn | Asn | Lys | Val | Val | Ile | Ser | Tyr | Arg | Gln | Xaa | Leu | Thr | Ile | Asn | Xaa |
|     | 290 |     |     |     |     | 295 |     |     |     |     | 300 |     |     |     |     |
| Xaa | Leu | Leu | Ser | Leu | Phe | Xaa | Leu | Thr | Asn | Xaa | Leu | Tyr | Thr | Tyr | Xaa |
| 305 |     |     |     |     | 310 |     |     |     |     | 315 |     |     |     |     | 320 |
| Tyr | Ile | Val | Ile | Ile | Val | Leu | Asn | Ile | Tyr | Xaa | Ser | Leu | Ile | Arg | Phe |
|     |     |     |     | 325 |     |     |     |     | 330 |     |     |     |     | 335 |     |
| Phe | Asn | Phe | Leu | Xaa | Thr | Asn | Ile | Val | Asn | Xaa | Lys | Gly | Ile | Thr | Cys |
|     |     |     | 340 |     |     |     |     | 345 |     |     |     |     | 350 |     |     |
| Tyr | Arg | Ile | Xaa | Ile | Ile | Tyr | Gly | Phe | Phe | Xaa | Lys | Gly | Asn | Thr | Xaa |
|     |     | 355 |     |     |     |     | 360 |     |     |     |     | 365 |     |     |     |
| Leu | Glu | Tyr | Ile | Phe | Ile | Ser | Ser | Leu | Tyr | Ser | Thr | Arg | Val | Phe | Gln |
|     | 370 |     |     |     |     | 375 |     |     |     |     | 380 |     |     |     |     |
| Phe | Phe | His | Ile | Pro | Tyr | Asn | Thr | Gly | Leu | Xaa | Ser | Arg | Ser | Asn | Ile |
| 385 |     |     |     |     | 390 |     |     |     |     | 395 |     |     |     |     | 400 |
| Arg | Glu | Ser | Gly | Xaa | Asn | Asn | Ser | Xaa | Phe | Phe | Ile | Xaa | Val | Ala | Lys |
|     |     |     |     | 405 |     |     |     |     | 410 |     |     |     |     | 415 |     |
| Phe | Ile | Pro | Tyr | Phe | Arg | Ile | Trp | Gly | Lys | Tyr | Ser | Thr | Tyr | Leu | Phe |
|     |     |     | 420 |     |     |     |     | 425 |     |     |     |     | 430 |     |     |
| Tyr | Gly | Xaa | Cys | Xaa | Tyr | Glu | Tyr | Tyr | Asn | Phe | Phe | Ser | Arg | Xaa | Ser |
|     |     | 435 |     |     |     |     | 440 |     |     |     |     | 445 |     |     |     |

|     |     |     |     |     |     |     |     |     |     |     |     |     |     |     |
|-----|-----|-----|-----|-----|-----|-----|-----|-----|-----|-----|-----|-----|-----|-----|
| Ile | Lys | Tyr | Xaa | Xaa | Glu | Arg | Val | Ile | Tyr | Thr | Gln | Ser | Gln | Val | Ile |
|     | 450 |     |     |     |     | 455 |     |     |     |     | 460 |     |     |     |
| Ile | Ile | His | Xaa | Tyr | Lys | Arg | Ile | Cys | Ile | Ser | Ile | Ser | Xaa | Xaa | Xaa |
| 465 |     |     |     |     | 470 |     |     |     |     | 475 |     |     |     |     | 480 |
| Ser | Ser | Arg | Xaa | Xaa | Asp | Lys | Thr | Asn | Ala | Xaa | Lys | Trp | Thr | Xaa | Asn |
|     |     |     |     | 485 |     |     |     |     | 490 |     |     |     |     | 495 |     |
| Lys | Thr | Phe | Phe |
|     |     |     | 500 |